(12) United States Patent
von Haken Spence et al.

(10) Patent No.: US 6,440,890 B1
(45) Date of Patent: Aug. 27, 2002

(54) HYDROCARBYL PHOSPHINIMINE/ CYCLOPENTADIENYL COMPLEXES OF GROUP IV METALS AND PREPARATION THEREOF

(75) Inventors: Rupert Edward von Haken Spence; Stephen John Brown, both of Calgary; Ryan Paul Wurz, Montreal; Dusan Jeremic, Calgary; Douglas W. Stephan, LaSalle, all of (CA)

(73) Assignee: NOVA Chemicals (International) S.A., Villars-sur-Glane 1 (CH)

( * ) Notice: Subject to any disclaimer, the term of this patent is extended or adjusted under 35 U.S.C. 154(b) by 103 days.

(21) Appl. No.: 09/656,126

(22) Filed: Sep. 6, 2000

(30) Foreign Application Priority Data

Sep. 10, 1999 (CA) .............................................. 2282070

(51) Int. Cl.[7] ........................... B01J 31/24; B01J 31/38; C08F 4/44

(52) U.S. Cl. ....................... 502/155; 502/103; 502/117; 502/152; 526/160; 526/161; 526/943; 526/172; 556/13; 556/53

(58) Field of Search ................................. 502/152, 155, 502/103, 117; 526/160, 161, 943

(56) References Cited

U.S. PATENT DOCUMENTS 5,965,677 A    10/1999   Stephan et al. ............. 526/129

Primary Examiner—David W. Wu
Assistant Examiner—R. Harlan
(74) Attorney, Agent, or Firm—Kenneth H. Johnson

(57) ABSTRACT

New group 4 organometallic complexes are characterized by having a phosphinimine ligand and two or more cyclopentadienyl ligands. Certain of these complexes exhibit unusual behavior when examined by nuclear magnetic resonance (NMR) techniques. Well defined crystals of the inventive complexes have been isolated and analyzed by x-ray crystallography. The complexes have also been found to be polymerization catalysts which are surprisingly more active than their simple metallocene analogs.

5 Claims, 4 Drawing Sheets

HYDROCARBYL PHOSPHINIMINE/ CYCLOPENTADIENYL COMPLEXES OF GROUP IV METALS AND PREPARATION THEREOF

FIELD OF THE INVENTION

This invention relates to novel organometallic complexes. Additionally, the complexes have been discovered to be surprisingly active catalysts for the polymerization of olefins.

BACKGROUND OF THE INVENTION

The polymerization of olefins using a catalyst having a phosphinimine ligand and a cyclopentadienyl ligand is known and is disclosed for example in copending and commonly assigned U.S. patent application Ser. No. 08/959,589 (Stephan et al) (now U.S Pat. No. 5,965,677). These prior catalysts have an "activatable" ligand which is not a cyclopentadienyl ligand. Exemplary activatable ligands include halides, alkyls, amides and phosphides.

We have now surprisingly discovered and reproducibly synthesized a group of novel organometallic complexes of group 4 metals having a phosphinimine ligand and more than one cyclopentadienyl ligand. These novel complexes form unique crystal structures which may be observed by x-ray techniques.

The organometallic complexes of this invention might be regarded as metallocenes because they contain two or more cyclopentadienyl ligands. It is known that metallocenes of group 4 metals are active catalysts for the polymerization of ethylene. However, we have discovered that certain organometallic complexes of this invention are substantially more active for ethylene polymerization than their simple metallocene analogs.

SUMMARY OF THE INVENTION

In one embodiment, the invention provides an organometallic complex defined by the formula:

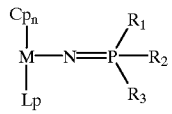

wherein M is a group 4 metal in oxidation state 4; each Cp is selected from the group consisting of unsubstituted cyclopentadienyl, substituted cyclopentadienyl, unsubstituted indenyl, substituted indenyl, unsubstituted fluorenyl and substituted fluorenyl; each of $R_1$, $R_2$ and $R_3$ is a hydrocarbyl group which is bonded to phosphorus by a carbon-phosphorus single bond;

n is 2 or 3 and n+p=3; and when p=1, L is a monoanionic ligand.

Preferred metals are titanium, zirconium and hafnium, particularly titanium.

As noted above, the novel complexes of this invention must contain either 2 or 3 cyclopentadienyl ligands. As such, they may be regarded as metallocenes. The term "cyclopentadienyl" ligand as used herein is meant to convey its broad but conventional meaning and to be inclusive of both substituted and unsubstituted cyclopentadienyl, indenyl and fluorenyl ligands. Examples of suitable substituents include alkyl groups; halide substituents (i.e. substituents which contain Br, Cl, I or F atoms) or heteroatom substituents (i.e. substituents which contain N, S, O or P atoms). For reasons of low cost and ease of organometallic synthesis, the use of unsubstituted cyclopentadienyl and unsubstituted indenyl ligands is preferred.

The hydrocarbyl groups are preferably alkyl group having from 1 to 10 carbon atoms. Tertiary butyl groups are particularly preferred. The hydrocarbyl groups may also contain substituents, especially halide substituents (i.e. containing Br, Cl, I or F atoms) or heteroatom substituents (i.e. substituents which contain N, S, O or P atoms).

BRIEF DESCRIPTION OF THE FIGURES

The following abbreviations have been used in this specification:

Cp=cyclopentadienyl t-Bu=tertiary butyl

Me=methyl

Figure 1:
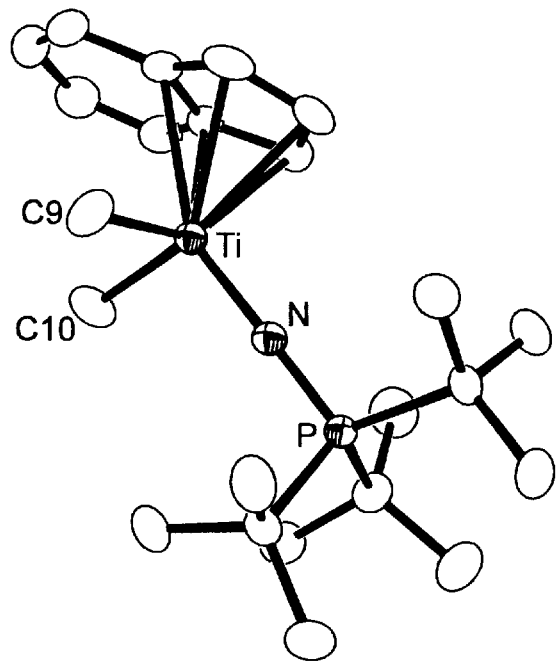

FIG. 1: Oakridge Thermal Ellipsoid Plot ("ORTEP") drawings of (Indenyl)Ti(NP-t-Bu$_3$)Me$_2$ (5), 30% thermal ellipsoids are shown. Hydrogen atoms have been omitted for clarity. Ti—N 1.782(2) Å; Ti—C(10) 2.123(3) Å; Ti—C(9) 2.133(3) Å; P—N 1.585(2) Å; N—Ti—C(10) 103.78(10)°; N—Ti—C(9) 101.83(9)°; C(10)-Ti—C(9) 99.50(13)°; P—N—Ti 178.38(11)°.

Figure 2:
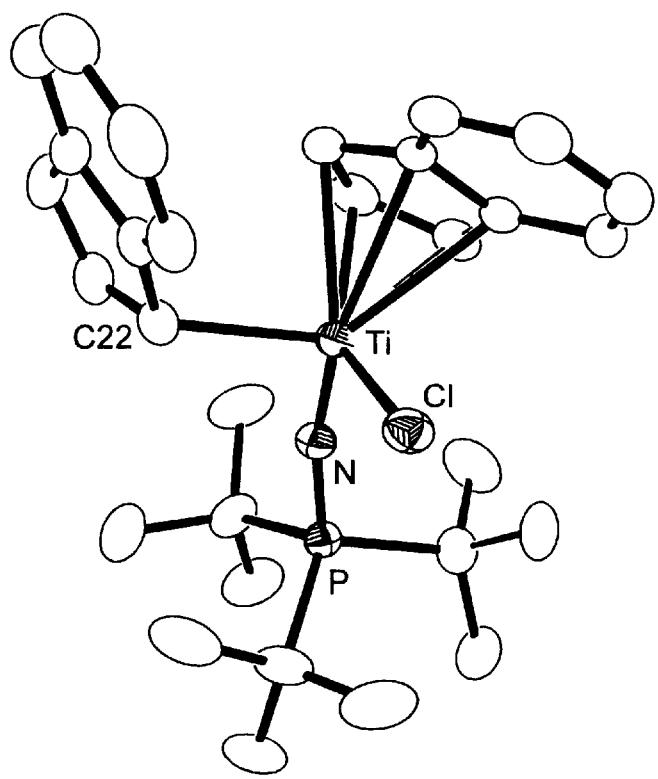

FIG. 2: ORTEP drawings of (Indenyl)$_2$Ti(NP-t-Bu$_3$)Cl (8), 30% thermal ellipsoids are shown. Hydrogen atoms have been omitted for clarity. Ti—N 1.775(2) Å; Ti—C(22) 2.229(3) Å; Ti—Cl 2.2947(10) Å; P—N 1.609(3) Å; N—Ti—C(22) 99.17(12)°; N—Ti—Cl 104.63(9)°; C(22)-Ti—Cl 97.10(10)°; P—N—Ti 167.4(2)°.

Figure 3:
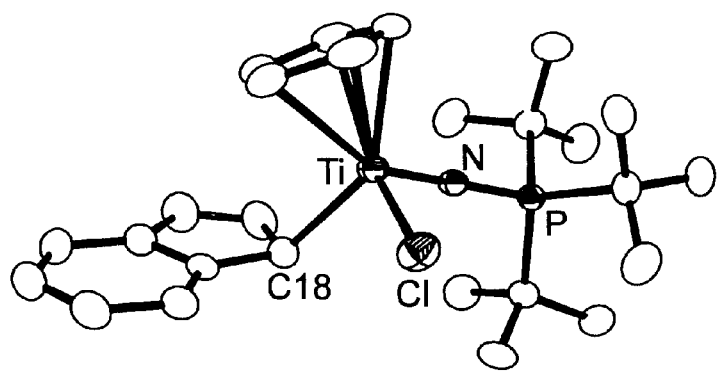

FIG. 3: ORTEP drawings of Cp(Indenyl)Ti(NP-t-Bu$_3$)Cl (9), 30% thermal ellipsoids are shown. Hydrogen atoms have been omitted for clarity. Ti—N 1.773(4) Å; Ti—C(18) 2.198(5) Å; Ti—Cl(1) 2.299(2) Å; P—N 1.604(4) Å; (1)-Ti—C(18) 98.9(2)°; N—Ti—Cl(1) 103.03(14)°; C(18)-Ti—Cl(1) 99.8(2)°; P—N 169.1(2)°.

Figure 4:
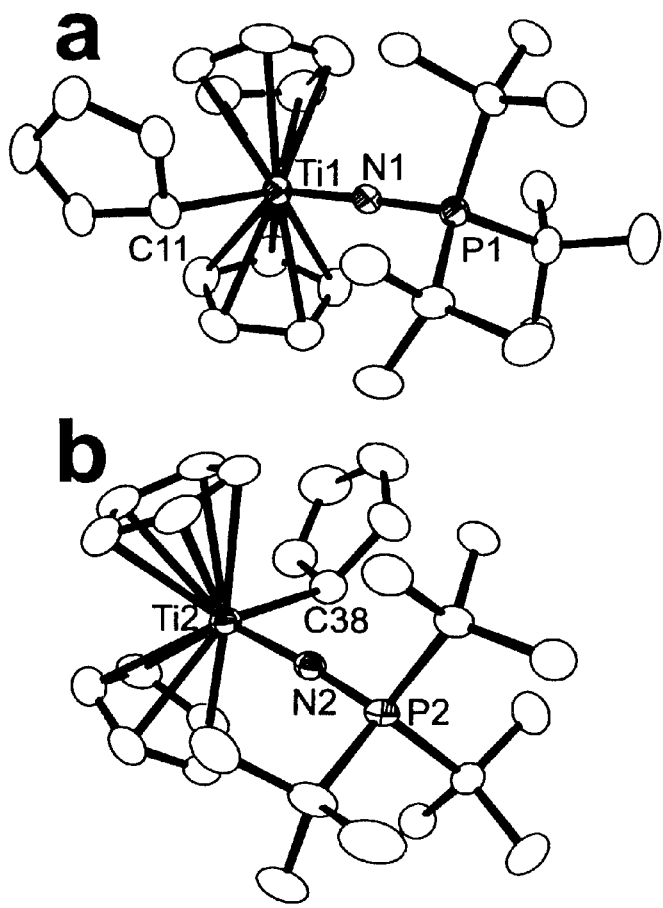

FIG. 4: ORTEP drawing of the two independent molecules (a) and (b) of Cp$_3$Ti(NP-t-Bu$_3$) (10) in the asymmetric unit. 30% thermal ellipsoids are shown. Hydrogen atoms have been omitted for clarity. Ti(1)-N(1) 1.844(2) Å; Ti(1)-C(11) 2.378(2) Å; Ti(2)-N(2) 1.850(2) Å; Ti(2)-C(38) 2.355(2) Å; P(1)-N(1) 1.590(2) Å; P(2)-N(2) 1.590(2) Å; N(1)-Ti(1)-C(11) 92.71(7)°; N(2)-Ti(2)-C(38) 92.79(7)°; P(1)-N(1)-Ti(1) 175.56(9)°; P(2)-N(2)-Ti(2) 175.43(9)°.

Figure 5:
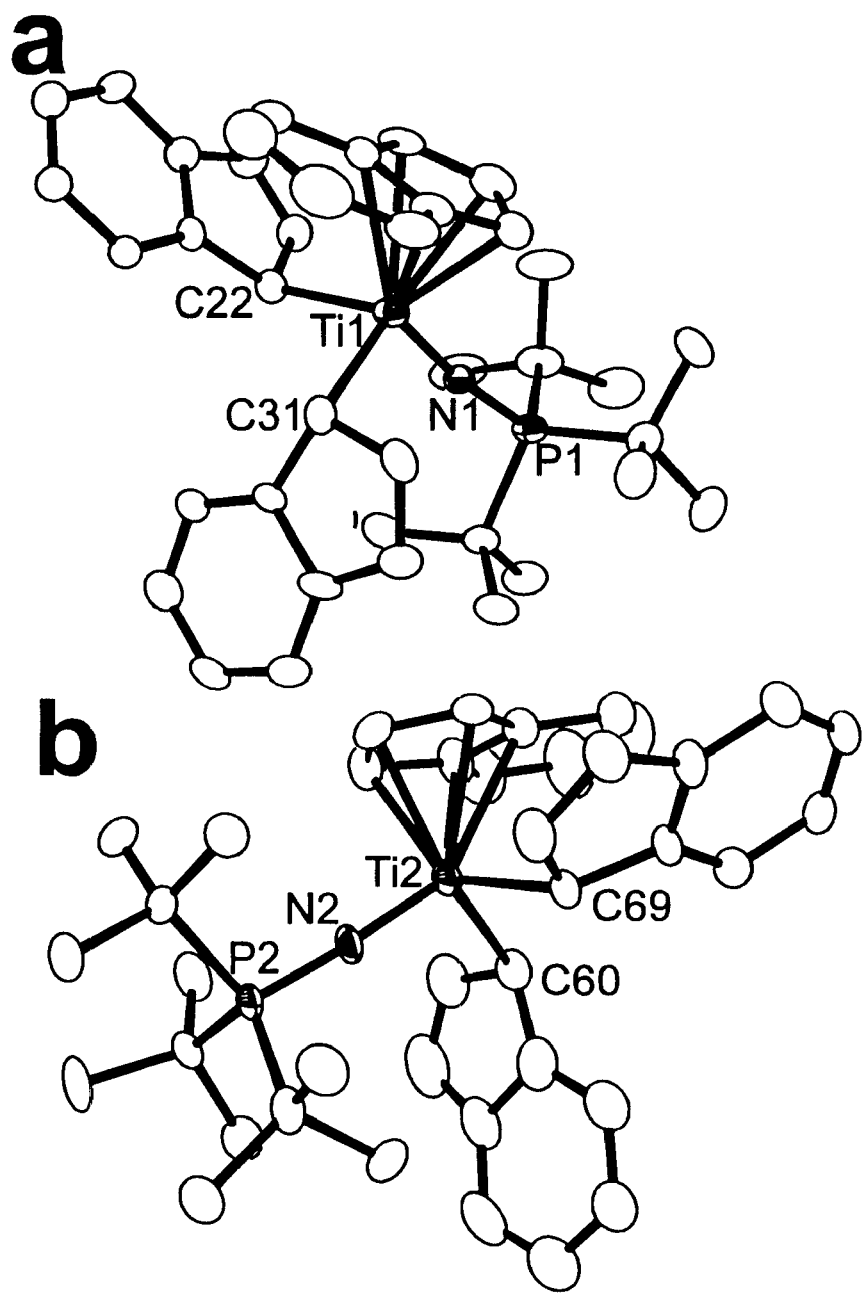

FIG. 5: ORTEP drawing of the two independent molecules (a) and (b) of (Indenyl)$_3$Ti(NP-t-Bu$_3$) (11) in the asymmetric unit. 30% thermal ellipsoids are shown. Hydrogen atoms have been omitted for clarity. Ti(1)-N(1) 1.786(5) Å; Ti(1)-C(22) 2.212(7) Å; Ti(1)-C(31) 2.217(7) Å; Ti(2)-N(2) 1.774(5) Å; Ti(2)-C(69) 2.205(7) Å; Ti(2)-C(60) 2.221(8) Å; P(1)-N(1) 1.613(5) Å; P(2)-N(2) 1.627(5) Å; N(1)-Ti(1)-C(22) 100.1(2)°; N(1)-Ti(1)-C(31) 108.1(3)°; C(22)-Ti(1)-C(31) 98.0(3)°; N(2)-Ti(2)-C(69) 99.3(3)°; N(2)-Ti(2)-C(60) 108.1(3)°; C(69)-Ti(2)-C(60) 98.2(3)°; P(1)-N(1)-Ti(1) 171.6(4)°; P(2)-N(2)-Ti(2) 175.2(4)°.

Figure 6:
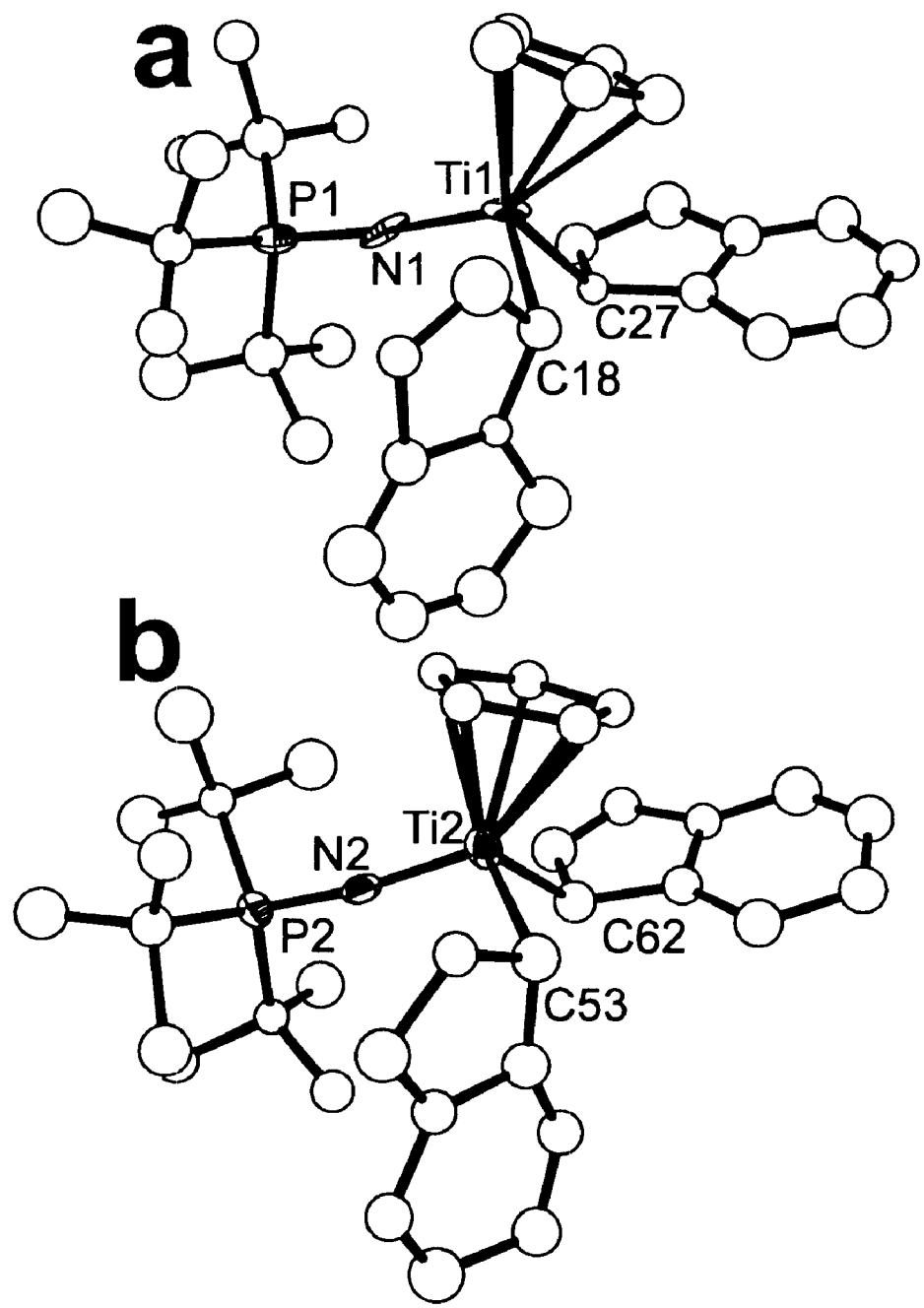

FIG. 6: ORTEP drawing of the two independent molecules (a) and (b) of Cp(Indenyl)$_2$Ti(NP-t-Bu$_3$) (12) in the asymmetric unit. 30% thermal ellipsoids are shown. Hydrogen atoms have been omitted for clarity. Ti(1)-N(1) 1.77(2) Å; Ti(1)-C(27) 2.26(2) Å; Ti(1)-C(18) 2.27(2) Å; Ti(2)-N(2) 1.80(2) Å; Ti(2)-C(62) 2.18(2) Å; Ti(2)-C(53) 2.19(2) Å; P(1)-N(1) 1.61(2) Å; P(2)-N(2) 1.62(2) Å; N(1)-Ti(1)-C(27) 100.9(7)°; N(1)-Ti(1)-C(18) 108.3(8)°; C(27)-Ti(1)-C(18) 95.1(8)°; N(2)-Ti(2)-C(62) 100.4(8)°; N(2)-Ti(2)-C(53) 107.8(9)°; C(62)-Ti(2)-C(53) 99.2(9)°; P(1)-N(1)-Ti(1) 174.5(11)°; P(2)-N(2)-Ti(2) 172.3(12)°.

DETAILED DESCRIPTION

We have discovered a new series of group 4 metal complexes with a phosphinimine ligand and two or more cyclopentadienyl ligands. These compounds have been examined and characterized by various analytical techniques including x-ray crystallography.

Synthetic routes to the species described herein are described in detail in the Experimental section. We have previously described the facile synthesis of CpTi(NP-t-Bu$_3$)Cl$_2$ 1. In a similar manner, the reaction of Me$_3$SiNP-t-Bu$_3$ 2 and (Indenyl)TiCl$_3$ 3 affords the species (Indenyl)Ti(NP-t-Bu$_3$)Cl$_2$ 4 in approximately 95% isolated yield. This species is readily converted to (Indenyl)Ti(NP-t-Bu$_3$)Me$_2$ 5 in 86% yield via reaction with methyl Grignard. This light yellow crystalline product exhibits methyl resonances in $^1$H NMR spectrum at 0.16 ppm. Compound 5 was also characterized by x-ray crystallography (FIG. 1). These data reveal Ti-methyl carbon distances average 2.128(4) Å with a C—Ti—C angle of 99.50(13)°. The phosphinimide ligand geometry is typical of that seen in CpTi-phosphinimide complexes. The Ti—N and P—N distances in 5 are 1.782(2) Å and 1.585(2) Å respectively with a P—N—Ti angle approaching linearity (178.38(11)°).

Reaction of 1 with one equivalent of the dimethyl ether complex of sodium cyclopentadiene ["(dme)NaCp"] affords the dark red product Cp$_2$Ti(NP-t-Bu$_3$)Cl 7 in 93% isolated yield. The $^1$H NMR spectrum of 7 shows a single resonance at 6.21 ppm attributable to the cyclopentadienyl protons. The spectral features are temperature invariant, thus inferring that both cyclopentadienyl rings are bound to the metal in a $\eta^5$ bonding mode. In a similar synthetic procedure, reaction of 6 with Li(Indenyl) yields the complex (Indenyl)$_2$Ti(NP-t-Bu$_3$)Cl 8 in 86% isolated yield. The $^1$H NMR data infer the presence of both an $\eta^5$ and an $\eta^1$ bound indenyl ligand as the overlapping resonances accounting for 14 protons give rise to six signals. These NMR features of 8 are invariant with temperature even on heating solutions of 8 to 80° C. Crystallographic study of 8 (FIG. 2) confirmed the interpretation of the NMR data and the presence of $\eta^5$ and $\eta^1$ bound indenyl ligands. The Ti—N and Ti—Cl distances in 8 are 1.775(2) Å and 2.2947(10) Å respectively. The Ti—C distance for the $\eta^1$-indenyl ligand is 2.229(3) Å. This distance is slightly longer than the $\sigma$-Ti—C found in 5, consistent with the greater steric demands of the indenyl ligands.

We have also discovered that the mixed cyclopentadienyl-indenyl species, Cp(Indenyl)Ti(NP-t-Bu$_3$)Cl 9 can also be prepared via two alternative pathways. Either reaction of 4 with one equivalent of (dme)NaCp or reaction of 1 with Li(Indenyl) afford dark red crystalline of 9. Regardless of the synthetic route, $^1$H and $^{13}$C{$^1$H} NMR data indicate that the product 9 contains an $\eta^5$-cyclopentadienyl group and an $\eta^1$-indenyl fragment. This was also affirmed by the results of an x-ray crystallographic study (FIG. 3). While most of the metric parameters within 9 are similar to those seen in 8, it is noteworthy that the lesser steric congestion in 9 results in a shorter Ti—C bond of 2.198(5) Å. The synthesis of 9 from 1 involves a facile nucleophilic substitution. In contrast, the path to 9 from 4 likely requires an interesting $\eta^5$-$\eta^1$-indenyl ring-slippage.

Complex 1 reacts with two equivalents of (dme)NaCp to give the dark red crystalline product 10 formulated as Cp$_3$Ti(NP-t-Bu$_3$) in 89% yield. $^1$H and $^{13}$C{$^1$H} NMR spectra show single resonances at 6.03 and 114.57 ppm respectively attributable to the cyclopentadienyl ligands. Cooling to −80° C. reveals no change in these resonances suggesting a rapid process of site exchange. It should be noted that the three cyclopentadienyl ligands may be $\eta^5$ bonded although this proposition is unlikely for both steric and electronic reasons. Moreover, an x-ray crystallographic analysis of 10 (FIG. 4) reveals that the molecule contains two $\eta^5$- and one $\eta^1$-cyclopentadienyl groups in the solid state. Whilst not wishing to be bound by theory, this geometry likely results in a relatively electron rich metal center in 10 compared to 5, 8 and 9. The significant lengthening of the Ti—N to 1.844(2) Å and the Ti—C $\sigma$-bonds to 2.366(4) Å support this view.

The analogous species (Indenyl)$_3$Ti(NP-t-Bu$_3$) 11 is obtained from the reaction of 4 with excess Li(Indenyl). This results in the dark red crystalline product 11 in 95% yield. The $^1$H NMR data show four resonances at 25° C., which sharpen on heating, again inferring an $\eta^5$-$\eta^1$-site exchange process. On cooling to −80° C. eighteen resonances are observed, inferring the presence of inequivalent $\eta^5$- and $\eta^1$-indenyl rings. The precise assessment of the exchange barrier is a complicated issue as the exchange process appears to involve three sites for each of seven protons. Consequently, the coalescence of resonances can not be unambiguously observed, although it appears that coalescence of the resonances in the $^1$H NMR spectra of 11 occurs at approximately −25° C. This infers an approximate barrier to $\eta^5$- and $\eta^1$-indenyl site exchange of 8–9 Kcal/mol.

An x-ray crystallographic study of 11 confirmed that this species in the solid state contains a single $\eta^5$- and two $\eta^1$-indenyl ligands (FIG. 5). The Ti—N$_{avg}$ (1.780(6) Å) in 11 are similar to those seen in 5, 8 and 9, while the Ti—C are slightly longer (Ti—C$_{avg}$ 2.215(7) Å) although not as long as those seen in the more electron rich species 10. Whilst not wishing to be bound by theory, it is, presumably, the greater steric demands of the indenyl ligands that preclude the binding of two of such ligands in $\eta^5$-manner. However, it is not possible to exclude the possibility that the phosphinimine ligand is in this compound a better 6-electron donor ligand than indenyl.

The mixed cyclopentadienyl-indenyl species Cp(Indenyl)$_2$Ti(NP-t-Bu$_3$) 12 is also accessible from the reaction of 1 and excess Li(Indenyl). The $^1$H NMR data show four resonances inferring the presence of an $\eta^5$-cyclopentadienyl and two $\eta^1$-indenyl ligands. This interpretation was confirmed crystallographically (FIG. 6). The metric parameters are unexceptional as they mimic those observed for 5, 8, 9 and 11. In contrast to 11, compound 12 appears to be a rigid molecule in which there is no interchange of $\eta^5$-cyclopentadienyl and the two $\eta^1$-indenyl ligands.

Whilst not wishing to be bound by theory, it may be postulated that steric crowding is a factor determining the binding modes of the cyclopentadienyl and/or indenyl ligands in the series of compounds described herein. The steric demands of the larger indenyl ligand and its extended $\pi$-system likely facilitate ring slippage and thus favor $\eta^1$-binding. While the geometries of the phosphinimide ligands are relatively constant, with only minor changes in the P—N bond distance and Ti—N—P bond angle, there is a clear effect of the electronic environment at the metal center on the Ti—N bond distance. In the formally 18 electron species 10, the Ti—N bond was observed to about 1.844(2) Å. In contrast, in 5, 8, 9, 11 and 12 the electron count is formally 16 and the Ti—N is strengthened and shortens to an observed length of about 1.77 Å.

Group 4 metal complexes with only two cyclopentadienyl rings or two indenyl rings classically have both rings $\eta^5$-bonded to the metal center. We are not aware of any well characterized examples of such species where the ring system is $\eta^1$-bonded to the metal. The closest exception to this observation is in the Cp$_3$MX and Cp$_4$M complexes with more than two cyclopentadienes. In these systems two of the cyclopentadienes are $\eta^5$-bonded while the remaining cyclopentadienes are $\eta^1$-bonded. These systems have been termed "whiz" compounds as the sigma bound and $\pi$ bound cyclopentadienes generally rapidly interchange.

The phosphinimine compounds described herein have at least two cyclopentadienyl ligands which may be substituted cyclopentadienyl ligands and a phosphinimine ligands. The compounds described are unique in structure. The x-ray crystallographic data and NMR spectroscopy data demonstrate that the cyclopentadienyl ligands or indenyl ligands can be $\eta^1$ or $\eta^5$ bonded to the metal depending on the number and type of cyclopentadienyl ligands or indenyl ligands present. The NMR spectroscopy data also shows that, for some of the novel compounds, ring whizzing can occur in solution. This $\eta^1$–$\eta^5$ site exchange can be slowed by lowering the temperature. Of course, the $\eta^1$–$\eta^5$ site exchange is not observed when the complexes are frozen into crystals for x-ray analysis.

PART A: EXPERIMENTAL

All preparations were done under an atmosphere of dry, O$_2$-free N$_2$ employing both Schlenk line techniques and an inert atmosphere glove box. Solvents were purified employing a Grubb's type column system. All organic reagents were purified by conventional methods. $^1$H and $^{13}$C{$^1$H} NMR spectra were recorded on one of two spectrometers (Bruker Avance-300 and 500 operating at 300 and 500 MHz, respectively). Trace amounts of protonated solvents were used as references and chemical shifts are reported relative to SiMe$_4$. $^{31}$P NMR spectra were recorded on a Bruker Avance-300 and are referenced to 85% H$_3$PO$_4$. The precursor complexes CpTi(NP-t-Bu$_3$)Cl$_2$ 1, Me$_3$SiNP-t-Bu$_3$ 2 and (Indenyl)TiCl$_3$ 3 were prepared via conventional (previously reported) methods.

Synthesis of (Indenyl)Ti(NP-t-Bu$_3$)Cl$_2$ (4)

Compound 2 (0.250 g; 0.864 mmol) was added to a toluene solution (50 mL) of 3 (0.230 g; 0.854 mmol). The solution was heated to 110° C. for 12 hours. The volatile products were removed in vacuo to yield a bright yellow solid. The solid was washed with hexane (3×25 mL), filtered and dried under vacuum (0.365 g; 0.810 mmol; 95%). $^1$H NMR δ 7.80 (m, 2H, Indenyl), 7.19 (m, 2H, Indenyl), 6.85 (t, 1H, Indenyl), 6.60 (d, 2H, Indenyl), 1.15 (d, J$^3_{PH}$=13.7 Hz; 27H; t-Bu). $^{13}$C{$^1$H} NMR δ 129.07, 125.64, 125.29, 115.98, 105.21, 42.00 (d, J$^1_{PC}$=44.5 Hz, PCMe$_3$), 29.41. $^{31}$P{$\eta^1$H} NMR δ 46.12.

Synthesis of (Indenyl)Ti(NP-t-Bu$_3$)Me$_2$ (5)

To a diethylether solution (25 mL) of complex 4 (0.250 g; 0.555 mmol) was added an excess of MeMgBr (0.42 mL; 3.0 M; 1.25 mmol) at room temperature. The solution was stirred for 12 hours. The solvent 10 was removed in vacuo and the solid extracted with hexane (3×25 mL). The volume of the solvent was reduced to 10 mL and the solution was left to crystallize overnight. Light yellow crystalline 5 was isolated by filtration and dried under vacuum (0.195 g; 0.476 mmol; 86%). $^1$H NMR δ 7.67 (m, 2H, Indenyl), 7.20 (m, 2H, Indenyl), 6.85 (d, 2H, Indenyl), 6.01 (t, 1H, Indenyl), 1.20 (d, J$^3_{PH}$=13.0 Hz, 27H, P$^t$Bu$_3$), 0.16 (s, 6H, TiMe$_2$). $^{13}$C{$^1$H} NMR δ 126.54, 125.02, 123.48, 112.71, 100.62, 42.86 (TiMe$_2$), 41.30 (d, J$^1_{PC}$=46.1 Hz, PCMe$_3$), 29.57. $^{31}$P{$^1$H} NMR δ 31.93. This light yellow crystalline product exhibits methyl resonances in $^1$H NMR spectrum at 0.16 ppm. Compound 5 was also characterized by x-ray crystallography (FIG. 1). These data reveal Ti-methyl carbon distances average 2.128(4) Å with a C—Ti—C angle of 99.50(13)°. The phosphinimide ligand geometry is similar to that seen in simple CpTi-phosphinimide complexes. The Ti—N and P—N distances in 5 are 1.782(2) Å and 1.585(2) Å respectively with a P—N—Ti angle approaching linearity (178.38(11)°).

Synthesis of (t-Bu$_3$PN)TiCl$_3$ (6)

To a solution of TiCl$_4$ (0.327 g; 1.73 mmol) in xylenes (3.5 mL) was added a solution of 2 (0.500 g; 1.73 mmol) in xylenes (3.5 mL). The reaction was then heated to 135° C. in an oil bath. After 17 hours the solution was cooled and a filtration of the solution yielded (0.575 g; 1.55 mmol; 90%) of 6 as a yellow powder. $^1$H NMR δ 1.08 (d, J$^3_{PH}$=14.2 Hz; 27H; t-Bu).

Synthesis of Cp$_2$Ti(NP-t-Bu$_3$)Cl (7)

To a THF solution (10 mL) of complex 1 (0.250 g; 0.625 mmol) was added one equivalent of NaCp.DME (0.100 g; 0.625 mmol) at 20° C. The yellow solution turned dark red within minutes. The solution was stirred for 12 hours and the solvent was removed under vacuum to yield a dark red solid. The solid was extracted with hot benzene (3×25 mL). The volume of the filtrate was reduced to 10 mL and the solution left to crystallize for 12 hours. Dark red crystalline 7 was isolated by filtration and dried under vacuum (0.251 g; 0.584 mmol; 93%). $^1$H NMR δ 6.21 (s, 10H, Cp), 1.17 (d, J$^3_{PH}$=13.1 Hz, 27H, PtBu$_3$). $^{13}$C{$^1$H} NMR δ 115.06, 41.80 (d, J$^1_{PC}$=45.9 Hz, PCMe$_3$), 29.99. $^{31}$P{$^1$H} NMR δ 39.45. The $^1$H NMR spectrum of 7 shows a single resonance at 6.21 ppm attributable to the cyclopentadienyl protons. The spectral features are temperature invariant. Whilst not wishing to be bound by theory, this suggests that both cyclopentadienyl rings are bound to the metal in a $\eta^5$ bonding mode.

Synthesis of (Indenyl)$_2$Ti(NP-t-Bu$_3$)Cl (8)

The synthesis of complex 8 is similar to that of 7. Complex 4 (0.300 g; 0.666 mmol) and Li(Indenyl) (0.081 g; 0.663 mmol) afford dark red crystalline 8 (0.302 g; 0.570 mmol; 86%). Alternatively, complex 8 can be synthesized from 6 and two equivalents of Li(Indenyl). $^1$H NMR δ 7.53 (m, 2H, Indenyl), 7.32 (m, 2H, Indenyl), 7.24 (m, 4H, Indenyl), 6.45 (broad m, 2H, Indenyl), 6.45 (m, 2H, Indenyl), 6.14 (broad, 2H, Indenyl), 1.18 (d, J$^3_{PH}$=11.9 Hz, 27H, t-Bu). $^{13}$C{$^1$H} NMR δ 124.68, 124.58, 123.53, 123.38, 115.55, 96.37, 41.50 (d, J$^1_{PC}$=44.1 Hz, PCMe$_3$), 29.53. $^{31}$P{$^1$H} NMR δ 44.08. The $^1$H NMR data infer the presence of both an 5 and an $\eta^1$ bound indenyl ligand as the overlapping resonances accounting for 14 protons give rise to six signals. These NMR features of 8 are invariant with temperature even on heating solutions of 8 to 80° C. Crystallographic study of 8 (FIG. 2) confirmed the interpretation of the NMR data and the presence of $\eta^5$ and $\eta^1$ bound indenyl ligands. The Ti—N and Ti—Cl distances in 8 are 1.775(2) Å and 2.2947(10) Å respectively. The Ti—C distance for the $\eta^1$-indenyl ligand is 2.229(3) Å. This distance is slightly longer than the σ-Ti—C found in 5, consistent with the greater steric demands of the indenyl ligands.

Synthesis of CD(Indenyl)Ti(NP-t-Bu$_3$)Cl (9)

The synthesis of complex 9 is similar to that of 7. Complex 4 (0.500 g; 1.11 mmol) and NaCp.DME (0.160 g; 1.09 mmol) afford dark red crystalline 9 (0.465 g; 0.973 mmol; 88%). Alternatively, complex 9 can be synthesized from 1 and one equivalent of Li(Indenyl). $^1$H NMR δ 8.04 (d, 1H, Indenyl), 7.72 (d, 1H, Indenyl), 7.32 (m, 2H, Indenyl), 6.85 (m, 2H, Indenyl), 6.24 (d, 1H Indenyl), 5.68 (s, 5H, Cp), 1.16 (d, J$^3_{PH}$=13.4 Hz, 27H, P$^t$BU$_3$). $^{13}$C{$^1$H} NMR δ 147.73, 142.44, 133.19, 124.65, 122.28, 122.13, 120.97, 115.35, 113.69, 93.77, 41.55 (d, J$^1_{PC}$=44.1 Hz, PCMe$_3$), 29.52. $^{31}$P{$^1$H} NMR δ 44.44. Regardless of the synthetic route, $^1$H and $^{13}$C{$^1$H} NMR data confirm that the product 9 contains an η$^5$-cyclopentadienyl group and an η$^1$-indenyl fragment. This view was also affirmed by the results of an x-ray crystallographic study (FIG. 3). While most of the metric parameters within 9 are similar to those seen in 8, it is noteworthy that the lesser steric congestion in 8 results in a shorter Ti—C bond of 2.198(5) Å. The synthesis of 9 from 1 involves a facile nucleophilic substitution. In contrast, the path to 8 from 4 requires an η$^5$-η$^1$-indenyl ring slippage.

Synthesis of Cp$_3$Ti(NP-t-Bu$_3$) (10)

The synthesis of complex 10 is similar to that of 7. Complex 1 (0.500 g; 1.25 mmol) and excess NaCp.DME (0.401 g; 2.75 mmol) afford dark red crystalline 10 (0.510 g; 1.11 mmol; 89%). $^1$H NMR δ 6.03 (s, 15H, Cp), 1.13 (d, J$^3_{PH}$=13.1 Hz, 27H, PtBu$_3$). $^{13}$C{$^1$H} NMR δ 114.57, 42.00 (d, J$^1_{PC}$=46.6 Hz, PCMe$_3$), 30.50. $^{31}$P{$^1$H} NMR δ 37.48. $^1$H and $^{13}$C{$^1$H} NMR spectra show single resonances at 6.03 and 114.57 ppm, respectively, which are attributable to the cyclopentadienyl ligands. Cooling to −80° C., reveals no change in these resonances, suggesting a rapid process of site exchange. It should be noted that the presence of three η$^5$-cyclopentadienyl ligands can not specifically be excluded although this proposition is unlikely for both steric and electronic reasons. An x-ray crystallographic analysis of 10 (FIG. 4) reveals that the molecule contains two η$^5$- and one η$^1$-cyclopentadienyl groups in the solid state.

Synthesis of (Indenyl)$_3$Ti(NP-t-Bu$_3$) (11)

The synthesis of complex 11 is similar to that of 7. Complex 4 (0.500 g; 1.11 mmol) and excess Li(Indenyl) (0.300 g; 2.46 mmol) afford dark red crystalline 11 (0.640 g; 1.05 mmol; 95%). Alternatively, complex 11 can be synthesized from 6 and three equivalents of Li(Indenyl). $^1$H NMR δ 7.45 (broad m, 6H, Indenyl), 7.18 (m, 6H, Indenyl), 6.29 (t, 3H, Indenyl), 5.53 (broad, 6H, Indenyl), 0.95 (d, J$^3_{PH}$=13.5 Hz, 27H; P$^t$Bu$_3$). $^{13}$C{$^1$H} NMR δ 123.24, 41.35 (d, J$^1_{PC}$=44.0 Hz, PCMe$_3$), 15.53. $^{31}$P{$^1$H} NMR δ 44.08. The $^1$H NMR data show four resonances at 25° C., which sharpen on heating, again inferring the type of η$^5$-η$^1$-site exchange process discussed above. On cooling to 80° C. eighteen resonances are observed, inferring the presence of inequivalent η$^5$- and η$^1$-indenyl rings. The precise assessment of the exchange barrier is a complicated issue as the exchange process appears to involve three sites for each of seven protons. Consequently, the coalescence of resonances can not be unambiguously observed, although it appears that coalescence of the resonances in the $^1$H NMR spectra of 11 occurs at approximately −25° C. This infers an approximate barrier to η$^5$- and η$^1$-indenyl site exchange of 8–9 Kcal/mol. An x-ray crystallographic study of 11 confirmed that this species in the solid state contains a single η$^5$- and two η$^1$-indenyl ligands. The average Ti—N (1.780(6) Å) in 11 are similar to those seen in 5, 8 and 9, while the average Ti—C are slightly longer (Ti—C$_{avg}$ 2.215(7) Å) although not as long as those seen in 10. Whilst not wishing to be bound by theory, it is presumably the greater steric demands of the indenyl ligands that preclude the binding of two of such ligands in η$^5$-manner.

Synthesis of Cp(Indenyl)$_2$Ti(NP-t-Bu$_3$) (12)

Complex 1 (0.500 g, 1.25 mmol) and Li(Indenyl) (0.366 g, 3.00 mmol) were combined as solids and toluene (25 mL) was added. The reaction was allowed to stir for 72 hours and then was filtered and concentrated in vacuo. Heptane was then added slowly and the product crystallized as a dark red solid (0.407 g; 0.728 mmol; 58%). $^1$H NMR δ 7.78 (m, 4H; Indenyl), 7.22 (m, 4H; Indenyl), 6.67 (m, 2H; Indenyl), 6.24 (m, 4H; Indenyl), 5.53 (s, 5H; Cp), 0.92 (d, J$^3_{PH}$=13.3 Hz; 27H; P$^t$Bu$_3$). The $^1$H NMR data show four resonances inferring the presence of an η$^5$-cyclopentadienyl and two η$^1$-indenyl ligands. This interpretation was confirmed crystallographically for the solid state. The metric parameters are unexceptional as they mimic those observed for 5, 8, 9 and 11. In contrast to 11, compound 12 appears to be a rigid molecule in which there is no interchange of η$^5$-cyclopentadienyl and the two η$^1$-indenyl ligands.

X-Ray Data Collection and Reduction

X-ray quality crystals of 5, 8–12 were obtained directly from the preparation as described above. The crystals were manipulated and mounted in capillaries in a glove box, thus maintaining a dry, O$_2$-free environment for each crystal. Diffraction experiments were performed on a diffractometer (Siemens SMART System CCD) collecting a hemisphere of data in 1329 frames with 10 second exposure times. Crystal data are summarized in Table 1. The observed extinctions were consistent with the space groups in each case. The data sets were collected (4.5°<2θ<45–50.0°). A measure of decay was obtained by re-collecting the first 50 frames of each data set. The intensities of reflections within these frames showed essentially no statistically significant change over the duration of the data collections. The data were processed using a conventional data processing package in particular, using software known as SAINT and XPREP. An empirical absorption correction based on redundant data was applied to each data set. Additional solution and refinement was performed using conventional techniques (i.e. TEXSAN software solution package operating on a mainframe computer ("SGI Challenge" computers) with remote X-terminals or a personal computer employing X-emulation). The reflections with F$_o^2$>3σF$_o^2$ were used in the refinements.

Structure Solution And Refinement

Non-hydrogen atomic scattering factors were taken from the literature tabulations. The heavy atom positions were determined using direct methods (with software known as SHELX-TL). The remaining non-hydrogen atoms were located from successive difference Fourier map calculations. The refinements were carried out by using full-matrix least squares techniques on F, minimizing the function ω(|F$_o$|−|F$_c$|)$^2$ where the weight ω is defined as 4F$_o^2$/2σ(F$_o^2$) and F$_o$ and F$_c$ are the observed and calculated structure factor amplitudes. In the final cycles of each refinement, all non-hydrogen atoms were assigned anisotropic temperature factors. Carbon bound hydrogen atom positions were calculated and allowed to ride on the carbon to which they are bonded assuming a C—H bond length of 0.95 Å. Hydrogen atom temperature factors were fixed at 1.10 times the isotropic temperature factor of the carbon atom to which they are bonded. The hydrogen atom contributions were calculated, but not refined. The locations of the largest peaks in the final difference Fourier map calculation as well as the magnitude of the residual electron densities in each case were of no chemical significance.

X-ray crystallography data which further characterize the above described complexes are provided in the accompanying tables.

PART B: GAS PHASE POLYMERIZATION

Catalyst Preparation and Polymerization Testing Using a Semi-Batch, Gas Phase Reactor Standard Schlenk and drybox techniques were used in the preparation of supported catalyst systems using the organometallic complexes from Part A. Solvents were purchased as anhydrous materials and further treated to remove oxygen and polar impurities by contact with a combination of activated alumina, molecular sieves and copper oxide on silica/alumina. Where appropriate, elemental compositions of the supported catalysts were measured by Neutron Activation analysis and a reported accuracy of ±1% (weight basis).

The supported catalysts were prepared by initially supporting a commercially available MAO on a silica support (12 weight % aluminum, based on the weight of the silica support), followed by deposition of the organometallic complex. The aiming point for the Al/Ti mole ratio was 120/1.

All the polymerization experiments described below were conducted using a semi-batch, gas phase polymerization reactor of total internal volume of 2.2 L. Reaction gas mixtures (ethylene/butene mixtures) were measured to the reactor on a continuous basis using a calibrated thermal mass flow meter, following passage through purification media as described above. Reaction pressure was set at 200° C. A predetermined mass of the catalyst sample (Table B1) was added to the reactor under the flow of the inlet gas with no pre-contact of the catalyst with any reagent, such as a catalyst activator. The catalyst was activated in-situ (in the polymerization reactor) at the reaction temperature in the presence of the monomers, using a metal alkyl complex which has been previously added to the reactor to remove adventitious impurities. Purified and rigorously anhydrous sodium chloride (160 g) was used as a catalyst dispersing agent.

The internal reactor temperature was set at 90° C. and monitored by a thermocouple in the polymerization medium and controlled to +/−1.0° C. The duration of the polymerization experiment was one hour. Following the completion of the polymerization experiment, the polymer was separated from the sodium chloride and the yield determined.

Table B1 illustrates data concerning the Al/transition metal ratios of the supported catalyst and polymer yield. Table B2 provides data which describe polymer properties.

Experiments 1–3 are inventive. Experiment 4, using titanocene dichloride ($Cp_2TiCl_2$) is comparative. Titanocene dichloride is substantially less active than the inventive complexes. This is an unusual and surprising result. Whilst not wishing to be bound by theory, the experimental results suggests that the MAO (which is a Lewis acid) does not preferentially/completely abstract the phosphinimide ligand of the inventive complexes. Instead, the results strongly suggest that the MAO preferentially abstracts a Cp-type ligand from the inventive complexes. The resulting catalysts according to this invention are substantially more active than the comparative titanocene as shown in Table B1.

TABLE B2

Polymer Properties

| Example | Catalyst | Mw(*10$^{-3}$) | Mw/Mn |
|---|---|---|---|
| 1 | $Ind_2Ti(Cl)(N=Pt-Bu_3)$ | 101 | 3.7 |
| 2 | $Ind_3Ti(N=Pt-Bu_3)$ | 176 | 2.3 |
| 3 | $(Cp)(Ind_2)Ti(N=Pt-Bu_3)$ | 306 | 2.2 |

PART C: THE CONTINUOUS SOLUTION POLYMERIZATION

All the polymerization experiments described below were conducted on a continuous solution polymerization reactor. The process is continuous in all feed streams (solvent, monomers and catalyst) and in the removal of product. All feed streams were purified prior to the reactor by contact with various absorption media to remove catalyst killing impurities such as water, oxygen and polar materials as is known to those skilled in the art. All components were stored and manipulated under an atmosphere of purified nitrogen.

All the examples below were conducted in a reactor of 71.5 cc internal volume. In each experiment the volumetric feed to the reactor was kept constant and as a consequence so was the reactor residence time.

The catalyst solutions were pumped to the reactor independently and in some cases were mixed before entering the polymerization reactor (as indicated in the examples). Because of the low solubility of the catalysts, activators and MAO in cyclohexane, solutions were prepared in purified xylene. The catalyst was activated in-situ (in the polymerization reactor) at the reaction temperature in the presence of the monomers. The polymerizations were carried out in cyclohexane at a pressure of 1500 psi. Ethylene was supplied to the reactor by a calibrated thermal mass flow meter and was dissolved in the reaction solvent prior to the polymerization reactor. If comonomer (for example 1-octene) was used it was also premixed with the ethylene before entering the polymerization reactor. Under these conditions the ethylene conversion is a dependent variable controlled by the catalyst concentration, reaction temperature and catalyst activity, etc.

The internal reactor temperature is monitored by a thermocouple in the polymerization medium and can be controlled at the required set point to +/−0.5° C. Down stream of the reactor the pressure was reduced from the reaction pressure (1500 psi) to atmospheric. The solid polymer was then recovered as a slurry in the condensed solvent and was dried by evaporation before analysis.

The ethylene conversion was determined by a dedicated on line gas chromatograph by reference to propane which

TABLE B1

Polymerization Results

| | Complex | mmol Complex | Support[1] | mg of Catalyst | Yield | gPe/g Metal | gPe/g Catalyst | Al/Ti Ratio |
|---|---|---|---|---|---|---|---|---|
| 1 | $Ind_2Ti(Cl)(N=Pt-Bu_3)$ | 0.037 | 1 g | 20 | 35 | 1296242 | 4375 | 120 |
| 2 | $Ind_3Ti(N=Pt-Bu_3)$ | 0.037 | 1 g | 23 | 40 | 1185136 | 4000 | 120 |
| 3 | $(Cp)(Ind_2)Ti(N=Pt-Bu_3)$ | 0.037 | 1 g | 21 | 30 | 987613 | 3333 | 120 |
| 4 | $Cp_2TiCl_2$ | 0.037 | 1 g | 63 | 1.3 | 11648 | 21 | 120 |

[1]Support is Silica impregnated with MAO (12 wt. % Al)
[2]Ethylene-Butene Copolymerization (Co) 4 mol. % 1-Butene
[3]Pe = Polyethylene was used as an internal standard. The average polymerization rate constant was calculated based on the reactor hold-up time, the catalyst concentration in the reactor and the ethylene conversion and is expressed in l/(mmol*min).

Average polymerization rate (kp)=(Q/(100-Q))×(1/[TM])×(1/HUT)

where: Q is the percent ethylene conversion;
[TM] is the catalyst concentration in the reactor expressed in mM; and
HUT is the reactor hold-up time in minutes.

Polymer Analysis

Melt index (MI) measurements were conducted according to ASTM method D-1238-82.

Polymer densities were measured on pressed plaques (ASTM D-1928-90) with a densitometer.

Polymerization and polymer data for the following examples are shown in Table C1.

EXAMPLE 1

CpTiNP($^t$Bu)$_3$Ind$_2$ was added to the reactor at $2.3 \times 10^{-6}$ mol/l along with Ph$_3$C B(C$_6$F$_5$)$_4$ (Asahi Glass) at B/Ti=1.00 (mol/mol). The two components were mixed in the polymerization reactor. The reaction temperature was 160° C. and 2.1 gram/min of ethylene was continuously added to the reactor. An ethylene conversion of 98.7% was observed.

EXAMPLE 2

CpTiNP($^t$Bu)$_3$Ind$_2$ was added to the reactor at $9.3 \times 10^{-6}$ mol/l along with B(C$_6$F$_5$)$_3$ (Boulder Scientific) at B/Ti=2.00 (mol/mol). The two components were mixed before the polymerization reactor. The reaction temperature was 160° C. and 2.1 gram/min of ethylene was continuously added to the reactor. An ethylene conversion of 43.0% was observed.

EXAMPLE 3

CpTiNP($^t$Bu)$_3$Ind$_2$ was added to the reactor at $9.3 \times 10^{-6}$ mol/l along with B(C$_6$F$_5$)$_3$ (Boulder Scientific) at B/Ti=1.00 (mol/mol). The two components were mixed before the polymerization reactor. The reaction temperature was 160° C. and 2.1 gram/min of ethylene was continuously added to the reactor. An ethylene conversion of 45.6% was observed.

EXAMPLE 4

CpTiNP($^t$Bu)$_3$Ind$_2$ was added to the reactor at $2.3 \times 10^{-6}$ mol/l along with Ph$_3$C B(C$_6$F$_5$)$_4$ (Asahi Glass) at B/Ti=1.00 (mol/mol) and MMAO-7 (Akzo-Nobel) Al/Ti=100. The three components were mixed in the polymerization reactor. The reaction temperature was 160° C. and 2.1 gram/min of ethylene was continuously added to the reactor. An ethylene conversion of 89.4% was observed.

EXAMPLE 5

CpTiNP($^t$Bu)$_3$Ind$_2$ was added to the reactor at $9.3 \times 10^{-6}$ mol/l along with B(C$_6$F$_5$)$_3$ (Boulder Scientific) at B/Ti=2.00 (mol/mol). The two components were mixed in the polymerization reactor. The reaction temperature was 160° C. and 2.1 gram/min of ethylene was continuously added to the reactor. An ethylene conversion of 83.3% was observed.

EXAMPLE 6

CpTiNP($^t$Bu)$_3$Ind$_2$ was added to the reactor at $2.3 \times 10^{-6}$ mol/l along with MMAO-7 (Akzo-Nobel) at Al/Ti=80.0 (mol/mol). The two components were mixed in the polymerization reactor. The reaction temperature was 160° C. and 2.1 gram/min of ethylene was continuously added to the reactor. An ethylene conversion of 87.1% was observed.

EXAMPLE 7

CpTiNP($^t$Bu)$_3$IndCl was added to the reactor at $2.3 \times 10^{-6}$ mol/l along with MMAO-7 (Akzo-Nobel) at Al/Ti=80.0 (mol/mol). The two components were mixed in the polymerization reactor. The reaction temperature was 160° C. and 2.1 gram/min of ethylene was continuously added to the reactor. An ethylene conversion of 85.7% was observed.

EXAMPLE 8

CpTiNP($^t$Bu)$_3$IndCl was added to the reactor at $2.3 \times 10^{-6}$ mol/l along with B(C$_6$F$_5$)$_3$ (Boulder Scientific) at B/Ti=2.00 (mol/mol). The two components were mixed in the polymerization reactor. The reaction temperature was 160° C. and 2.1 gram/min of ethylene was continuously added to the reactor. No ethylene conversion was observed.

EXAMPLE 9

CpTiNP($^t$Bu)$_3$IndCl was added to the reactor at $2.3 \times 10^{-6}$ mol/l along with B(C$_6$F$_5$)$_3$ (Boulder Scientific) at B/Ti=2.00 (mol/mol) and MMAO-7 (Akzo-Nobel) at Al/Ti=20.0 mol/mol. The three components were mixed in the polymerization reactor. The reaction temperature was 160° C. and 2.1 gram/min of ethylene was continuously added to the reactor. An ethylene conversion of 85.2% was observed.

COMPARATIVE EXAMPLE 10C (C$_5$Me$_5$)$_2$ZrCl$_2$ (Strem) was added to the reactor at $37 \times 10^{-6}$ mol/l along with MMAO-3 (Akzo-Nobel, Al/Ti=400 mol/mol). The reaction temperature was 140° C. and 1.0 gram/min of ethylene was continuously added to the reactor. An ethylene conversion of 55.5% was observed.

COMPARATIVE EXAMPLE 11C

Cp$_2$TiCl$_2$ was used with MAO activator. This titanocene dichloride is not very active under solution polymerization conditions similar to those described in the inventive examples, although a small amount of low molecular weight polymer was recovered.

TABLE C1

| Example | Total Flow to Reactor (ml/min) | Catalyst Concentration (mol × 10$^6$) | Ethylene Conversion (%) | Calculated Polymerization Rate (kp) (l/mmol × min) | Polymer Density (g/cc) | Polymer Melt Index | Mn × 10$^{-3}$ | Mw × 10$^{-3}$ |
|---|---|---|---|---|---|---|---|---|
| 1 | 27.0 | 2.3 | 98.7 | 12784 | — | — | — | — |
| 2 | 27.0 | 9.3 | 43.0 | 31 | — | — | — | — |

TABLE C1-continued

| Example | Total Flow to Reactor (ml/min) | Catalyst Concentration (mol × 10$^6$) | Ethylene Conversion (%) | Calculated Polymerization Rate (kp) (l/mmol × min) | Polymer Density (g/cc) | Polymer Melt Index | Mn × 10$^{-3}$ | Mw × 10$^{-3}$ |
|---|---|---|---|---|---|---|---|---|
| 3 | 27.0 | 9.3 | 45.6 | 34 | — | — | — | — |
| 4 | 27.0 | 2.3 | 89.4 | 1377 | — | — | — | — |
| 5 | 27.0 | 9.3 | 83.3 | 203 | — | — | — | — |
| 6 | 27.0 | 2.3 | 87.1 | 1103 | — | — | — | — |
| 7 | 27.0 | 2.3 | 85.7 | 979 | — | — | — | — |
| 8 | 27.0 | 2.3 | 0.0 | 0. | — | — | — | — |
| 9 | 27.0 | 2.3 | 85.2 | 936 | — | — | — | — |
| 10C | 27.0 | 37.0 | 55.5 | 13 | — | 880 | 2.7 | 10.0 |
| 11C | 27.0 | 37.0 | 35.6 | 6 | — | — | 1.8 | 7.5 |

Characterization of Organometallic Complexes

Crystallographic Data for (Indenyl) Ti(NP-t-Bu$_3$)Me$_2$ (5)

TABLE 1

Crystal Data and Structure Refinement

| | |
|---|---|
| Empirical formula | C23H40NPTi |
| Formula weight | 409.43 |
| Temperature | 293(2) K |
| Wavelength | 0.71073 A |
| Crystal system | orthorhombic |
| Space group | P2(1)2(1)2(1) |
| Unit Cell Dimensions | |
| a 8.3256(11) A | alpha 90o |
| b 9.9880(10) A | beta 90o |
| c 29.100(5) A | gamma 90o |
| Volume, Z | 2419.8(6) A3, 4 |
| Density (calculated) | 1.124 Mg/m3 |
| Absorption coefficient | 0.426 mm−1 |
| Crystal size | 0.22 × 0.21 × 0.18 mm |
| q range for data collection | 1.40 to 25.00o |
| Limiting indices | −11 < h < 7, −13 < k < 13, −38 < I < 38 |
| Reflections collected | 12714 |
| Independent reflections | 4242 (Rint = 0.0241) |
| Refinement method | Full-matrix least-squares on F2 |
| Data/restraints/parameters | 4238/0/235 |
| Goodness-of-fit on F2 | 0.752 |
| Final R indices [I > 2σ(I)] | R1 = 0.0285, wR2 = 0.0870 |
| R indices (all data) | R1 = 0.0324, wR2 = 0.0921 |
| Absolute structure parameter | −0.02(2) |
| Largest diff. peak and hole | 0.154 and −0.181 eA-3 |

TABLE 2

Atomic Coordinates [×10$^4$] and Equivalent Isotropic Displacement Parameters [A$^2$ × 10$^3$]

| | x | y | z | U(eq) |
|---|---|---|---|---|
| Ti(1) | 6153(1) | 3957(1) | 1059(1) | 41(1) |
| P(1) | 7535(1) | 1171(1) | 1576(1) | 35(1) |
| N(1) | 6905(2) | 2481(2) | 1327(1) | 44(1) |
| C(1) | 4797(4) | 3074(2) | 408(1) | 65(1) |
| C(2) | 6397(4) | 3247(3) | 289(1) | 76(1) |
| C(3) | 6746(3) | 4614(3) | 276(1) | 71(1) |
| C(4) | 5300(3) | 5317(3) | 361(1) | 54(1) |
| C(5) | 4087(3) | 4364(2) | 439(1) | 53(1) |
| C(6) | 4886(4) | 6709(3) | 385(1) | 69(1) |
| C(7) | 3331(4) | 7055(3) | 469(1) | 80(1) |
| C(8) | 2160(4) | 6103(3) | 536(1) | 78(1) |
| C(9) | 2483(4) | 4772(3) | 525(1) | 68(1) |
| C(9) | 7964(4) | 5386(3) | 1227(1) | 76(1) |
| C(10) | 4306(4) | 4610(3) | 1509(1) | 79(1) |
| C(11) | 5740(3) | 107(2) | 1729(1) | 55(1) |
| C(12) | 6156(4) | −1358(2) | 1863(1) | 81(1) |
| C(13) | 4584(3) | 123(3) | 1316(1) | 79(1) |

TABLE 2-continued

Atomic Coordinates [×10$^4$] and Equivalent Isotropic Displacement Parameters [A$^2$ × 10$^3$]

| | x | y | z | U(eq) |
|---|---|---|---|---|
| C(14) | 4813(3) | 760(3) | 2126(1) | 69(1) |
| C(15) | 8941(3) | 236(2) | 1177(1) | 46(1) |
| C(16) | 10039(3) | 1265(3) | 935(1) | 63(1) |
| C(17) | 7956(3) | −441(3) | 794(1) | 66(1) |
| C(18) | 9974(3) | −837(2) | 1415(1) | 63(1) |
| C(19) | 8644(3) | 1704(2) | 2115(1) | 48(1) |
| C(20) | 7712(3) | 2857(3) | 2338(1) | 64(1) |
| C(21) | 8886(4) | 569(3) | 2464(1) | 73(1) |
| C(22) | 10278(3) | 2287(3) | 1985(1) | 67(1) |

TABLE 3

Selected Bond Lengths [A] and Angles [o]

| | | | |
|---|---|---|---|
| Ti(1)-N(1) | 1.782(2) | C(1)-C(2)-Ti(1) | 73.56(14) |
| Ti(1)-C(10) | 2.123(3) | C(4)-C(5) | 1.406(3) |
| Ti(1)-C(9) | 2.133(3) | C(4)-C(6) | 1.433(4) |
| Ti(1)-C(2) | 2.360(2) | C(5)-C(9) | 1.419(4) |
| Ti(1)-C(1) | 2.375(2) | C(6)-C(7) | 1.363(5) |
| Ti(1)-C(3) | 2.422(2) | C(7)-C(8) | 1.376(4) |
| Ti(1)-C(5) | 2.526(2) | C(8)-C(9) | 1.357(4) |
| Ti(1)-C(4) | 2.544(2) | C(11)-C(14) | 1.534(4) |
| P(1)-N(1) | 1.585(2) | C(11)-C(13) | 1.539(4) |
| P(1)-C(11) | 1.887(2) | C(11)-C(12) | 1.554(3) |
| P(1)-C(15) | 1.895(2) | C(15)-C(18) | 1.539(3) |
| P(1)-C(19) | 1.895(2) | C(15)-C(17) | 1.540(3) |
| C(1)-C(2) | 1.387(4) | C(15)-C(16) | 1.546(3) |
| C(1)-C(5) | 1.419(3) | C(19)-C(22) | 1.527(3) |
| C(2)-C(3) | 1.397(4) | C(19)-C(20) | 1.533(3) |
| C(3)-C(4) | 1.416(4) | C(19)-C(21) | 1.536(3) |
| N(1)-Ti(1)-C(10) | 103.78(10) | C(3)-C(2)-Ti(1) | 75.50(2) |
| N(1)-Ti(1)-C(9) | 101.83(9) | C(2)-C(3)-C(4) | 107.60(3) |
| C(10)-Ti(1)-C(9) | 99.50(13) | C(2)-C(3)-Ti(1) | 70.60(2) |
| N(1)-Ti(1)-C(2) | 97.87(9) | C(4)-C(3)-Ti(1) | 78.24(13) |
| C(10)-Ti(1)-C(2) | 137.78(11) | C(5)-C(4)-C(3) | 107.6(2) |
| C(9)-Ti(1)-C(2) | 111.02(13) | C(5)-C(4)-C(6) | 118.5(3) |
| N(1)-Ti(1)-C(1) | 102.05(8) | C(3)-C(4)-C(6) | 133.9(3) |
| C(10)-Ti(1)-C(1) | 105.16(12) | C(5)-C(4)-Ti(1) | 73.20(12) |
| C(9)-Ti(1)-C(1) | 140.15(11) | C(3)-C(4)-Ti(1) | 68.74(13) |
| C(2)-Ti(1)-C(1) | 34.08(11) | C(6)-C(4)-Ti(1) | 123.1(2) |
| N(1)-Ti(1)-C(3) | 124.38(10) | C(4)-C(5)-C(1) | 107.8(2) |
| C(10)-Ti(1)-C(3) | 130.16(11) | C(4)-C(5)-C(9) | 120.6(2) |
| C(9)-Ti(1)-C(3) | 83.73(12) | C(1)-C(5)-C(9) | 131.6(2) |
| C(2)-Ti(1)-C(3) | 33.94(11) | C(4)-C(5)-Ti(1) | 74.60(13) |
| C(1)-Ti(1)-C(3) | 56.45(10) | C(1)-C(5)-Ti(1) | 67.40(13) |
| N(1)-Ti(1)-C(5) | 133.22(8) | C(9)-C(5)-Ti(1) | 124.1(2) |
| C(10)-Ti(1)-C(5) | 84.15(10) | C(7)-C(6)-C(4) | 118.9(3) |
| C(9)-Ti(1)-C(5) | 122.55(9) | C(6)-C(7)-C(8) | 121.6(3) |
| C(2)-Ti(1)-C(5) | 55.12(10) | C(9)-C(8)-C(7) | 122.2(3) |
| C(1)-Ti(1)-C(5) | 33.49(10) | C(8)-C(9)-C(5) | 118.2(3) |
| C(3)-Ti(1)-C(5) | 54.77(8) | C(14)-C(11)-C(13) | 105.6(2) |

TABLE 3-continued

Selected Bond Lengths [A] and Angles [o]

| | | | |
|---|---|---|---|
| N(1)-Ti(1)-C(4) | 152.80(9) | C(14)-C(11)-C(12) | 108.8(2) |
| C(10)-Ti(1)-C(4) | 97.24(8) | C(13)-C(11)-C(12) | 110.2(2) |
| C(9)-Ti(1)-C(4) | 91.35(10) | C(14)-C(11)-P(1) | 109.7(2) |
| C(2)-Ti(1)-C(4) | 55.00(10) | C(13)-C(11)-P(1) | 107.8(2) |
| C(1)-Ti(1)-C(4) | 55.18(9) | C(12)-C(11)-P(1) | 114.4(2) |
| C(3)-Ti(1)-C(4) | 33.02(9) | C(18)-C(15)-C(17) | 108.5(2) |
| C(5)-Ti(1)-C(4) | 32.20(8) | C(18)-C(15)-C(16) | 109.7(2) |
| N(1)-P(1)-C(11) | 108.07(10) | C(17)-C(15)-C(16) | 106.1(2) |
| N(1)-P(1)-C(15) | 109.30(9) | C(18)-C(15)-P(1) | 114.4(2) |
| C(11)-P(1)-C(15) | 110.85(10) | C(17)-C(15)-P(1) | 109.3(2) |
| N(1)-P(1)-C(19) | 107.96(9) | C(16)-C(15)-P(1) | 108.48(14) |
| C(11)-P(1)-C(19) | 110.44(11) | C(22)-C(19)-C(20) | 105.7(2) |
| C(15)-P(1)-C(19) | 110.13(10) | C(22)-C(19)-C(21) | 109.2(2) |
| P(1)-N(1)-Ti(1) | 178.38(11) | C(20)-C(19)-C(21) | 109.9(2) |
| C(2)-C(1)-C(5) | 107.60(2) | C(22)-C(19)-P(1) | 109.7(2) |
| C(2)-C(1)-Ti(1) | 72.40(2) | C(20)-C(19)-P(1) | 108.3(2) |
| C(5)-C(1)-Ti(1) | 79.11(13) | C(21)-C(19)-P(1) | 113.8(2) |
| C(1)-C(2)-C(3) | 109.20(3) | | |

TABLE 4

Anisotropic Displacement Parameters [A² × 10³]

| | U11 | U22 | U33 | U23 | U13 | U12 |
|---|---|---|---|---|---|---|
| Ti(1) | 47(1) | 42(1) | 36(1) | 0(1) | -1(1) | 6(1) |
| P(1) | 32(1) | 36(1) | 36(1) | 1(1) | 2(1) | -1(1) |
| N(1) | 47(1) | 45(1) | 39(1) | 1(1) | -2(1) | 3(1) |
| C(1) | 97(2) | 54(1) | 44(1) | -6(1) | -23(1) | 9(1) |
| C(2) | 103(2) | 91(2) | 35(1) | -6(1) | -1(1) | 39(2) |
| C(3) | 68(2) | 104(2) | 40(1) | 15(1) | 11(1) | 7(2) |
| C(4) | 61(1) | 62(1) | 37(1) | 11(1) | -6(1) | 0(1) |
| C(5) | 64(2) | 57(1) | 37(1) | 2(1) | -13(1) | 0(1) |
| C(6) | 88(2) | 57(1) | 62(2) | 11(1) | -19(2) | -11(1) |
| C(7) | 111(3) | 59(2) | 69(2) | 1(1) | -19(2) | 25(2) |
| C(8) | 70(2) | 90(2) | 74(2) | 3(2) | -9(1) | 21(2) |
| C(9) | 59(1) | 81(2) | 64(2) | 8(1) | -16(1) | -3(2) |
| C(9) | 87(2) | 51(1) | 91(2) | 12(1) | -16(2) | -12(1) |
| C(10) | 80(2) | 108(2) | 49(1) | -6(1) | 4(1) | 40(2) |
| C(11) | 42(1) | 51(1) | 71(2) | 6(1) | 13(1) | -9(1) |
| C(12) | 74(2) | 54(1) | 115(2) | 19(1) | 28(2) | -13(1) |
| C(13) | 40(1) | 96(2) | 102(2) | -9(2) | -5(1) | -21(1) |
| C(14) | 51(1) | 77(2) | 81(2) | 12(1) | 28(1) | 0(1) |
| C(15) | 45(1) | 45(1) | 46(1) | -8(1) | 12(1) | 1(1) |
| C(16) | 56(1) | 67(2) | 64(2) | 3(1) | 24(1) | -4(1) |
| C(17) | 72(2) | 72(2) | 54(1) | -19(1) | 4(1) | -6(1) |
| C(18) | 56(1) | 54(1) | 79(2) | -4(1) | 12(1) | 11(1) |
| C(19) | 49(1) | 54(1) | 41(1) | -7(1) | -6(1) | 7(1) |
| C(20) | 68(2) | 71(2) | 52(1) | -21(1) | -5(1) | 10(1) |
| C(21) | 81(2) | 86(2) | 51(1) | 9(1) | -9(1) | 20(2) |
| C(22) | 45(1) | 74(2) | 81(2) | -22(1) | -13(1) | -3(1) |

TABLE 5

Hydrogen Coordinates (×10⁴) and Isotropic Displacement Parameters (A² × 10³)

| | x | y | z | U(eq) |
|---|---|---|---|---|
| H(1A) | 4210(1) | 3957(1) | 1059(1) | 41(1) |
| H(2A) | 7113(1) | 1171(1) | 1576(1) | 35(1) |
| H(3A) | 7755(2) | 2481(2) | 1327(1) | 44(1) |
| H(6A) | 5667(4) | 3074(2) | 408(1) | 65(1) |
| H(7A) | 3055(4) | 3247(3) | 289(1) | 76(1) |
| H(8A) | 1111(3) | 4614(3) | 276(1) | 71(1) |
| H(9A) | 1675(3) | 5317(3) | 361(1) | 54(1) |
| H(9B) | 8907(3) | 4364(2) | 439(1) | 53(1) |
| H(9C) | 8226(4) | 6709(3) | 385(1) | 69(1) |
| H(9D) | 7575(4) | 7055(3) | 469(1) | 80(1) |
| H(10A) | 3380(4) | 6103(3) | 536(1) | 78(1) |
| H(10B) | 4026(4) | 4772(3) | 525(1) | 68(1) |
| H(10C) | 4677(4) | 5386(3) | 1227(1) | 76(1) |

TABLE 5-continued

Hydrogen Coordinates (×10⁴) and Isotropic Displacement Parameters (A² × 10³)

| | x | y | z | U(eq) |
|---|---|---|---|---|
| H(12A) | 6737(4) | 4610(3) | 1509(1) | 79(1) |
| H(12B) | 5183(3) | 107(2) | 1729(1) | 55(1) |
| H(12C) | 6807(4) | -1358(2) | 1863(1) | 81(1) |
| H(13A) | 5102(3) | 123(3) | 1316(1) | 79(1) |
| H(13B) | 4295(3) | 760(3) | 2126(1) | 69(1) |
| H(13C) | 3625(#) | 236(2) | 1177(1) | 46(1) |
| H(14A) | 54799(3) | 1265(3) | 935(1) | 63(1) |
| H(14B) | 3860(3) | -441(3) | 794(1) | 66(1) |
| H(14C) | 4521(3) | -837(2) | 1415(1) | 63(1) |
| H(16A) | 9390(3) | 1704(2) | 2115(1) | 48(1) |
| H(16B) | 10683(3) | 2857(3) | 2338(1) | 64(1) |
| H(16C) | 10725(4) | 569(3) | 2464(1) | 73(1) |
| H(17A) | 7305(3) | 2287(3) | 1985(1) | 67(1) |
| H(17B) | 7277(3) | 2857(3) | 2338(1) | 64(1) |
| H(17C) | 8671(4) | 569(3) | 2464(1) | 73(1) |
| H(18A) | 10596(3) | 2287(3) | 1985(1) | 67(1) |
| H(18B) | 10682(3) | 2857(3) | 2338(1) | 64(1) |
| H(18C) | 9289(4) | 569(3) | 2464(1) | 73(1) |
| H(20A) | 6666(3) | 2548(3) | 1985(1) | 67(1) |
| H(20B) | 7603(3) | 3578(3) | 2338(1) | 64(1) |
| H(20C) | 8282(4) | 3167(3) | 2464(1) | 73(1) |
| H(21A) | 7862(3) | 200(3) | 1985(1) | 67(1) |
| H(21B) | 9406(3) | 916(3) | 2338(1) | 64(1) |
| H(21C) | 9542(4) | -118(3) | 2464(1) | 73(1) |
| H(22A) | 10921(3) | 1605(3) | 1985(1) | 67(1) |
| H(22B) | 10810(3) | 2606(3) | 2338(1) | 64(1) |
| H(22C) | 10131(4) | 3016(3) | 2464(1) | 73(1) |

Crystallographic Data for $Cp_3Ti(NP\text{-}t\text{-}Bu_3)$ (9)

TABLE 1

Crystal Data and Structure Refinement

| | |
|---|---|
| Empirical formula | C54H84N2P2Ti2 |
| Formula weight | 918.97 |
| Temperature | 293(2) K |
| Wavelength | 0.71073A |
| Crystal system | trinclinic |
| Space group | P-1 |
| Unit cell dimensions | |
| a 11.190(3) A | alpha 85.32(2)o |
| b 14.763(2) A | beta 73.01(2)o |
| c 16.157(3) A | gamma 82.94(2)o |
| Volume, Z | 2530.3(9) A3, 2 |
| Density (calculated) | 1.206 Mg/m3 |
| Absorption coefficient | 0.415 mm-1 |
| Crystal size | 0.34 × 0.28 × 0.25 mm |
| q range for data collection | 1.39 to 25.00o |
| Limiting indices | -14 < h < 13, -19 < k < 19, -21 < l < 14 |
| Reflections collected | 13084 |
| Independent reflections | 8539 (Rint = 0.0214) |
| Refinement method | Full-matrix least-squares on F2 |
| Data/restraints/parameters | 8536/0/541 |
| Goodness-of-fit on F2 | 0.987 |
| Final R indices [I > 2σ(I)] | R1 = 0.0396, wR2 = 0.1223 |
| R indices (all data) | R1 = 0.0471, wR2 = 0.1339 |
| Largest diff. peak and hole | 0.358 and -0.395 eA-3 |

TABLE 2

Atomic Coordinates [×10⁴] and Equivalent Isotropic Displacement Parameters [A² × 10³]

| | x | y | z | U(eq) |
|---|---|---|---|---|
| Ti(1) | 6153(1) | 3957(1) | 1059(1) | 41(1) |
| P(1) | 7535(1) | 1171(1) | 1576(1) | 35(1) |
| N(1) | 6905(2) | 2481(2) | 1327(1) | 44(1) |

TABLE 2-continued

Atomic Coordinates [×10⁴] and Equivalent Isotropic Displacement Parameters [$Å^2 \times 10^3$]

|  | x | y | z | U(eq) |
|---|---|---|---|---|
| C(1) | 4797(4) | 3074(2) | 408(1) | 65(1) |
| C(2) | 6397(4) | 3247(3) | 289(1) | 76(1) |
| C(3) | 6746(3) | 4614(3) | 276(1) | 71(1) |
| C(4) | 5300(3) | 5317(3) | 361(1) | 54(1) |
| C(5) | 4087(3) | 4364(2) | 439(1) | 53(1) |
| C(6) | 4886(4) | 6709(3) | 385(1) | 69(1) |
| C(7) | 3331(4) | 7055(3) | 469(1) | 80(1) |
| C(8) | 2160(4) | 6103(3) | 536(1) | 78(1) |
| C(9) | 2483(4) | 4772(3) | 525(1) | 68(1) |
| C(9) | 7964(4) | 5386(3) | 1227(1) | 76(1) |
| C(10) | 4306(4) | 4610(3) | 1509(1) | 79(1) |
| C(11) | 5740(3) | 107(2) | 1729(1) | 55(1) |
| C(12) | 6156(4) | −1358(2) | 1863(1) | 81(1) |
| C(13) | 4584(3) | 123(3) | 1316(1) | 79(1) |
| C(14) | 4813(3) | 760(3) | 2126(1) | 69(1) |
| C(15) | 8941(3) | 236(2) | 1177(1) | 46(1) |
| C(16) | 10039(3) | 1265(3) | 935(1) | 63(1) |
| C(17) | 7956(3) | −441(3) | 794(1) | 66(1) |
| C(18) | 9974(3) | −837(2) | 1415(1) | 63(1) |
| C(19) | 8644(3) | 1704(3) | 2115(1) | 48(1) |
| C(20) | 7712(3) | 2857(3) | 2338(1) | 64(1) |
| C(21) | 8886(4) | 569(3) | 2464(1) | 73(1) |
| C(22) | 10278(3) | 2287(3) | 1985(1) | 67(1) |

TABLE 3

Selected Bond Lengths [Å] and Angles [°]

| | |
|---|---|
| Ti(1)—N(1) | 1.782(2) |
| Ti(1)—C(9) | 2.133(3) |
| Ti(1)—C(1) | 2.375(2) |
| Ti(1)—C(5) | 2.526(2) |
| P(1)—N(1) | 1.585(2) |
| P(1)—C(15) | 1.895(2) |
| C(1)—C(2) | 1.387(4) |
| C(2)—C(3) | 1.397(4) |
| C(4)—C(5) | 1.406(3) |
| C(5)—C(9) | 1.419(4) |
| C(7)—C(8) | 1.376(4) |
| C(11)—C(14) | 1.534(4) |
| C(11)—C(12) | 1.554(3) |
| C(15)—C(17) | 1.540(3) |
| C(19)—C(22) | 1.527(3) |
| C(19)—C(21) | 1.536(3) |
| N(1)—Ti(1)—C(10) | 103.78(10) |
| N(1)—Ti(1)—C(9) | 101.83(9) |
| C(10)—Ti(1)—C(9) | 99.50(13) |
| N(1)—Ti(1)—C(2) | 97.87(9) |
| C(10)—Ti(1)—C(2) | 137.78(11) |
| C(9)—Ti(1)—C(2) | 111.02(13) |
| N(1)—Ti(1)—C(1) | 102.05(8) |
| C(10)—Ti(1)—C(1) | 105.16(12) |
| C(9)—Ti(1)—C(1) | 140.15(11) |
| C(2)—Ti(1)—C(1) | 34.08(11) |
| N(1)—Ti(1)—C(3) | 124.38(10) |
| C(10)—Ti(1)—C(3) | 130.16(11) |
| C(9)—Ti(1)—C(3) | 83.73(12) |
| C(2)—Ti(1)—C(3) | 33.94(11) |
| C(1)—Ti(1)—C(3) | 56.45(10) |
| N(1)—Ti(1)—C(5) | 133.22(8) |
| C(10)—Ti(1)—C(5) | 84.15(10) |
| C(9)—Ti(1)—C(5) | 122.55(9) |
| C(2)—Ti(1)—C(5) | 55.12(10) |
| C(1)—Ti(1)—C(5) | 33.49(8) |
| C(3)—Ti(1)—C(5) | 54.77(9) |
| N(1)—Ti(1)—C(4) | 152.80(8) |
| C(10)—Ti(1)—C(4) | 97.24(10) |
| C(9)—Ti(1)—C(4) | 91.35(10) |
| C(2)—Ti(1)—C(4) | 55.00(9) |
| C(1)—Ti(1)—C(4) | 55.18(9) |
| C(3)—Ti(1)—C(4) | 33.02(9) |
| C(5)—Ti(1)—C(4) | 32.20(8) |

TABLE 3-continued

Selected Bond Lengths [Å] and Angles [°]

| | |
|---|---|
| N(1)—P(1)—C(11) | 108.07(10) |
| N(1)—P(1)—C(15) | 109.30(9) |
| C(11)—P(1)—C(15) | 110.85(10) |
| N(1)—P(1)—C(19) | 107.96(9) |
| C(11)—P(1)—C(19) | 110.44(11) |
| C(15)—P(1)—C(19) | 110.13(10) |
| P(1)—N(1)—Ti(1) | 178.38(11) |
| C(2)—C(1)—C(5) | 107.6(2) |
| C(2)—C(1)—Ti(1) | 72.4(2) |
| C(5)—C(1)—Ti(1) | 79.11(13) |
| C(1)—C(2)—C(3) | 109.2(3) |
| C(1)—C(2)—Ti(1) | 73.56(14) |
| Ti(1)—C(10) | 2.123(3) |
| Ti(1)—C(2) | 2.360(2) |
| Ti(1)—C(3) | 2.422(2) |
| Ti(1)—C(4) | 2.544(2) |
| P(1)—C(11) | 1.887(2) |
| P(1)—C(19) | 1.895(2) |
| C(1)—C(5) | 1.419(3) |
| C(3)—C(4) | 1.416(4) |
| C(4)—C(6) | 1.433(4) |
| C(6)—C(7) | 1.363(5) |
| C(8)—C(9) | 1.357(4) |
| C(11)—C(13) | 1.539(4) |
| C(15)—C(18) | 1.539(3) |
| C(15)—C(16) | 1.546(3) |
| C(19)—C(20) | 1.533(3) |
| C(4)—C(5)—C(1) | 107.8(2) |
| C(4)—C(5)—C(9) | 120.6(2) |
| C(1)—C(5)—C(9) | 131.6(2) |
| C(4)—C(5)—Ti(1) | 74.60(13) |
| C(1)—C(5)—Ti(1) | 67.40(13) |
| C(9)—C(5)—Ti(1) | 124.1(2) |
| C(7)—C(6)—C(4) | 118.9(3) |
| C(6)—C(7)—C(8) | 121.6(3) |
| C(9)—C(8)—C(7) | 122.2(3) |
| C(8)—C(9)—C(5) | 118.2(3) |
| C(14)—C(11)—C(13) | 105.6(2) |
| C(14)—C(11)—C(12) | 108.8(2) |
| C(13)—C(11)—C(12) | 110.2(2) |
| C(14)—C(11)—P(1) | 109.7(2) |
| C(3)—C(2)—Ti(1) | 75.5(2) |
| C(2)—C(3)—C(4) | 107.6(3) |
| C(2)—C(3)—Ti(1) | 70.6(2) |
| C(4)—C(3)—Ti(1) | 78.24(13) |
| C(5)—C(4)—C(3) | 107.6(2) |
| C(5)—C(4)—C(6) | 118.5(3) |
| C(3)—C(4)—C(6) | 133.9(3) |
| C(5)—C(4)—Ti(1) | 73.20(12) |
| C(3)—C(4)—Ti(1) | 68.74(13) |
| C(6)—C(4)—Ti(1) | 123.1(2) |
| C(13)—C(11)—P(1) | 107.8(2) |
| C(12)—C(11)—P(1) | 114.4(2) |
| C(18)—C(15)—C(17) | 108.5(2) |
| C(18)—C(15)—C(16) | 109.7(2) |
| C(17)—C(15)—C(16) | 106.1(2) |
| C(18)—C(15)—P(1) | 114.4(2) |
| C(17)—C(15)—P(1) | 109.3(2) |
| C(16)—C(15)—P(1) | 108.48(14) |
| C(22)—C(19)—C(20) | 105.7(2) |
| C(22)—C(19)—C(18) | 109.2(2) |
| C(20)—C(19)—C(21) | 109.9(2) |
| C(22)—C(19)—P(1) | 109.7(2) |
| C(20)—C(19)—P(1) | 108.3(2) |
| C(21)—C(19)—P(1) | 113.8(2) |

TABLE 4

Anisotropic Displacement Parameters [$Å^2 \times 10^3$]

| | U11 | U22 | U33 | U23 | U13 | U12 |
|---|---|---|---|---|---|---|
| Ti(1) | 47(1) | 42(1) | 36(1) | 0(1) | −1(1) | 6(1) |
| P(1) | 32(1) | 36(1) | 36(1) | 1(1) | 2(1) | −1(1) |
| N(1) | 47(1) | 45(1) | 39(1) | 1(1) | −2(1) | 3(1) |

TABLE 4-continued

Anisotropic Displacement Parameters [$A^2 \times 10^3$]

|       | U11    | U22    | U33    | U23    | U13    | U12    |
|-------|--------|--------|--------|--------|--------|--------|
| C(1)  | 97(2)  | 54(1)  | 44(1)  | −6(1)  | −23(1) | 9(1)   |
| C(2)  | 103(2) | 91(2)  | 35(1)  | −6(1)  | −1(1)  | 39(2)  |
| C(3)  | 68(2)  | 104(2) | 40(1)  | 15(1)  | 11(1)  | 7(2)   |
| C(4)  | 61(1)  | 62(1)  | 37(1)  | 11(1)  | −6(1)  | 0(1)   |
| C(5)  | 64(2)  | 57(1)  | 37(1)  | 2(1)   | −13(1) | 0(1)   |
| C(6)  | 88(2)  | 57(1)  | 62(2)  | 11(1)  | −19(2) | −11(1) |
| C(7)  | 111(3) | 59(2)  | 69(2)  | 1(1)   | −19(2) | 25(2)  |
| C(8)  | 70(2)  | 90(2)  | 74(2)  | 3(2)   | −9(1)  | 21(2)  |
| C(9)  | 59(1)  | 81(2)  | 64(2)  | 8(1)   | −16(1) | −3(2)  |
| C(9)  | 87(2)  | 51(1)  | 91(2)  | 12(1)  | −16(2) | −12(1) |
| C(10) | 80(2)  | 108(2) | 49(1)  | −6(1)  | 4(1)   | 40(2)  |
| C(11) | 42(1)  | 51(1)  | 71(2)  | 6(1)   | 13(1)  | −9(1)  |
| C(12) | 74(2)  | 54(1)  | 115(2) | 19(1)  | 28(2)  | −13(1) |
| C(13) | 40(1)  | 96(2)  | 102(2) | −9(2)  | −5(1)  | −21(1) |
| C(14) | 51(1)  | 77(2)  | 81(2)  | 12(1)  | 28(1)  | 0(1)   |
| C(15) | 45(1)  | 45(1)  | 46(1)  | −8(1)  | 12(1)  | 1(1)   |
| C(16) | 56(1)  | 67(2)  | 64(1)  | 3(1)   | 24(1)  | −4(1)  |
| C(17) | 72(2)  | 72(2)  | 54(1)  | −19(1) | 4(1)   | −6(1)  |
| C(18) | 56(1)  | 54(1)  | 79(2)  | −4(1)  | 12(1)  | 11(1)  |
| C(19) | 49(1)  | 54(1)  | 41(1)  | −7(1)  | −6(1)  | 7(1)   |
| C(20) | 68(2)  | 71(2)  | 52(1)  | −21(1) | −5(1)  | 10(1)  |
| C(21) | 81(2)  | 86(2)  | 51(1)  | 9(1)   | −9(1)  | 20(2)  |
| C(22) | 45(1)  | 74(2)  | 81(2)  | −22(1) | −13(1) | −3(1)  |

TABLE 5

Hydrogen Coordinates ($\times 10^4$) and Isotropic Displacement Parameters ($A^2 \times 10^3$)

|        | x         | y        | z       | U(eq) |
|--------|-----------|----------|---------|-------|
| H(1A)  | 4210(4)   | 2224(3)  | 399(1)  | 78    |
| H(2A)  | 7113(4)   | 2535(3)  | 181(1)  | 92    |
| H(3A)  | 7755(3)   | 5012(3)  | 169(1)  | 85    |
| H(6A)  | 5667(4)   | 7364(3)  | 343(1)  | 83    |
| H(7A)  | 3055(4)   | 7957(3)  | 482(1)  | 96    |
| H(8A)  | 1111(4)   | 6382(3)  | 592(1)  | 94    |
| H(9A)  | 1675(4)   | 4144(3)  | 572(1)  | 81    |
| H(9B)  | 8907(4)   | 5216(3)  | 1046(1) | 114   |
| H(9C)  | 8226(4)   | 5314(3)  | 1547(1) | 114   |
| H(9D)  | 7575(4)   | 6272(3)  | 1163(1) | 114   |
| H(10A) | 3380(4)   | 4048(3)  | 1472(1) | 119   |
| H(10B) | 4026(4)   | 5519(3)  | 1437(1) | 119   |
| H(10C) | 4677(4)   | 4558(3)  | 1821(1) | 119   |
| H(12A) | 6737(4)   | −1775(2) | 1617(1) | 121   |
| H(12B) | 5183(4)   | −1846(2) | 1920(1) | 121   |
| H(12C) | 6807(4)   | −1358(2) | 2136(1) | 121   |
| H(13A) | 5102(3)   | −275(3)  | 1055(1) | 119   |
| H(13B) | 4295(3)   | 1030(3)  | 1246(1) | 119   |
| H(13C) | 3635(3)   | −378(3)  | 1391(1) | 119   |
| H(14A) | 5479(3)   | 780(3)   | 2395(1) | 104   |
| H(14B) | 3860(3)   | 250(3)   | 2189(1) | 104   |
| H(14C) | 4521(3)   | 1657(3)  | 2043(1) | 104   |
| H(16A) | 9390(3)   | 1933(3)  | 788(1)  | 94    |
| H(16B) | 10683(3)  | 816(3)   | 709(1)  | 94    |
| H(16C) | 10725(3)  | 1683(3)  | 1158(1) | 94    |
| H(17A) | 7305(3)   | 217(3)   | 642(1)  | 99    |
| H(17B) | 7277(3)   | −1117(3) | 926(1)  | 99    |
| H(17C) | 8671(3)   | −846(3)  | 576(1)  | 99    |
| H(18A) | 10596(3)  | −430(2)  | 1655(1) | 94    |
| H(18B) | 10682(3)  | −1239(2) | 1194(1) | 94    |
| H(18C) | 9289(3)   | −1513(2) | 1544(1) | 94    |
| H(20A) | 6666(3)   | 2548(3)  | 2428(1) | 96    |
| H(20B) | 7603(3)   | 3578(3)  | 2122(1) | 96    |
| H(20C) | 8282(3)   | 3167(3)  | 2604(1) | 96    |
| H(21A) | 7862(4)   | 200(3)   | 2547(1) | 109   |
| H(21B) | 9406(4)   | 916(3)   | 2733(1) | 109   |
| H(21C) | 9542(4)   | −118(3)  | 2330(1) | 109   |
| H(22A) | 10921(3)  | 1605(3)  | 1842(1) | 100   |
| H(22B) | 10810(3)  | 2606(3)  | 2256(1) | 100   |
| H(22C) | 10131(3)  | 3016(3)  | 1774(1) | 100   |

Crystallographic Data for (Indenyl)$_2$Ti(NP-t-Bu$_3$)Cl (7)

TABLE 1

Crystal Data and Structure Refinement

| | |
|---|---|
| Empirical formula | C33H22ClNPTi |
| Formula weight | 546.84 |
| Temperature | 293(2) K |
| Wavelength | 0.71073 A |
| Crystal system | triclinic |
| Space group | P-1 |
| Unit cell dimensions | |
| a 10.299(2) A | alpha 68.10(2)° |
| b 12.155(3) A | beta 77.06(2)° |
| c 15.071(3) A | gamma 65.95(2)° |
| Volume, Z | 1592.9(6) A3, 2 |
| Density (calculated) | 1.140 Mg/m$^3$ |
| Absorption coefficient | 0.422 mm-1 |
| Crystal size | 0.27 × 0.25 × 0.22 mm |
| q range for data collection | 1.46 to 24.99° |
| Limiting indices | −13 < h < 10, −16 < k < 16, −20 < l < 18 |
| Reflections collected | 8253 |
| Independent reflections | 5394 (Rint = 0.0205) |
| Refinement method | Full-matrix least-squares on F$^2$ |
| Data/restraints/parameters | 5379/0/327 |
| Goodness-of-fit on F2 | 1.181 |
| Final R indices [I > 2σ(I)] | R1 = 0.0525, wR2 = 0.1550 |
| R indices (all data) | R1 = 0.0682, wR2 = 0.1741 |
| Largest diff. peak and hole 0.856 and −0.335 eA-3 | |

TABLE 2

Atomic Coordinates [$\times 10^4$] and Equivalent Isotropic Displacement Parameters [$A^2 \times 10^3$]

|       | x         | y         | z        | U(eq)   |
|-------|-----------|-----------|----------|---------|
| Ti(1) | 4720(1)   | 8736(1)   | 2698(1)  | 38(1)   |
| Cl(1) | 4096(1)   | 8233(1)   | 4320(1)  | 54(1)   |
| P(1)  | 7665(1)   | 6165(1)   | 2652(1)  | 38(1)   |
| N(1)  | 6221(3)   | 7393(2)   | 2559(2)  | 42(1)   |
| C(1)  | 9105(4)   | 6492(4)   | 2975(3)  | 64(1)   |
| C(2)  | 8487(5)   | 7216(5)   | 3717(4)  | 85(1)   |
| C(3)  | 10405(5)  | 5287(4)   | 3368(4)  | 86(1)   |
| C(4)  | 9631(5)   | 7409(5)   | 2073(4)  | 98(2)   |
| C(5)  | 7303(4)   | 4777(3)   | 3629(3)  | 63(1)   |
| C(6)  | 7261(5)   | 4910(5)   | 4620(3)  | 94(2)   |
| C(7)  | 5801(4)   | 4854(4)   | 3536(4)  | 95(2)   |
| C(8)  | 8400(4)   | 3467(4)   | 3614(3)  | 77(1)   |
| C(9)  | 8181(4)   | 5835(4)   | 1476(2)  | 62(1)   |
| C(10) | 7933(5)   | 7118(5)   | 650(3)   | 92(2)   |
| C(11) | 9723(4)   | 4916(5)   | 1370(3)  | 84(1)   |
| C(12) | 7142(6)   | 5260(5)   | 1364(4)  | 100(2)  |
| C(13) | 5882(4)   | 10219(3)  | 2025(3)  | 55(1)   |
| C(14) | 4884(3)   | 10724(3)  | 2726(2)  | 47(1)   |
| C(15) | 5035(4)   | 10924(3)  | 3557(3)  | 61(1)   |
| C(16) | 3840(5)   | 11422(4)  | 4093(3)  | 72(1)   |
| C(17) | 2479(5)   | 11725(4)  | 3852(3)  | 71(1)   |
| C(18) | 2280(4)   | 11558(3)  | 3056(3)  | 58(1)   |
| C(19) | 3487(3)   | 11074(3)  | 2462(2)  | 45(1)   |
| C(20) | 3646(4)   | 10788(3)  | 1598(2)  | 52(1)   |
| C(21) | 5103(4)   | 10318(3)  | 1320(2)  | 58(1)   |
| C(22) | 3037(3)   | 8326(3)   | 2310(2)  | 52(1)   |
| C(23) | 1573(4)   | 9203(3)   | 2442(1)  | 53(1)   |
| C(24) | 726(4)    | 9437(4)   | 3263(3)  | 67(1)   |
| C(25) | −637(5)   | 10348(5)  | 3173(5)  | 86(2)   |
| C(26) | −1141(5)  | 11035(5)  | 2258(5)  | 94(2)   |
| C(27) | −337(5)   | 10801(4)  | 1451(4)  | 81(1)   |
| C(28) | 1032(4)   | 9860(4)   | 1536(3)  | 62(1)   |
| C(29) | 2079(5)   | 9357(4)   | 853(3)   | 69(1)   |
| C(30) | 3214(4)   | 8446(4)   | 1306(3)  | 63(1)   |
| C(31) | 6437(13)  | 4352(12)  | −733(9)  | 108(3)  |
| C(32) | 5829(6)   | 3961(6)   | 22(4)    | 101(2)  |
| C(33) | 5242(12)  | 3642(11)  | 753(8)   | 92(3)   |
| C(34) | 4545(11)  | 4611(10)  | 684(7)   | 83(2)   |
| C(35) | 3995(10)  | 4246(9)   | 1386(7)  | 80(2)   |

TABLE 3

Selected Bond Lengths [Å] and Angles [°]

| Bond/Angle | Value |
|---|---|
| Ti(1)—N(1) | 1.775(2) |
| Ti(1)—C(22) | 2.229(3) |
| Ti(1)—Cl(1) | 2.2947(10) |
| Ti(1)—C(21) | 2.332(3) |
| Ti(1)—C(13) | 2.357(3) |
| Ti(1)—C(20) | 2.383(3) |
| Ti(1)—C(14) | 2.506(3) |
| Ti(1)—C(19) | 2.514(3) |
| P(1)—N(1) | 1.609(3) |
| P(1)—C(9) | 1.877(3) |
| P(1)—C(1) | 1.882(4) |
| P(1)—C(5) | 1.889(4) |
| C(1)—C(2) | 1.545(5) |
| C(1)—C(3) | 1.549(5) |
| C(1)—C(4) | 1.555(6) |
| C(5)—C(8) | 1.537(5) |
| C(5)—C(7) | 1.546(6) |
| C(5)—C(6) | 1.550(6) |
| C(9)—C(11) | 1.539(5) |
| C(9)—C(10) | 1.554(6) |
| C(9)—C(12) | 1.563(6) |
| C(13)—C(21) | 1.411(5) |
| C(13)—C(14) | 1.426(5) |
| C(14)—C(15) | 1.414(5) |
| C(14)—C(19) | 1.429(4) |
| C(15)—C(16) | 1.358(6) |
| C(16)—C(17) | 1.393(6) |
| C(17)—C(18) | 1.359(5) |
| C(18)—C(19) | 1.411(5) |
| C(19)—C(20) | 1.428(5) |
| C(20)—C(21) | 1.397(5) |
| C(22)—C(30) | 1.442(5) |
| C(22)—C(23) | 1.470(5) |
| C(23)—C(24) | 1.397(5) |
| C(23)—C(28) | 1.407(5) |
| C(24)—C(25) | 1.386(6) |
| C(25)—C(26) | 1.406(8) |
| C(26)—C(27) | 1.364(7) |
| C(27)—C(28) | 1.403(6) |
| C(28)—C(29) | 1.425(6) |
| C(29)—C(30) | 1.341(6) |
| C(31)—C(32) | 1.197(12) |
| C(31)—C(34)#1 | 1.270(14) |
| C(31)—C(35)#1 | 1.55(2) |
| C(32)—C(33) | 1.141(11) |
| C(32)—C(34) | 1.585(11) |
| C(32)—C(34)#1 | 1.598(12) |
| C(33)—C(34) | 1.080(13) |
| C(33)—C(35) | 1.518(14) |
| C(34)—C(35) | 1.106(11) |
| C(34)—C(31)#1 | 1.270(14) |
| C(34)—C(32)#1 | 1.598(12) |
| C(35)—C(31)#1 | 1.55(2) |
| N(1)—Ti(1)—C(22) | 99.17(12) |
| N(1)—Ti(1)—Cl(1) | 104.63(9) |
| C(22)—Ti(1)—Cl(1) | 97.10(10) |
| N(1)—Ti(1)—C(21) | 100.72(12) |
| C(22)—Ti(1)—C(21) | 102.73(14) |
| Cl(1)—Ti(1)—C(21) | 144.67(10) |
| N(1)—Ti(1)—C(13) | 96.48(12) |
| C(22)—Ti(1)—C(13) | 137.29(13) |
| Cl(1)—Ti(1)—C(13) | 116.88(10) |
| C(21)—Ti(1)—C(13) | 35.03(13) |
| N(1)—Ti(1)—C(20) | 132.07(12) |
| C(22)—Ti(1)—C(20) | 82.84(12) |
| Cl(1)—Ti(1)—C(20) | 122.75(9) |
| C(21)—Ti(1)—C(20) | 34.46(12) |
| C(13)—Ti(1)—C(20) | 57.69(12) |
| N(1)—Ti(1)—C(14) | 124.05(11) |
| C(22)—Ti(1)—C(14) | 133.35(12) |
| Cl(1)—Ti(1)—C(14) | 88.78(8) |
| C(21)—Ti(1)—C(14) | 56.45(12) |
| C(13)—Ti(1)—C(14) | 33.92(11) |
| C(20)—Ti(1)—C(14) | 56.21(11) |
| N(1)—Ti(1)—C(19) | 152.60(11) |
| C(22)—Ti(1)—C(19) | 100.31(11) |
| Cl(1)—Ti(1)—C(19) | 91.89(8) |
| C(21)—Ti(1)—C(19) | 56.14(12) |
| C(13)—Ti(1)—C(19) | 56.25(11) |
| C(20)—Ti(1)—C(19) | 33.77(11) |
| C(14)—Ti(1)—C(19) | 33.08(10) |
| N(1)—P(1)—C(9) | 108.7(2) |
| N(1)—P(1)—C(1) | 108.9(2) |
| C(9)—P(1)—C(1) | 110.9(2) |
| N(1)—P(1)—C(5) | 108.10(14) |
| C(9)—P(1)—C(5) | 110.1(2) |
| C(1)—P(1)—C(5) | 110.2(2) |
| P(1)—N(1)—Ti(1) | 167.4(2) |
| C(2)—C(1)—C(3) | 109.1(4) |
| C(2)—C(1)—C(4) | 105.3(4) |
| C(3)—C(1)—C(4) | 108.7(4) |
| C(2)—C(1)—P(1) | 110.3(3) |
| C(3)—C(1)—P(1) | 114.1(3) |
| C(4)—C(1)—P(1) | 109.0(3) |
| C(8)—C(5)—C(7) | 109.5(3) |
| C(8)—C(5)—C(6) | 108.3(3) |
| C(7)—C(5)—C(6) | 107.1(4) |
| C(8)—C(5)—P(1) | 114.6(2) |
| C(7)—C(5)—P(1) | 108.0(3) |
| C(6)—C(5)—P(1) | 109.1(3) |
| C(11)—C(9)—C(10) | 110.3(3) |
| C(11)—C(9)—C(12) | 108.6(4) |
| C(10)—C(9)—C(12) | 106.2(4) |
| C(11)—C(9)—P(1) | 114.3(2) |
| C(10)—C(9)—P(1) | 108.6(3) |
| C(12)—C(9)—P(1) | 108.4(3) |
| C(21)—C(13)—C(14) | 107.8(3) |
| C(21)—C(13)—Ti(1) | 71.5(2) |
| C(14)—C(13)—Ti(1) | 78.8(2) |
| C(15)—C(14)—C(13) | 133.3(3) |
| C(15)—C(14)—C(19) | 119.3(3) |
| C(13)—C(14)—C(19) | 107.4(3) |
| C(15)—C(14)—Ti(1) | 124.7(2) |
| C(13)—C(14)—Ti(1) | 67.3(2) |
| C(19)—C(14)—Ti(1) | 73.8(2) |
| C(16)—C(15)—C(14) | 118.7(3) |
| C(15)—C(16)—C(17) | 121.9(4) |
| C(18)—C(17)—C(16) | 121.5(4) |
| C(17)—C(18)—C(19) | 118.8(3) |
| C(18)—C(19)—C(20) | 132.7(3) |
| C(18)—C(19)—C(14) | 119.6(3) |
| C(20)—C(19)—C(14) | 107.6(3) |
| C(18)—C(19)—Ti(1) | 122.5(2) |
| C(20)—C(19)—Ti(1) | 68.1(2) |
| C(14)—C(19)—Ti(1) | 73.2(2) |
| C(21)—C(20)—C(19) | 108.0(3) |
| C(21)—C(20)—Ti(1) | 70.7(2) |
| C(19)—C(20)—Ti(1) | 78.1(2) |
| C(20)—C(21)—C(13) | 109.0(3) |
| C(20)—C(21)—Ti(1) | 74.8(2) |
| C(13)—C(21)—Ti(1) | 73.5(2) |
| C(30)—C(22)—C(23) | 103.7(3) |
| C(30)—C(22)—Ti(1) | 111.3(2) |
| C(23)—C(22)—Ti(1) | 114.7(2) |
| C(24)—C(23)—C(28) | 120.2(4) |
| C(24)—C(23)—C(22) | 131.8(4) |
| C(28)—C(23)—C(22) | 108.0(3) |
| C(25)—C(24)—C(23) | 119.4(4) |
| C(24)—C(25)—C(26) | 119.7(5) |
| C(27)—C(26)—C(25) | 121.6(4) |
| C(26)—C(27)—C(28) | 119.2(5) |
| C(27)—C(28)—C(23) | 119.8(4) |
| C(27)—C(28)—C(29) | 132.5(4) |
| C(23)—C(28)—C(29) | 107.7(3) |
| C(30)—C(29)—C(28) | 109.0(4) |
| C(29)—C(30)—C(22) | 111.3(4) |
| C(32)—C(31)—C(34)#1 | 80.6(9) |
| C(32)—C(31)—C(35)#1 | 125.5(11) |
| C(34)#1—C(31)—C(35)#1 | 44.9(6) |
| C(33)—C(32)—C(31) | 176.5(10) |
| C(33)—C(32)—C(34) | 42.9(6) |
| C(31)—C(32)—C(34) | 134.3(9) |
| C(33)—C(32)—C(34)#1 | 125.7(8) |
| C(31)—C(32)—C(34)#1 | 51.7(7) |

TABLE 3-continued

Selected Bond Lengths [A] and Angles [o]

| | |
|---|---|
| C(34)—C(32)—C(34)#1 | 82.7(6) |
| C(34)—C(33)—C(32) | 91.1(11) |
| C(34)—C(33)—C(35) | 46.7(7) |
| C(32)—C(33)—C(35) | 137.8(11) |
| C(33)—C(34)—C(35) | 88.0(11) |
| C(33)—C(34)—C(31)#1 | 168.4(13) |
| C(35)—C(34)—C(31)#1 | 81.0(10) |
| C(33)—C(34)—C(32) | 46.0(7) |
| C(35)—C(34)—C(32) | 134.0(11) |
| C(31)#1—C(34)—C(32) | 144.7(10) |
| C(33)—C(34)—C(32)#1 | 143.3(11) |
| C(35)—C(34)—C(32)#1 | 128.7(11) |
| C(31)#1—C(34)—C(32)#1 | 47.7(7) |
| C(32)—C(34)—C(32)#1 | 97.3(6) |
| C(34)—C(35)—C(33) | 45.3(7) |
| C(34)—C(35)—C(31)#1 | 54.1(8) |
| C(33)—C(35)—C(31)#1 | 99.4(8) |

TABLE 4

Anisotropic Displacement Parameters [$A^2 \times 10^3$]

| | U11 | U22 | U33 | U23 | U13 | U12 |
|---|---|---|---|---|---|---|
| TI(1) | 39(1) | 32(1) | 42(1) | −10(1) | −6(1) | −12(1) |
| Cl(1) | 64(1) | 48(1) | 45(1) | −11(1) | −1(1) | −20(1) |
| P(1) | 38(1) | 37(1) | 37(1) | −11(1) | −4(1) | −11(1) |
| N(1) | 41(1) | 38(1) | 44(1) | −12(1) | −3(1) | −13(1) |
| C(1) | 50(2) | 58(2) | 89(3) | −28(2) | −21(2) | −13(2) |
| C(2) | 90(3) | 82(3) | 104(3) | −53(2) | −40(2) | −14(2) |
| C(3) | 61(3) | 83(3) | 117(4) | −38(3) | −43(2) | −5(2) |
| C(4) | 68(3) | 76(3) | 153(5) | −29(3) | 4(3) | −42(3) |
| C(5) | 53(2) | 40(2) | 72(2) | −6(2) | 6(2) | −9(2) |
| C(6) | 100(4) | 84(3) | 47(2) | −5(2) | 14(2) | −8(3) |
| C(7) | 53(2) | 57(3) | 140(4) | 0(3) | 13(3) | −24(2) |
| C(8) | 67(3) | 39(2) | 95(3) | −10(2) | 7(2) | −6(2) |
| C(9) | 64(2) | 67(2) | 45(2) | −22(2) | −14(2) | −3(2) |
| C(10) | 98(3) | 93(3) | 41(2) | −10(2) | −6(2) | −3(3) |
| C(11) | 75(3) | 89(3) | 52(2) | −30(2) | 1(2) | 9(2) |
| C(12) | 112(4) | 94(4) | 108(4) | −56(3) | −54(3) | −7(3) |
| C(13) | 49(2) | 41(2) | 73(2) | −12(2) | −1(2) | −20(2) |
| C(14) | 49(2) | 32(2) | 60(2) | −7(1) | −16(2) | −15(1) |
| C(15) | 65(2) | 46(2) | 78(2) | −14(2) | −33(2) | −17(2) |
| C(16) | 90(3) | 59(2) | 73(3) | −29(2) | −25(2) | −15(2) |
| C(17) | 73(3) | 52(2) | 81(3) | −33(2) | −9(2) | −4(2) |
| C(18) | 48(2) | 36(2) | 80(2) | −16(2) | −17(2) | −4(2) |
| C(19) | 48(2) | 29(2) | 55(2) | −5(1) | −17(2) | −12(1) |
| C(20) | 64(2) | 38(2) | 52(2) | 1(1) | −21(2) | −22(2) |
| C(21) | 79(3) | 45(2) | 48(2) | −6(2) | 2(2) | −30(2) |
| C(22) | 47(2) | 46(2) | 68(2) | −22(2) | −9(2) | −17(2) |
| C(23) | 45(2) | 49(2) | 77(2) | −21(2) | −11(2) | −23(2) |
| C(24) | 53(2) | 70(2) | 93(3) | −35(2) | −3(2) | −30(2) |
| C(25) | 50(2) | 87(3) | 142(5) | −62(3) | 13(3) | −32(2) |
| C(26) | 46(2) | 63(3) | 180(6) | −45(3) | −25(3) | −13(2) |
| C(27) | 59(3) | 66(3) | 120(4) | −17(3) | −34(3) | −21(2) |
| C(28) | 54(2) | 53(2) | 89(3) | −14(2) | −27(2) | −24(2) |
| C(29) | 73(3) | 79(3) | 72(2) | −24(2) | −24(2) | −34(2) |
| C(30) | 63(2) | 64(2) | 79(3) | −34(2) | −12(2) | −25(2) |

TABLE 5

Hydrogen Coordinates ($\times 10^4$) and Isotropic Displacement Parameters ($A^2 \times 10^3$)

| | x | y | z | U(eq) |
|---|---|---|---|---|
| H(2A) | 7681(5) | 7964(5) | 3477(4) | 127 |
| H(2B) | 9205(5) | 7454(5) | 3826(4) | 127 |
| H(2C) | 8193(5) | 6678(5) | 4310(4) | 127 |
| H(3A) | 10793(5) | 4834(4) | 2910(4) | 129 |
| H(3B) | 10109(5) | 4752(4) | 3961(4) | 129 |
| H(3C) | 11120(5) | 5529(4) | 3476(4) | 129 |
| H(4A) | 10030(5) | 7013(5) | 1580(4) | 147 |
| H(4B) | 10346(5) | 7600(5) | 2237(4) | 147 |
| H(4C) | 8842(5) | 8180(5) | 1844(4) | 147 |
| H(6A) | 6580(5) | 5724(5) | 4642(3) | 141 |
| H(6B) | 8188(5) | 4835(5) | 4714(3) | 141 |
| H(6C) | 6988(5) | 4252(5) | 5117(3) | 141 |
| H(7A) | 5116(4) | 5673(4) | 3545(4) | 142 |
| H(7B) | 5556(4) | 4205(4) | 4062(4) | 142 |
| H(7C) | 5798(4) | 4734(4) | 2942(4) | 142 |
| H(8A) | 9333(4) | 3418(4) | 3673(3) | 116 |
| H(8B) | 8399(4) | 3346(4) | 3020(3) | 116 |
| H(8C) | 8155(4) | 2817(4) | 4140(3) | 116 |
| H(10A) | 6968(5) | 7681(5) | 725(3) | 137 |
| H(10B) | 8098(5) | 6971(5) | 45(3) | 137 |
| H(10C) | 8579(5) | 7494(5) | 672(3) | 137 |
| H(11A) | 9862(4) | 4129(5) | 1884(3) | 126 |
| H(11B) | 10376(4) | 5285(5) | 1393(3) | 126 |
| H(11C) | 9894(4) | 4762(5) | 767(3) | 126 |
| H(12A) | 6175(6) | 5824(5) | 1429(4) | 150 |
| H(12B) | 7271(6) | 4451(5) | 1851(4) | 150 |
| H(12C) | 7341(6) | 5150(5) | 742(4) | 150 |
| H(13A) | 6915(4) | 10013(3) | 1969(3) | 66 |
| H(15A) | 5935(4) | 10719(3) | 3734(3) | 74 |
| H(16A) | 3933(5) | 11564(4) | 4637(3) | 87 |
| H(17A) | 1688(5) | 12049(4) | 4245(3) | 86 |
| H(18A) | 1366(4) | 11760(3) | 2906(3) | 69 |
| H(20A) | 2872(4) | 11027(3) | 1207(2) | 62 |
| H(21A) | 5511(4) | 10203(3) | 694(2) | 70 |
| H(22A) | 3096(3) | 7457(3) | 2693(3) | 62 |
| H(24A) | 1073(4) | 8986(4) | 3865(3) | 80 |
| H(25A) | −1216(5) | 10504(5) | 3716(5) | 104 |
| H(26A) | −2044(5) | 11664(5) | 2202(5) | 113 |
| H(27A) | −692(5) | 11259(4) | 852(5) | 97 |
| H(29A) | 1990(5) | 9619(4) | 198(3) | 83 |
| H(30A) | 4012(4) | 7954(4) | 1011(3) | 76 |

Crystallographic Data for Cp(Indenyl)Ti(NP-t-Bu$_3$)Cl (8)

TABLE 1

Crystal Data and Structure Refinement

| | |
|---|---|
| Empirical formula | C35H45ClNPTi |
| Formula weight | 594.04 |
| Temperature | 293(2) K |
| Wavelength | 0.71073 A |
| Crystal system | monoclinic |
| Space group | P2(1)/c |
| Unit cell dimensions | |
| a 12.86(2) A | alpha 90o |
| b 14.46(2) A | beta 111.97(11)o |
| c 15.03(2) A | gamma 90o |
| Volume, Z | 2590(7) A3, 4 |
| Density (calculated) | 1.523 Mg/m3 |
| Absorption coefficient | 0.525 mm-1 |
| Crystal size | 0.30 × 0.30 × 0.19 mm |
| q range for data collection | 1.71 to 25.00o |
| Limiting indices | −16 < h < 16, −19 < k < 18, −14 < l < 19 |
| Reflections collected | 12696 |
| Independent reflections | 4483 (Rint = 0.0494) |
| Refinement method | Full-matrix least-squares on F2 |
| Data/restraints/parameters | 4483/0/271 |
| Goodness-of-fit on F2 | 1.091 |
| Final R indices [I > 2σ(I)] | R1 = 0.0655, wR2 = 0.1633 |
| R indices (all data) | R1 = 0.1017, wR2 = 0.1814 |
| Largest diff. peak and hole | 1.416 and −0.446 eA-3 |

TABLE 2

Atomic Coordinates [× 10⁴] and Equivalent Isotropic Displacement Parameters [Å² × 10³]

|   | x | y | z | U(eq) |
|---|---|---|---|---|
| Ti(1) | 1561(1) | 5422(1) | 2738(1) | 38(1) |
| Cl(1) | 1303(1) | 6620(1) | 3641(1) | 60(1) |
| P(1) | 3468(1) | 6433(1) | 2018(1) | 35(1) |
| N(1) | 2612(3) | 5854(2) | 2350(2) | 36(1) |
| C(1) | −232(4) | 4684(4) | 2488(4) | 66(2) |
| C(2) | −416(4) | 5469(4) | 1930(4) | 69(2) |
| C(3) | 100(4) | 5352(4) | 1274(4) | 58(1) |
| C(4) | 608(5) | 4492(4) | 1425(4) | 64(2) |
| C(5) | 403(5) | 4075(4) | 2189(4) | 70(2) |
| C(6) | 3586(4) | 5826(3) | 943(3) | 51(1) |
| C(7) | 2519(5) | 5998(4) | 83(4) | 75(2) |
| C(8) | 3651(6) | 4782(4) | 1124(4) | 73(2) |
| C(9) | 4604(5) | 6124(4) | 707(4) | 78(2) |
| C(10) | 2916(4) | 7655(3) | 1702(3) | 49(1) |
| C(11) | 1652(4) | 7617(3) | 1158(4) | 61(1) |
| C(12) | 3078(5) | 8212(4) | 2593(4) | 71(2) |
| C(13) | 3486(5) | 8171(3) | 1102(4) | 67(2) |
| C(14) | 4851(4) | 6443(3) | 3034(3) | 48(1) |
| C(15) | 5373(5) | 5480(4) | 3160(4) | 76(2) |
| C(16) | 4656(5) | 6652(4) | 3970(3) | 70(2) |
| C(17) | 5692(4) | 7148(4) | 2919(4) | 64(2) |
| C(18) | 2606(4) | 4504(3) | 3892(3) | 46(1) |
| C(19) | 3028(5) | 3708(4) | 3492(4) | 64(1) |
| C(20) | 2707(5) | 2898(4) | 3769(4) | 66(2) |
| C(21) | 2092(4) | 3089(3) | 4380(3) | 49(1) |
| C(22) | 1611(4) | 2516(4) | 4867(4) | 59(1) |
| C(23) | 1095(4) | 2906(4) | 5427(4) | 64(2) |
| C(24) | 1054(5) | 3854(4) | 5510(4) | 64(2) |
| C(25) | 1521(4) | 4430(4) | 5043(3) | 53(1) |
| C(26) | 2047(4) | 4057(3) | 4470(3) | 42(1) |

TABLE 3

Selected Bond Lengths [Å] and Angles [°]

| Ti(1)—N(1) | 1.773(4) |
|---|---|
| Ti(1)—C(18) | 2.198(5) |
| Ti(1)—C(3) | 2.299(6) |
| Ti(1)—Cl(1) | 2.299(2) |
| Ti(1)—C(4) | 2.322(6) |
| Ti(1)—C(2) | 2.374(7) |
| Ti(1)—C(5) | 2.403(6) |
| Ti(1)—C(1) | 2.439(6) |
| P(1)—N(1) | 1.604(4) |
| P(1)—C(14) | 1.861(6) |
| P(1)—C(6) | 1.894(5) |
| P(1)—C(10) | 1.897(5) |
| C(1)—C(2) | 1.378(8) |
| C(1)—C(5) | 1.386(8) |
| C(2)—C(3) | 1.389(8) |
| C(3)—C(4) | 1.383(7) |
| C(4)—C(5) | 1.406(8) |
| C(6)—C(7) | 1.512(8) |
| C(6)—C(8) | 1.531(7) |
| C(6)—C(9) | 1.540(7) |
| C(10)—C(12) | 1.509(7) |
| C(10)—C(11) | 1.522(7) |
| C(10)—C(13) | 1.550(7) |
| C(14)—C(15) | 1.527(7) |
| C(14)—C(17) | 1.542(6) |
| C(14)—C(16) | 1.548(7) |
| C(18)—C(26) | 1.469(6) |
| C(18)—C(19) | 1.491(7) |
| C(19)—C(20) | 1.358(7) |
| C(20)—C(21) | 1.446(7) |
| C(21)—C(22) | 1.394(7) |
| C(21)—C(26) | 1.409(7) |
| C(22)—C(23) | 1.373(7) |
| C(23)—C(24) | 1.379(8) |
| C(24)—C(25) | 1.364(7) |
| C(25)—C(26) | 1.389(6) |

TABLE 3-continued

Selected Bond Lengths [Å] and Angles [°]

| N(1)—Ti(1)—C(18) | 98.9(2) |
|---|---|
| N(1)—Ti(1)—C(3) | 98.7(2) |
| C(18)—Ti(1)—C(3) | 140.1(2) |
| N(1)—Ti(1)—Cl(1) | 103.03(14) |
| C(18)—Ti(1)—Cl(1) | 99.8(2) |
| C(3)—Ti(1)—Cl(1) | 110.6(2) |
| N(1)—Ti(1)—C(4) | 98.6(2) |
| C(18)—Ti(1)—C(4) | 107.0(2) |
| C(3)—Ti(1)—C(4) | 34.8(2) |
| Cl(1)—Ti(1)—C(4) | 142.3(2) |
| N(1)—Ti(1)—C(2) | 128.6(2) |
| C(18)—Ti(1)—C(2) | 130.0(2) |
| C(3)—Ti(1)—C(2) | 34.5(2) |
| Cl(1)—Ti(1)—C(2) | 85.2(2) |
| C(4)—Ti(1)—C(2) | 57.2(2) |
| N(1)—Ti(1)—C(5) | 128.5(2) |
| C(18)—Ti(1)—C(5) | 84.2(2) |
| C(3)—Ti(1)—C(5) | 57.0(2) |
| Cl(1)—Ti(1)—C(5) | 127.3(2) |
| C(4)—Ti(1)—C(5) | 34.6(2) |
| C(2)—Ti(1)—C(5) | 55.9(2) |
| N(1)—Ti(1)—C(1) | 153.6(2) |
| C(18)—Ti(1)—C(1) | 97.0(2) |
| C(3)—Ti(1)—C(1) | 56.4(2) |
| Cl(1)—Ti(1)—C(1) | 94.8(2) |
| C(4)—Ti(1)—C(1) | 56.5(2) |
| C(2)—Ti(1)—C(1) | 33.2(2) |
| C(5)—Ti(1)—C(1) | 33.3(2) |
| N(1)—P(1)—C(14) | 107.7(2) |
| N(1)—P(1)—C(6) | 107.8(2) |
| C(14)—P(1)—C(6) | 110.3(2) |
| N(1)—P(1)—C(10) | 109.1(2) |
| C(14)—P(1)—C(10) | 110.6(2) |
| C(6)—P(1)—C(10) | 111.1(2) |
| P(1)—N(1)—Ti(1) | 169.1(2) |
| C(2)—C(1)—C(5) | 108.3(5) |
| C(2)—C(1)—Ti(1) | 70.8(3) |
| C(5)—C(1)—Ti(1) | 71.9(3) |
| C(1)—C(2)—C(3) | 108.2(5) |
| C(1)—C(2)—Ti(1) | 76.0(3) |
| C(3)—C(2)—Ti(1) | 69.8(3) |
| C(4)—C(3)—C(2) | 108.4(5) |
| C(4)—C(3)—Ti(1) | 73.5(3) |
| C(2)—C(3)—Ti(1) | 75.7(3) |
| C(3)—C(4)—C(5) | 107.3(5) |
| C(3)—C(4)—Ti(1) | 71.7(3) |
| C(5)—C(4)—Ti(1) | 75.8(3) |
| C(1)—C(5)—C(4) | 107.8(5) |
| C(1)—C(5)—Ti(1) | 74.8(3) |
| C(4)—C(5)—Ti(1) | 69.6(3) |
| C(7)—C(6)—C(8) | 106.6(5) |
| C(7)—C(6)—C(9) | 109.6(5) |
| C(8)—C(6)—C(9) | 108.8(4) |
| C(7)—C(6)—P(1) | 108.4(4) |
| C(8)—C(6)—P(1) | 108.7(3) |
| C(9)—C(6)—P(1) | 114.3(4) |
| C(12)—C(10)—C(11) | 105.1(4) |
| C(12)—C(10)—C(13) | 108.7(4) |
| C(11)—C(10)—C(13) | 110.3(4) |
| C(12)—C(10)—P(1) | 111.1(4) |
| C(11)—C(10)—P(1) | 109.0(3) |
| C(13)—C(10)—P(1) | 112.3(3) |
| C(15)—C(14)—C(17) | 108.8(4) |
| C(15)—C(14)—C(16) | 106.2(4) |
| C(17)—C(14)—C(16) | 109.4(4) |
| C(15)—C(14)—P(1) | 109.6(3) |
| C(17)—C(14)—P(1) | 114.1(3) |
| C(16)—C(14)—P(1) | 108.5(4) |
| C(26)—C(18)—C(19) | 103.4(4) |
| C(26)—C(18)—Ti(1) | 116.3(3) |
| C(19)—C(18)—Ti(1) | 110.8(3) |
| C(20)—C(19)—C(18) | 110.1(4) |
| C(19)—C(20)—C(21) | 109.3(5) |
| C(22)—C(21)—C(26) | 119.9(5) |
| C(22)—C(21)—C(20) | 132.5(5) |
| C(26)—C(21)—C(20) | 107.6(4) |
| C(23)—C(22)—C(21) | 119.3(5) |

TABLE 3-continued

Selected Bond Lengths [A] and Angles [o]

| | | |
|---|---|---|
| C(22)—C(23)—C(24) | 120.4(5) | |
| C(25)—C(24)—C(23) | 121.4(5) | |
| C(24)—C(25)—C(26) | 119.5(5) | |
| C(25)—C(26)—C(21) | 119.5(4) | |
| C(25)—C(26)—C(18) | 131.0(4) | |
| C(21)—C(26)—C(18) | 109.5(4) | |

TABLE 4

Anisotropic Displacement Parameters [$A^2 \times 10^3$]

| | U11 | U22 | U33 | U23 | U13 | U12 |
|---|---|---|---|---|---|---|
| Ti(1) | 34(1) | 49(1) | 31(1) | −2(1) | 11(1) | −6(1) |
| Cl(1) | 65(1) | 62(1) | 60(1) | −17(1) | 32(1) | −6(1) |
| P(1) | 31(1) | 39(1) | 33(1) | 0(1) | 10(1) | −2(1) |
| N(1) | 32(2) | 46(2) | 30(2) | −3(2) | 10(2) | −4(2) |
| C(1) | 46(3) | 99(5) | 55(3) | −13(3) | 22(3) | −34(3) |
| C(2) | 37(3) | 84(4) | 72(4) | −19(3) | 2(3) | −4(3) |
| C(3) | 43(3) | 69(4) | 42(3) | 1(2) | −6(2) | −12(3) |
| C(4) | 57(4) | 85(4) | 47(3) | −27(3) | 15(3) | −16(3) |
| C(5) | 71(4) | 55(3) | 59(4) | −1(3) | −4(3) | −18(3) |
| C(6) | 58(3) | 61(3) | 44(3) | −10(2) | 29(3) | −12(2) |
| C(7) | 85(5) | 93(4) | 40(3) | −13(3) | 15(3) | −23(4) |
| C(8) | 97(5) | 58(3) | 82(4) | −22(3) | 52(4) | −12(3) |
| C(9) | 92(5) | 84(4) | 83(4) | −15(3) | 61(4) | −18(3) |
| C(10) | 45(3) | 41(3) | 57(3) | 8(2) | 14(2) | 1(2) |
| C(11) | 49(3) | 55(3) | 75(4) | 16(3) | 18(3) | 7(2) |
| C(12) | 71(4) | 55(3) | 90(4) | −13(3) | 33(3) | −1(3) |
| C(13) | 62(4) | 54(3) | 79(4) | 17(3) | 21(3) | −8(3) |
| C(14) | 34(3) | 58(3) | 42(3) | 6(2) | 3(3) | −4(2) |
| C(15) | 52(4) | 69(4) | 82(4) | 10(3) | −3(3) | 8(3) |
| C(16) | 61(4) | 99(4) | 35(3) | 3(3) | 1(2) | −20(3) |
| C(17) | 36(3) | 80(4) | 67(4) | −2(3) | 9(3) | −15(3) |
| C(18) | 39(3) | 52(3) | 44(3) | 6(2) | 11(2) | −1(2) |
| C(19) | 58(4) | 74(4) | 66(4) | 13(3) | 32(3) | 12(3) |
| C(20) | 67(4) | 58(3) | 77(4) | 7(3) | 32(3) | 18(3) |
| C(21) | 38(3) | 54(3) | 48(3) | 7(2) | 9(2) | 3(2) |
| C(22) | 45(3) | 57(3) | 63(3) | 15(3) | 8(3) | −4(2) |
| C(23) | 52(4) | 82(4) | 55(3) | 18(3) | 16(3) | −8(3) |
| C(24) | 57(4) | 87(4) | 50(3) | 5(3) | 23(3) | −4(3) |
| C(25) | 51(3) | 64(3) | 41(3) | −1(2) | 16(2) | −2(2) |
| C(26) | 33(3) | 57(3) | 31(2) | 4(2) | 5(2) | −1(2) |

TABLE 5

Hydrogen Coordinates ($\times 10^4$) and Isotropic Displacement Parameters ($A^2 \times 10^3$)

| | x | y | z | U(eq) |
|---|---|---|---|---|
| H(1A) | −536(4) | 4563(4) | 2985(4) | 79 |
| H(2A) | −905(4) | 5987(4) | 1941(4) | 83 |
| H(3A) | 4(4) | 5758(4) | 727(4) | 69 |
| H(4A) | 935(5) | 4189(4) | 1007(4) | 77 |
| H(5A) | 605(5) | 3442(4) | 2422(4) | 84 |
| H(7A) | 2444(5) | 6648(4) | −57(4) | 113 |
| H(7B) | 1887(5) | 5788(4) | 222(4) | 113 |
| H(7C) | 2548(5) | 5667(4) | −461(4) | 113 |
| H(8A) | 4319(6) | 4640(4) | 1667(4) | 110 |
| H(8B) | 3667(6) | 4464(4) | 569(4) | 110 |
| H(8C) | 3006(6) | 4585(4) | 1251(4) | 110 |
| H(9A) | 5280(5) | 6015(4) | 1253(4) | 117 |
| H(9B) | 4545(5) | 6771(4) | 551(4) | 117 |
| H(9C) | 4620(5) | 5774(4) | 170(4) | 117 |
| H(11A) | 1489(4) | 7269(3) | 578(4) | 92 |
| H(11B) | 1365(4) | 8234(3) | 1004(4) | 92 |
| H(11C) | 1306(4) | 7324(3) | 1551(4) | 92 |
| H(12A) | 3865(5) | 8264(3) | 2972(4) | 107 |
| H(12B) | 2708(5) | 7909(4) | 2961(4) | 107 |
| H(12C) | 2766(5) | 8819(4) | 2413(4) | 107 |
| H(13A) | 3388(5) | 7823(3) | 532(4) | 100 |

TABLE 5-continued

Hydrogen Coordinates ($\times 10^4$) and Isotropic Displacement Parameters ($A^2 \times 10^3$)

| | x | y | z | U(eq) |
|---|---|---|---|---|
| H(13B) | 4272(5) | 8240(3) | 1475(4) | 100 |
| H(13C) | 3151(5) | 8771(3) | 926(4) | 100 |
| H(15A) | 4856(5) | 5036(4) | 3233(4) | 114 |
| H(15B) | 6052(5) | 5472(4) | 3721(4) | 114 |
| H(15C) | 5540(5) | 5327(4) | 2606(4) | 114 |
| H(16A) | 4326(5) | 7254(4) | 3928(3) | 104 |
| H(16B) | 5360(5) | 6635(4) | 4505(3) | 104 |
| H(16C) | 4161(5) | 6195(4) | 4059(3) | 104 |
| H(17A) | 5371(4) | 7757(4) | 2839(4) | 96 |
| H(17B) | 5858(4) | 6991(4) | 2365(4) | 96 |
| H(17C) | 6370(4) | 7136(4) | 3480(4) | 96 |
| H(18A) | 3250(4) | 4857(3) | 4320(3) | 56 |
| H(19A) | 3450(5) | 3759(4) | 3108(4) | 76 |
| H(20A) | 2858(5) | 2312(4) | 3592(4) | 79 |
| H(22A) | 1639(4) | 1877(4) | 4812(4) | 70 |
| H(23A) | 771(4) | 2528(4) | 5753(4) | 77 |
| H(24A) | 700(5) | 4106(4) | 5892(4) | 77 |
| H(25A) | 1486(4) | 5068(4) | 5109(3) | 63 |

Crystallographic Data for Cp$_3$Ti(NP-t-Bu$_3$) (9)

TABLE 1

Crystal Data and Structure Refinement

| | |
|---|---|
| Empirical formula | C54H84N2P2Ti2 |
| Formula weight | 918.97 |
| Temperature | 293(2) K |
| Wavelength | 0.71073 A |
| Crystal system | triclinic |
| Space group | P-1 |
| Unit cell dimensions | |
| a 11.190(3) A | alpha 85.32(2)o |
| b 14.763(2) A | beta 73.01(2)o |
| c 16.157(3) A | gamma 82.94(2)o |
| Volume, Z | 2530.3(9) A3, 2 |
| Density (calculated) | 1.206 Mg/m3 |
| Absorption coefficient | 0.415 mm-1 |
| Crystal size | 0.34 × 0.28 × 0.25 mm |
| q range for data collection | 1.39 to 25.00o |
| Limiting indices | −14 < h < 13, −19 < k < 19, −21 < I < 14 |
| Reflections collected | 13084 |
| Independent reflections | 8539 (Rint = 0.0214) |
| Refinement method | Full-matrix least-squares on F$^2$ |
| Data/restraints/parameters | 8536/0/541 |
| Goodness-of-fit on F2 | 0.987 |
| Final R indices [I > 2σ(I)] | R1 = 0.0396, wR2 = 0.1223 |
| R indices (all data) | R1 = 0.0471, wR2 = 0.1339 |
| Largest diff. peak and hole | 0.358 and −0.395 eA-3 |

TABLE 2

Atomic Coordinates [$\times 10^4$] and Equivalent Isotropic Displacement Parameters [$A^2 \times 10^3$]

| | x | y | z | U(eq) |
|---|---|---|---|---|
| Ti(1) | 1052(1) | 304(1) | 2268(1) | 35(1) |
| Ti(2) | 8457(1) | 5423(1) | 3194(1) | 37(1) |
| P(1) | 3665(1) | 614(1) | 2872(1) | 33(1) |
| P(2) | 6711(1) | 5456(1) | 1757(1) | 32(1) |
| N(1) | 2479(1) | 428(1) | 2582(1) | 33(1) |
| N(2) | 7489(1) | 5405(1) | 2444(1) | 34(1) |
| C(1) | −753(3) | 41(1) | 3492(2) | 91(1) |
| C(2) | 277(4) | −443(3) | 3700(2) | 93(1) |
| C(3) | 718(3) | −1132(2) | 3145(2) | 75(1) |
| C(4) | −20(3) | −1100(2) | 2586(2) | 68(1) |
| C(5) | −947(2) | −385(2) | 2815(2) | 78(1) |
| C(6) | −271(3) | 1169(2) | 1379(2) | 68(1) |

TABLE 2-continued

Atomic Coordinates [× 10⁴] and Equivalent Isotropic Displacement Parameters [Å² × 10³]

|  | x | y | z | U(eq) |
|---|---|---|---|---|
| C(7) | −647(2) | 1548(2) | 2169(2) | 71(1) |
| C(8) | 365(2) | 1932(2) | 2292(2) | 59(1) |
| C(9) | 1366(2) | 1823(1) | 1543(2) | 55(1) |
| C(10) | 971(3) | 1334(2) | 990(2) | 65(1) |
| C(11) | 2199(2) | −563(2) | 1056(1) | 46(1) |
| C(12) | 2764(2) | −1439(2) | 1295(2) | 52(1) |
| C(13) | 2311(3) | −2118(2) | 991(2) | 64(1) |
| C(14) | 1492(3) | −1704(2) | 510(2) | 71(1) |
| C(15) | 1438(3) | −783(2) | 526(2) | 59(1) |
| C(16) | 5054(2) | 758(1) | 1878(2) | 47(1) |
| C(17) | 5581(2) | −173(2) | 1472(2) | 60(1) |
| C(18) | 4628(2) | 1351(2) | 1168(2) | 61(1) |
| C(19) | 6138(2) | 1188(2) | 2053(2) | 68(1) |
| C(20) | 3260(2) | 1684(1) | 3527(2) | 49(1) |
| C(21) | 1936(2) | 1650(2) | 4159(2) | 60(1) |
| C(22) | 4185(3) | 1818(2) | 4043(2) | 74(1) |
| C(23) | 3191(3) | 2542(2) | 2928(2) | 65(1) |
| C(24) | 4141(2) | −381(1) | 3579(1) | 43(1) |
| C(25) | 5469(2) | −419(2) | 3675(2) | 64(1) |
| C(26) | 3212(3) | −381(2) | 4497(2) | 62(1) |
| C(27) | 4022(2) | −1274(1) | 3198(2) | 50(1) |
| C(28) | 6577(2) | 5775(2) | 4383(2) | 64(1) |
| C(29) | 7539(3) | 5446(2) | 4755(2) | 68(1) |
| C(30) | 8407(3) | 6092(2) | 4551(2) | 72(1) |
| C(31) | 8003(3) | 6792(2) | 4027(2) | 71(1) |
| C(32) | 6860(3) | 6591(2) | 3939(2) | 66(1) |
| C(33) | 10158(2) | 6189(2) | 2184(2) | 63(1) |
| C(34) | 10283(2) | 5318(2) | 1879(2) | 55(1) |
| C(35) | 10627(2) | 4696(2) | 2481(2) | 65(1) |
| C(36) | 10757(2) | 5201(3) | 3150(2) | 75(1) |
| C(37) | 10505(3) | 6100(2) | 2937(2) | 75(1) |
| C(38) | 8379(2) | 3852(2) | 3573(2) | 50(1) |
| C(39) | 7120(2) | 3596(2) | 4023(2) | 64(1) |
| C(40) | 7130(3) | 3181(2) | 4800(2) | 85(1) |
| C(41) | 8364(3) | 3107(2) | 4877(2) | 89(1) |
| C(42) | 9125(3) | 3481(2) | 4143(2) | 68(1) |
| C(43) | 7181(2) | 4392(1) | 1101(2) | 44(1) |
| C(44) | 6817(3) | 4477(2) | 241(2) | 71(1) |
| C(45) | 8604(2) | 4139(2) | 887(2) | 52(1) |
| C(46) | 6610(2) | 3573(2) | 1646(2) | 66(1) |
| C(47) | 7073(2) | 6518(2) | 1011(1) | 51(1) |
| C(48) | 6157(3) | 6808(2) | 463(2) | 79(1) |
| C(49) | 8396(2) | 6359(2) | 386(2) | 61(1) |
| C(50) | 7104(3) | 7303(2) | 1560(2) | 68(1) |
| C(51) | 4936(2) | 5527(1) | 2290(2) | 42(1) |
| C(52) | 4674(2) | 4860(2) | 3092(2) | 54(1) |
| C(53) | 4155(2) | 5316(2) | 1702(2) | 64(1) |
| C(54) | 4453(2) | 6484(2) | 2630(2) | 59(1) |

TABLE 3

Selected Bond Lengths [Å] and Angles [°]

| Ti(1)—N(1) | 1.844(2) |
|---|---|
| Ti(1)—C(11) | 2.378(2) |
| Ti(1)—C(1) | 2.423(3) |
| Ti(1)—C(8) | 2.432(2) |
| Ti(1)—C(2) | 2.442(3) |
| Ti(1)—C(3) | 2.456(3) |
| Ti(1)—C(9) | 2.460(2) |
| Ti(1)—C(4) | 2.464(2) |
| Ti(1)—C(5) | 2.465(3) |
| Ti(1)—C(10) | 2.480(2) |
| Ti(1)—C(7) | 2.508(2) |
| Ti(1)—C(6) | 2.523(3) |
| Ti(2)—N(2) | 1.850(2) |
| Ti(2)—C(38) | 2.355(2) |
| Ti(2)—C(29) | 2.431(2) |
| Ti(2)—C(28) | 2.433(2) |
| Ti(2)—C(32) | 2.438(2) |
| Ti(2)—C(31) | 2.438(2) |

TABLE 3-continued

Selected Bond Lengths [Å] and Angles [°]

| Ti(2)—C(33) | 2.445(2) |
|---|---|
| Ti(2)—C(30) | 2.460(3) |
| Ti(2)—C(34) | 2.481(2) |
| Ti(2)—C(35) | 2.510(2) |
| Ti(2)—C(37) | 2.523(3) |
| Ti(2)—C(36) | 2.534(3) |
| P(1)—N(1) | 1.590(2) |
| P(1)—C(16) | 1.900(2) |
| P(1)—C(20) | 1.907(2) |
| P(1)—C(24) | 1.908(2) |
| P(2)—N(2) | 1.590(2) |
| P(2)—C(43) | 1.900(2) |
| P(2)—C(47) | 1.907(2) |
| P(2)—C(51) | 1.914(2) |
| C(1)—C(5) | 1.387(5) |
| C(1)—C(2) | 1.392(5) |
| C(2)—C(3) | 1.361(5) |
| C(3)—C(4) | 1.385(4) |
| C(4)—C(5) | 1.377(4) |
| C(6)—C(7) | 1.365(4) |
| C(6)—C(10) | 1.392(4) |
| C(7)—C(8) | 1.397(4) |
| C(8)—C(9) | 1.392(4) |
| C(9)—C(10) | 1.389(4) |
| C(11)—C(12) | 1.443(3) |
| C(11)—C(15) | 1.451(3) |
| C(12)—C(13) | 1.361(3) |
| C(13)—C(14) | 1.422(4) |
| C(14)—C(15) | 1.355(4) |
| C(16)—C(18) | 1.536(3) |
| C(16)—C(19) | 1.541(3) |
| C(16)—C(17) | 1.546(3) |
| C(20)—C(21) | 1.539(3) |
| C(20)—C(23) | 1.540(3) |
| C(20)—C(22) | 1.545(3) |
| C(24)—C(25) | 1.532(3) |
| C(24)—C(27) | 1.534(3) |
| C(24)—C(26) | 1.543(3) |
| C(28)—C(32) | 1.373(4) |
| C(28)—C(29) | 1.400(4) |
| C(29)—C(30) | 1.397(4) |
| C(30)—C(31) | 1.398(4) |
| C(31)—C(32) | 1.397(4) |
| C(33)—C(37) | 1.374(4) |
| C(33)—C(34) | 1.391(4) |
| C(34)—C(35) | 1.387(4) |
| C(35)—C(36) | 1.411(4) |
| C(36)—C(37) | 1.360(4) |
| C(38)—C(42) | 1.449(3) |
| C(38)—C(39) | 1.465(3) |
| C(39)—C(40) | 1.354(4) |
| C(40)—C(41) | 1.412(4) |
| C(41)—C(42) | 1.362(4) |
| C(43)—C(46) | 1.527(3) |
| C(43)—C(45) | 1.532(3) |
| C(43)—C(44) | 1.550(3) |
| C(47)—C(50) | 1.526(4) |
| C(47)—C(49) | 1.532(3) |
| C(47)—C(48) | 1.542(3) |
| C(51)—C(54) | 1.534(3) |
| C(51)—C(53) | 1.538(3) |
| C(51)—C(52) | 1.542(3) |
| N(1)—Ti(1)—C(11) | 92.71(7) |
| N(1)—Ti(1)—C(1) | 113.43(11) |
| C(11)—Ti(1)—C(1) | 133.41(10) |
| N(1)—Ti(1)—C(8) | 93.92(8) |
| C(11)—Ti(1)—C(8) | 128.12(9) |
| C(1)—Ti(1)—C(8) | 89.46(11) |
| N(1)—Ti(1)—C(2) | 86.29(10) |
| C(11)—Ti(1)—C(2) | 120.80(12) |
| C(1)—Ti(1)—C(2) | 33.24(12) |
| C(8)—Ti(1)—C(2) | 110.96(13) |
| N(1)—Ti(1)—C(3) | 91.95(8) |
| C(11)—Ti(1)—C(3) | 88.83(10) |
| C(1)—Ti(1)—C(3) | 54.20(11) |
| C(8)—Ti(1)—C(3) | 142.13(11) |
| C(2)—Ti(1)—C(3) | 32.26(12) |

TABLE 3-continued

Selected Bond Lengths [A] and Angles [o]

| | |
|---|---|
| N(1)—Ti(1)—C(9) | 84.83(7) |
| C(11)—Ti(1)—C(9) | 96.90(8) |
| C(1)—Ti(1)—C(9) | 122.18(11) |
| C(8)—Ti(1)—C(9) | 33.06(9) |
| C(2)—Ti(1)—C(9) | 141.61(12) |
| C(3)—Ti(1)—C(9) | 173.54(11) |
| N(1)—Ti(1)—C(4) | 123.17(9) |
| C(11)—Ti(1)—C(4) | 78.93(9) |
| C(1)—Ti(1)—C(4) | 54.54(11) |
| C(8)—Ti(1)—C(4) | 134.93(9) |
| C(2)—Ti(1)—C(4) | 54.29(11) |
| C(3)—Ti(1)—C(4) | 32.71(10) |
| C(9)—Ti(1)—C(4) | 151.64(9) |
| N(1)—Ti(1)—C(5) | 140.51(9) |
| C(11)—Ti(1)—C(5) | 104.10(10) |
| C(1)—Ti(1)—C(5) | 32.96(11) |
| C(8)—Ti(1)—C(5) | 102.62(10) |
| C(2)—Ti(1)—C(5) | 54.36(12) |
| C(3)—Ti(1)—C(5) | 53.75(10) |
| C(9)—Ti(1)—C(5) | 126.98(10) |
| C(4)—Ti(1)—C(5) | 32.45(10) |
| N(1)—Ti(1)—C(10) | 109.94(9) |
| C(11)—Ti(1)—C(10) | 75.39(8) |
| C(1)—Ti(1)—C(10) | 124.31(12) |
| C(8)—Ti(1)—C(10) | 54.07(9) |
| C(2)—Ti(1)—C(10) | 157.39(13) |
| C(3)—Ti(1)—C(10) | 153.27(11) |
| C(9)—Ti(1)—C(10) | 32.66(8) |
| C(4)—Ti(1)—C(10) | 121.36(10) |
| C(5)—Ti(1)—C(10) | 108.80(11) |
| N(1)—Ti(1)—C(7) | 126.41(8) |
| C(11)—Ti(1)—C(7) | 121.72(9) |
| C(1)—Ti(1)—C(7) | 73.34(12) |
| C(8)—Ti(1)—C(7) | 32.82(8) |
| C(2)—Ti(1)—C(7) | 104.85(14) |
| C(3)—Ti(1)—C(7) | 124.96(10) |
| C(9)—Ti(1)—C(7) | 54.00(9) |
| C(4)—Ti(1)—C(7) | 104.23(10) |
| C(5)—Ti(1)—C(7) | 73.69(10) |
| C(10)—Ti(1)—C(7) | 52.98(10) |
| N(1)—Ti(1)—C(6) | 138.77(8) |
| C(11)—Ti(1)—C(6) | 90.30(9) |
| C(1)—Ti(1)—C(6) | 93.27(13) |
| C(8)—Ti(1)—C(6) | 53.82(9) |
| C(2)—Ti(1)—C(6) | 126.32(12) |
| C(3)—Ti(1)—C(6) | 129.24(10) |
| C(9)—Ti(1)—C(6) | 54.00(9) |
| C(4)—Ti(1)—C(6) | 97.76(10) |
| C(5)—Ti(1)—C(6) | 77.50(10) |
| C(10)—Ti(1)—C(6) | 32.28(9) |
| C(7)—Ti(1)—C(6) | 31.49(9) |
| N(2)—Ti(2)—C(38) | 92.79(7) |
| N(2)—Ti(2)—C(29) | 122.09(9) |
| C(38)—Ti(2)—C(29) | 78.66(9) |
| N(2)—Ti(2)—C(28) | 90.54(8) |
| C(38)—Ti(2)—C(28) | 90.16(9) |
| C(29)—Ti(2)—C(28) | 33.46(9) |
| N(2)—Ti(2)—C(32) | 86.36(8) |
| C(38)—Ti(2)—C(32) | 122.77(10) |
| C(29)—Ti(2)—C(32) | 55.17(10) |
| C(28)—Ti(2)—C(32) | 32.74(9) |
| N(2)—Ti(2)—C(31) | 114.22(9) |
| C(38)—Ti(2)—C(31) | 133.80(9) |
| C(29)—Ti(2)—C(31) | 55.39(10) |
| C(28)—Ti(2)—C(31) | 54.91(10) |
| C(32)—Ti(2)—C(31) | 33.30(9) |
| N(2)—Ti(2)—C(33) | 96.81(8) |
| C(38)—Ti(2)—C(33) | 128.61(9) |
| C(29)—Ti(2)—C(33) | 132.94(10) |
| C(28)—Ti(2)—C(33) | 139.80(10) |
| C(32)—Ti(2)—C(33) | 108.19(10) |
| C(31)—Ti(2)—C(33) | 86.45(10) |
| N(2)—Ti(2)—C(30) | 140.85(9) |
| C(38)—Ti(2)—C(30) | 103.68(10) |
| C(29)—Ti(2)—C(30) | 33.19(9) |
| C(28)—Ti(2)—C(30) | 54.77(9) |
| C(32)—Ti(2)—C(30) | 54.81(10) |
| C(31)—Ti(2)—C(30) | 33.16(10) |
| C(33)—Ti(2)—C(30) | 99.85(10) |
| N(2)—Ti(2)—C(34) | 85.64(8) |
| C(38)—Ti(2)—C(34) | 98.71(9) |
| C(29)—Ti(2)—C(34) | 152.12(9) |
| C(28)—Ti(2)—C(34) | 170.49(10) |
| C(32)—Ti(2)—C(34) | 138.05(10) |
| C(31)—Ti(2)—C(34) | 119.11(9) |
| C(33)—Ti(2)—C(34) | 32.79(8) |
| C(30)—Ti(2)—C(34) | 125.38(9) |
| N(2)—Ti(2)—C(35) | 108.30(9) |
| C(38)—Ti(2)—C(35) | 75.11(9) |
| C(29)—Ti(2)—C(35) | 123.62(10) |
| C(28)—Ti(2)—C(35) | 156.33(10) |
| C(32)—Ti(2)—C(35) | 157.15(10) |
| C(31)—Ti(2)—C(35) | 124.46(10) |
| C(33)—Ti(2)—C(35) | 53.92(9) |
| C(30)—Ti(2)—C(35) | 110.18(10) |
| C(34)—Ti(2)—C(35) | 32.26(8) |
| N(2)—Ti(2)—C(37) | 128.81(9) |
| C(38)—Ti(2)—C(37) | 119.07(10) |
| C(29)—Ti(2)—C(37) | 103.83(10) |
| C(28)—Ti(2)—C(37) | 125.12(9) |
| C(32)—Ti(2)—C(37) | 104.53(10) |
| C(31)—Ti(2)—C(37) | 72.89(10) |
| C(33)—Ti(2)—C(37) | 32.06(9) |
| C(30)—Ti(2)—C(37) | 72.75(10) |
| C(34)—Ti(2)—C(37) | 52.87(9) |
| C(35)—Ti(2)—C(37) | 52.64(10) |
| N(2)—Ti(2)—C(36) | 138.52(8) |
| C(38)—Ti(2)—C(36) | 87.87(10) |
| C(29)—Ti(2)—C(36) | 98.72(10) |
| C(28)—Ti(2)—C(36) | 130.94(10) |
| C(32)—Ti(2)—C(36) | 127.19(11) |
| C(31)—Ti(2)—C(36) | 94.01(11) |
| C(33)—Ti(2)—C(36) | 53.39(10) |
| C(30)—Ti(2)—C(36) | 78.22(10) |
| C(34)—Ti(2)—C(36) | 53.41(9) |
| C(35)—Ti(2)—C(36) | 32.49(9) |
| C(37)—Ti(2)—C(36) | 31.21(10) |
| N(1)—P(1)—C(16) | 109.72(9) |
| N(1)—P(1)—C(20) | 109.34(9) |
| C(16)—P(1)—C(20) | 110.58(10) |
| N(1)—P(1)—C(24) | 111.28(9) |
| C(16)—P(1)—C(24) | 107.75(9) |
| C(20)—P(1)—C(24) | 108.16(10) |
| N(2)—P(2)—C(43) | 109.47(9) |
| N(2)—P(2)—C(47) | 108.61(10) |
| C(43)—P(2)—C(47) | 109.98(10) |
| N(2)—P(2)—C(51) | 112.69(9) |
| C(43)—P(2)—C(51) | 107.66(9) |
| C(47)—P(2)—C(51) | 108.42(9) |
| P(1)—N(1)—Ti(1) | 175.56(9) |
| P(2)—N(2)—Ti(2) | 175.43(9) |
| C(5)—C(1)—C(2) | 107.6(3) |
| C(5)—C(1)—Ti(1) | 75.2(2) |
| C(2)—C(1)—Ti(1) | 74.1(2) |
| C(3)—C(2)—C(1) | 107.7(3) |
| C(3)—C(2)—Ti(1) | 74.4(2) |
| C(1)—C(2)—Ti(1) | 72.6(2) |
| C(2)—C(3)—C(4) | 109.2(3) |
| C(2)—C(3)—Ti(1) | 73.3(2) |
| C(4)—C(3)—Ti(1) | 74.0(2) |
| C(5)—C(4)—C(3) | 107.3(3) |
| C(5)—C(4)—Ti(1) | 73.8(2) |
| C(3)—C(4)—Ti(1) | 73.3(2) |
| C(4)—C(5)—C(1) | 108.2(3) |
| C(4)—C(5)—Ti(1) | 73.73(14) |
| C(1)—C(5)—Ti(1) | 71.9(2) |
| C(7)—C(6)—C(10) | 107.6(2) |
| C(7)—C(6)—Ti(1) | 73.6(2) |
| C(10)—C(6)—Ti(1) | 72.14(14) |
| C(6)—C(7)—C(8) | 108.6(3) |
| C(6)—C(7)—Ti(1) | 74.89(14) |
| C(8)—C(7)—Ti(1) | 70.61(14) |
| C(9)—C(8)—C(7) | 107.9(2) |
| C(9)—C(8)—Ti(1) | 74.59(13) |

TABLE 3-continued

Selected Bond Lengths [A] and Angles [o]

| | |
|---|---|
| C(7)—C(8)—Ti(1) | 76.57(14) |
| C(10)—C(9)—C(8) | 106.8(2) |
| C(10)—C(9)—Ti(1) | 74.44(13) |
| C(8)—C(9)—Ti(1) | 72.35(13) |
| C(9)—C(10)—C(6) | 109.0(3) |
| C(9)—C(10)—Ti(1) | 72.90(13) |
| C(6)—C(10)—Ti(1) | 75.6(2) |
| C(12)—C(11)—C(15) | 104.2(2) |
| C(12)—C(11)—Ti(1) | 113.29(14) |
| C(15)—C(11)—Ti(1) | 113.8(2) |
| C(13)—C(12)—C(11) | 109.7(2) |
| C(12)—C(13)—C(14) | 107.8(2) |
| C(15)—C(14)—C(13) | 109.1(2) |
| C(14)—C(15)—C(11) | 108.9(2) |
| C(18)—C(16)—C(19) | 108.2(2) |
| C(18)—C(16)—C(17) | 104.9(2) |
| C(19)—C(16)—C(17) | 108.3(2) |
| C(18)—C(16)—P(1) | 110.2(2) |
| C(19)—C(16)—P(1) | 114.2(2) |
| C(17)—C(16)—P(1) | 110.44(14) |
| C(21)—C(20)—C(23) | 106.3(2) |
| C(21)—C(20)—C(22) | 109.0(2) |
| C(23)—C(20)—C(22) | 107.6(2) |
| C(21)—C(20)—P(1) | 108.3(2) |
| C(23)—C(20)—P(1) | 110.2(2) |
| C(22)—C(20)—P(1) | 115.2(2) |
| C(25)—C(24)—C(27) | 108.5(2) |
| C(25)—C(24)—C(26) | 107.7(2) |
| C(27)—C(24)—C(26) | 105.7(2) |
| C(25)—C(24)—P(1) | 115.8(2) |
| C(27)—C(24)—P(1) | 108.12(14) |
| C(26)—C(24)—P(1) | 110.6(2) |
| C(32)—C(28)—C(29) | 108.8(3) |
| C(32)—C(28)—Ti(2) | 73.83(14) |
| C(29)—C(28)—Ti(2) | 73.18(14) |
| C(30)—C(29)—C(28) | 107.2(3) |
| C(30)—C(29)—Ti(2) | 74.6(2) |
| C(28)—C(29)—Ti(2) | 73.36(13) |
| C(31)—C(30)—C(29) | 108.1(3) |
| C(31)—C(30)—Ti(2) | 72.57(14) |
| C(29)—C(30)—Ti(2) | 72.25(14) |
| C(30)—C(31)—C(32) | 107.5(3) |
| C(30)—C(31)—Ti(2) | 74.3(2) |
| C(32)—C(31)—Ti(2) | 73.33(14) |
| C(28)—C(32)—C(31) | 108.3(3) |
| C(28)—C(32)—Ti(2) | 73.43(14) |
| C(31)—C(32)—Ti(2) | 73.4(2) |
| C(37)—C(33)—C(34) | 107.4(3) |
| C(37)—C(33)—Ti(2) | 77.1(2) |
| C(34)—C(33)—Ti(2) | 75.01(13) |
| C(35)—C(34)—C(33) | 108.0(2) |
| C(35)—C(34)—Ti(2) | 75.04(13) |
| C(33)—C(34)—Ti(2) | 72.20(13) |
| C(34)—C(35)—C(36) | 107.3(2) |
| C(34)—C(35)—Ti(2) | 72.70(13) |
| C(36)—C(35)—Ti(2) | 74.7(2) |
| C(37)—C(36)—C(35) | 107.2(3) |
| C(37)—C(36)—Ti(2) | 73.9(2) |
| C(35)—C(36)—Ti(2) | 72.80(14) |
| C(36)—C(37)—C(33) | 109.9(3) |
| C(36)—C(37)—Ti(2) | 74.9(2) |
| C(33)—C(37)—Ti(2) | 70.85(14) |
| C(42)—C(38)—C(39) | 103.8(2) |
| C(42)—C(38)—Ti(2) | 115.2(2) |
| C(39)—C(38)—Ti(2) | 114.4(2) |
| C(40)—C(39)—C(38) | 109.0(3) |
| C(39)—C(40)—C(41) | 109.0(3) |
| C(42)—C(41)—C(40) | 108.8(3) |
| C(41)—C(42)—C(38) | 109.2(3) |
| C(46)—C(43)—C(45) | 104.8(2) |
| C(46)—C(43)—C(44) | 108.8(2) |
| C(45)—C(43)—C(44) | 108.1(2) |
| C(46)—C(43)—P(2) | 110.2(2) |
| C(45)—C(43)—P(2) | 109.91(14) |
| C(44)—C(43)—P(2) | 114.7(2) |
| C(50)—C(47)—C(49) | 106.0(2) |
| C(50)—C(47)—C(48) | 109.8(2) |
| C(49)—C(47)—C(48) | 107.6(2) |
| C(50)—C(47)—P(2) | 108.4(2) |
| C(49)—C(47)—P(2) | 109.52(14) |
| C(48)—C(47)—P(2) | 115.1(2) |
| C(54)—C(51)—C(53) | 108.2(2) |
| C(54)—C(51)—C(52) | 106.0(2) |
| C(53)—C(51)—C(52) | 108.7(2) |
| C(54)—C(51)—P(2) | 109.7(2) |
| C(53)—C(51)—P(2) | 115.2(2) |
| C(52)—C(51)—P(2) | 108.69(14) |

TABLE 4

Anisotropic Displacement Parameters [A² × 10³]

| | U11 | U22 | U33 | U23 | U13 | U12 |
|---|---|---|---|---|---|---|
| Ti(1) | 29(1) | 40(1) | 35(1) | −1(1) | −10(1) | −3(1) |
| Ti(2) | 33(1) | 45(1) | 30(1) | −6(1) | −5(1) | −3(1) |
| P(1) | 32(1) | 33(1) | 35(1) | 0(1) | −13(1) | −3(1) |
| P(2) | 30(1) | 35(1) | 27(1) | 0(1) | −3(1) | 0(1) |
| N(1) | 33(1) | 36(1) | 30(1) | −1(1) | −9(1) | −3(1) |
| N(2) | 34(1) | 33(1) | 32(1) | −2(1) | −4(1) | −3(1) |
| C(1) | 68(2) | 99(2) | 78(2) | −13(2) | 30(2) | −21(2) |
| C(2) | 94(2) | 146(3) | 41(2) | 24(2) | −9(2) | −70(2) |
| C(3) | 52(2) | 82(2) | 82(2) | 41(2) | −13(1) | −24(1) |
| C(4) | 64(2) | 60(2) | 76(2) | 4(1) | −8(1) | −27(1) |
| C(5) | 38(1) | 99(2) | 95(2) | 13(2) | −16(1) | −26(1) |
| C(6) | 67(2) | 66(2) | 88(2) | −1(1) | −50(2) | 0(1) |
| C(7) | 47(1) | 67(2) | 100(2) | −11(2) | −31(1) | 15(1) |
| C(8) | 66(2) | 44(1) | 74(2) | −11(1) | −35(1) | 12(1) |
| C(9) | 60(1) | 40(1) | 70(2) | 11(1) | −32(1) | −4(1) |
| C(10) | 90(2) | 54(1) | 50(1) | 9(1) | −27(1) | 9(1) |
| C(11) | 48(1) | 53(1) | 37(1) | −6(1) | −13(1) | −4(1) |
| C(12) | 53(1) | 54(1) | 50(1) | −14(1) | −18(1) | 7(1) |
| C(13) | 76(2) | 50(1) | 69(2) | −17(1) | −27(1) | 3(1) |
| C(14) | 83(2) | 68(2) | 75(2) | −27(1) | −40(2) | −5(1) |
| C(15) | 73(2) | 64(2) | 50(1) | −12(1) | −32(1) | 2(1) |
| C(16) | 32(1) | 51(1) | 53(1) | 10(1) | −8(1) | −8(1) |
| C(17) | 49(1) | 64(1) | 54(1) | −1(1) | 2(1) | −3(1) |
| C(18) | 51(1) | 69(2) | 55(1) | 20(1) | −6(1) | −10(1) |
| C(19) | 41(1) | 68(2) | 97(2) | 15(2) | −21(1) | −18(1) |
| C(20) | 56(1) | 41(1) | 58(1) | −13(1) | −27(1) | 0(1) |
| C(21) | 62(2) | 60(1) | 58(2) | −21(1) | −18(1) | 8(1) |
| C(22) | 82(2) | 68(2) | 90(2) | −28(2) | −49(2) | −2(1) |
| C(23) | 70(2) | 40(1) | 91(2) | −6(1) | −34(2) | −4(1) |
| C(24) | 48(1) | 44(1) | 41(1) | 3(1) | −23(1) | 0(1) |
| C(25) | 63(2) | 67(2) | 73(2) | 4(1) | −43(1) | 3(1) |
| C(26) | 81(2) | 65(2) | 36(1) | 4(1) | −17(1) | 0(1) |
| C(27) | 59(1) | 38(1) | 51(1) | 4(1) | −19(1) | 2(1) |
| C(28) | 47(1) | 91(2) | 47(1) | −27(1) | 4(1) | −6(1) |
| C(29) | 76(2) | 90(2) | 30(1) | −11(1) | −1(1) | 1(2) |
| C(30) | 62(2) | 108(2) | 50(2) | −32(2) | −14(1) | −5(2) |
| C(31) | 84(2) | 67(2) | 59(2) | −28(1) | −7(2) | −11(2) |
| C(32) | 68(2) | 73(2) | 52(2) | −29(1) | −13(1) | 19(1) |
| C(33) | 46(1) | 63(2) | 71(2) | 2(1) | −2(1) | −18(1) |
| C(34) | 34(1) | 79(2) | 45(2) | −6(1) | 1(1) | −11(1) |
| C(35) | 34(1) | 71(2) | 76(2) | −1(1) | 0(1) | 2(1) |
| C(36) | 38(1) | 129(3) | 58(2) | 6(2) | −16(1) | −14(2) |
| C(37) | 51(2) | 99(2) | 76(2) | −25(2) | −4(1) | −31(2) |
| C(38) | 53(1) | 48(1) | 46(1) | 3(1) | −15(1) | 3(1) |
| C(39) | 58(2) | 61(1) | 66(2) | 20(1) | −15(1) | −8(1) |
| C(40) | 91(2) | 81(2) | 66(2) | 34(2) | −6(2) | −11(2) |
| C(41) | 110(3) | 90(2) | 61(2) | 28(2) | −33(2) | 11(2) |
| C(42) | 67(2) | 75(2) | 62(2) | 8(1) | −28(1) | 11(1) |
| C(43) | 40(1) | 51(1) | 38(1) | −14(1) | −5(1) | −4(1) |
| C(44) | 66(2) | 102(2) | 51(2) | −32(1) | −20(1) | −4(2) |
| C(45) | 46(1) | 51(1) | 54(1) | −16(1) | −5(1) | 3(1) |
| C(46) | 62(2) | 46(1) | 83(2) | −16(1) | −3(1) | −13(1) |
| C(47) | 44(1) | 49(1) | 46(1) | 17(1) | −2(1) | 4(1) |
| C(48) | 62(2) | 99(2) | 62(2) | 35(2) | −14(1) | 10(2) |
| C(49) | 50(1) | 63(1) | 53(1) | 21(1) | 3(1) | −3(1) |
| C(50) | 65(2) | 38(1) | 82(2) | 8(1) | 2(1) | −2(1) |
| C(51) | 30(1) | 55(1) | 37(1) | −1(1) | −5(1) | −1(1) |

TABLE 4-continued

Anisotropic Displacement Parameters [A² × 10³]

| | U11 | U22 | U33 | U23 | U13 | U12 |
|---|---|---|---|---|---|---|
| C(52) | 43(1) | 70(2) | 43(1) | 3(1) | 1(1) | −14(1) |
| C(53) | 38(1) | 98(2) | 56(2) | −8(1) | −12(1) | −4(1) |
| C(54) | 40(1) | 63(1) | 64(2) | −9(1) | 0(1) | 9(1) |

TABLE 5

Hydrogen Coordinates (× 10⁴) and Isotropic Displacement Parameters (A² × 10³)

| | x | y | z | U(eq) |
|---|---|---|---|---|
| H(1A) | −1333(3) | 516(2) | 3835(2) | 109 |
| H(2A) | 552(4) | −361(3) | 4210(2) | 111 |
| H(3A) | 1379(3) | −1621(2) | 3184(2) | 90 |
| H(4A) | 24(3) | −1560(2) | 2171(2) | 81 |
| H(5A) | −1674(2) | −248(2) | 2588(2) | 93 |
| H(6A) | −811(3) | 902(2) | 1104(2) | 82 |
| H(7A) | −1507(2) | 1601(2) | 2556(2) | 85 |
| H(8A) | 319(2) | 2327(2) | 2762(2) | 71 |
| H(9A) | 2141(2) | 2122(1) | 1397(2) | 66 |
| H(10A) | 1445(3) | 1212(2) | 389(2) | 78 |
| H(11A) | 2867(2) | −212(2) | 694(1) | 55 |
| H(12A) | 3348(2) | −1527(2) | 1609(2) | 62 |
| H(13A) | 2504(3) | −2743(2) | 1083(2) | 77 |
| H(14A) | 1061(3) | −2015(2) | 229(2) | 85 |
| H(15A) | 986(3) | −361(2) | 242(2) | 71 |
| H(17A) | 5868(2) | −581(2) | 1884(2) | 89 |
| H(17B) | 6270(2) | −87(2) | 963(2) | 89 |
| H(17C) | 4933(2) | −428(2) | 1316(2) | 89 |
| H(18A) | 3951(2) | 1094(2) | 1050(2) | 92 |
| H(18B) | 5319(2) | 1369(2) | 650(2) | 92 |
| H(18C) | 4349(2) | 1959(2) | 1360(2) | 92 |
| H(19A) | 6419(2) | 826(2) | 2495(2) | 102 |
| H(19B) | 5851(2) | 1797(2) | 2242(2) | 102 |
| H(19C) | 6822(2) | 1208(2) | 1531(2) | 102 |
| H(21A) | 1930(2) | 1122(2) | 4549(2) | 90 |
| H(21B) | 1345(2) | 1613(2) | 3839(2) | 90 |
| H(21C) | 1706(2) | 2192(2) | 4484(2) | 90 |
| H(22A) | 5014(3) | 1840(2) | 3652(2) | 111 |
| H(22B) | 4190(3) | 1318(2) | 4461(2) | 111 |
| H(22C) | 3926(3) | 2381(2) | 4336(2) | 111 |
| H(23A) | 4000(3) | 2595(2) | 2519(2) | 97 |
| H(23B) | 2945(3) | 3074(2) | 3268(2) | 97 |
| H(23C) | 2585(3) | 2494(2) | 2623(2) | 97 |
| H(25A) | 5558(2) | 135(2) | 3913(2) | 95 |
| H(25B) | 6073(2) | −485(2) | 3116(2) | 95 |
| H(25C) | 5609(2) | −931(2) | 4054(2) | 95 |
| H(26A) | 2370(3) | −356(2) | 4457(2) | 93 |
| H(26B) | 3290(3) | 143(2) | 4786(2) | 93 |
| H(26C) | 3399(3) | −928(2) | 4820(2) | 93 |
| H(27A) | 3194(2) | −1260(1) | 3134(2) | 74 |
| H(27B) | 4167(2) | −1782(1) | 3580(2) | 74 |
| H(27C) | 4632(2) | −1337(1) | 2642(2) | 74 |
| H(28A) | 5781(2) | 5511(2) | 4487(2) | 77 |
| H(29A) | 7528(2) | 4920(2) | 5168(2) | 82 |
| H(30A) | 9123(3) | 6088(2) | 4784(2) | 87 |
| H(31A) | 8379(3) | 7367(2) | 3839(2) | 86 |
| H(32A) | 6300(3) | 7002(2) | 3676(2) | 79 |
| H(33A) | 10054(2) | 6763(2) | 1850(2) | 75 |
| H(34A) | 10260(2) | 5177(2) | 1302(2) | 65 |
| H(35A) | 10874(2) | 4041(2) | 2407(2) | 77 |
| H(36A) | 11096(3) | 4956(3) | 3627(2) | 90 |
| H(37A) | 10626(3) | 6610(2) | 3247(2) | 90 |
| H(38A) | 8688(2) | 3522(2) | 3037(2) | 60 |
| H(39A) | 6426(2) | 3701(2) | 3810(2) | 76 |
| H(40A) | 6436(3) | 2977(2) | 5216(2) | 101 |
| H(41A) | 8615(3) | 2846(2) | 5351(2) | 107 |
| H(42A) | 9987(3) | 3496(2) | 4027(2) | 82 |
| H(44A) | 7172(3) | 4990(2) | −107(2) | 107 |
| H(44B) | 5919(3) | 4564(2) | 366(2) | 107 |
| H(44C) | 7135(3) | 3929(2) | −68(2) | 107 |
| H(45A) | 9030(2) | 4627(2) | 542(2) | 78 |

TABLE 5-continued

Hydrogen Coordinates (× 10⁴) and Isotropic Displacement Parameters (A² × 10³)

| | x | y | z | U(eq) |
|---|---|---|---|---|
| H(45B) | 8832(2) | 3591(2) | 570(2) | 78 |
| H(45C) | 8842(2) | 4039(2) | 1414(2) | 78 |
| H(46A) | 5710(2) | 3685(2) | 1806(2) | 99 |
| H(46B) | 6885(2) | 3485(2) | 2159(2) | 99 |
| H(46C) | 6875(2) | 3036(2) | 1315(2) | 99 |
| H(48A) | 6141(3) | 6312(2) | 118(2) | 118 |
| H(48B) | 6430(2) | 7328(2) | 90(2) | 118 |
| H(48C) | 5330(3) | 6964(2) | 839(2) | 118 |
| H(49A) | 8429(2) | 5868(2) | 23(2) | 91 |
| H(49B) | 8993(2) | 6204(2) | 711(2) | 91 |
| H(49C) | 8596(2) | 6906(2) | 33(2) | 91 |
| H(50A) | 6291(3) | 7432(2) | 1966(2) | 102 |
| H(50B) | 7322(3) | 7837(2) | 1191(2) | 102 |
| H(50C) | 7717(3) | 7135(2) | 1870(2) | 102 |
| H(52A) | 4961(2) | 4247(2) | 2915(2) | 81 |
| H(52B) | 3788(2) | 4905(2) | 3377(2) | 81 |
| H(52C) | 5111(2) | 5012(2) | 3484(2) | 81 |
| H(53A) | 4443(2) | 4719(2) | 1482(2) | 96 |
| H(53B) | 4248(2) | 5763(2) | 1227(2) | 96 |
| H(53C) | 3286(2) | 5335(2) | 2029(2) | 96 |
| H(54A) | 4929(2) | 6628(2) | 3000(2) | 89 |
| H(54B) | 3582(2) | 6496(2) | 2953(2) | 89 |
| H(54C) | 4545(2) | 6925(2) | 2151(2) | 89 |

Crystallographic Data for (Indenyl)₃Ti(NP-t-Bu₃) (10)

TABLE 1

Crystal Data and Structure Refinement

| | |
|---|---|
| Empirical formula | C78H96N2P2Ti2 |
| Formula weight | 1219.31 |
| Temperature | 293(2) K |
| Wavelength | 0.71073 A |
| Crystal system | triclinic |
| Space group | P-1 |
| Unit cell dimensions | |
| a 12.858(7) A | alpha 73.45(5)° |
| b 15.930(9) A | beta 73.73(3)° |
| c 18.006(10) A | gamma 82.41(6)° |
| Volume, Z | 3388(3) A3, 2 |
| Density (calculated) | 1.195 Mg/m3 |
| Absorption coefficient | 0.327 mm-1 |
| Crystal size | 0.33 × 0.26 × 0.21 mm |
| q range for data collection | 1.22 to 24.00° |
| Limiting indices | −10 < h < 16, −21 < k < 21, −23 < l < 22 |
| Reflections collected | 14934 |
| Independent reflections | 9675 (Rint = 0.0860) |
| Refinement method | Full-matrix least-squares on F2 |
| Data/restraints/parameters | 9672/0/757 |
| Goodness-of-fit on F2 | 0.918 |
| Final R indices [I > 2σ(I)] | R1 = 0.0856, wR2 = 0.1788 |
| R indices (all data) | R1 = 0.1773, wR2 = 0.2259 |
| Largest diff. peak and hole | 0.543 and −0.596 eA-3 |

TABLE 2

Atomic Coordinates [× 10⁴] and Equivalent Isotropic Displacement Parameters [A² × 10³]

| | x | y | z | U(eq) |
|---|---|---|---|---|
| Ti(1) | 7698(1) | 1840(1) | 408(1) | 34(1) |
| Ti(2) | 13369(1) | 3115(1) | 5095(1) | 40(1) |
| P(1) | 8825(2) | 1810(1) | 1908(1) | 36(1) |
| P(2) | 12844(2) | 4188(1) | 3304(1) | 40(1) |
| N(1) | 8219(4) | 1880(3) | 1218(3) | 32(1) |
| N(2) | 13040(5) | 3679(4) | 4180(3) | 38(2) |
| C(1) | 8199(8) | 936(5) | 2834(4) | 57(2) |

TABLE 2-continued

Atomic Coordinates [× 10⁴] and Equivalent Isotropic Displacement Parameters [Å² × 10³]

|  | x | y | z | U(eq) |
|---|---|---|---|---|
| C(2) | 8910(8) | 647(6) | 3440(5) | 90(3) |
| C(3) | 7067(8) | 1277(6) | 3251(5) | 80(3) |
| C(4) | 7993(8) | 133(5) | 2585(5) | 76(3) |
| C(5) | 10291(6) | 1519(5) | 1530(4) | 48(2) |
| C(6) | 10713(7) | 2077(6) | 643(4) | 65(3) |
| C(7) | 10489(8) | 565(5) | 1502(6) | 79(3) |
| C(8) | 11047(7) | 1696(6) | 2011(5) | 70(3) |
| C(9) | 8606(6) | 2910(4) | 2148(4) | 39(2) |
| C(10) | 7453(7) | 3276(5) | 2133(5) | 59(2) |
| C(11) | 8861(7) | 2890(5) | 2955(5) | 59(2) |
| C(12) | 9382(7) | 3564(5) | 1469(4) | 55(2) |
| C(13) | 8282(8) | 395(5) | 411(5) | 57(2) |
| C(14) | 7279(7) | 480(4) | 227(4) | 47(2) |
| C(15) | 7427(6) | 1003(5) | −579(4) | 43(2) |
| C(16) | 6704(7) | 1241(5) | −1088(5) | 53(2) |
| C(17) | 7119(10) | 1709(6) | −1880(6) | 75(3) |
| C(18) | 8182(10) | 1949(6) | −2148(5) | 76(3) |
| C(19) | 8872(7) | 1755(5) | −1675(5) | 61(2) |
| C(20) | 8503(7) | 1266(5) | −855(4) | 46(2) |
| C(21) | 9026(7) | 915(5) | −228(5) | 52(2) |
| C(22) | 5937(6) | 1977(5) | 957(4) | 39(2) |
| C(23) | 5203(6) | 2017(4) | 432(4) | 36(2) |
| C(24) | 5089(6) | 2618(4) | −282(4) | 38(2) |
| C(25) | 4373(6) | 2456(5) | −668(4) | 48(2) |
| C(26) | 3767(7) | 1725(5) | −361(5) | 59(2) |
| C(27) | 3855(6) | 1140(5) | 350(5) | 51(2) |
| C(28) | 4554(6) | 1301(5) | 755(4) | 45(2) |
| C(29) | 4775(6) | 818(5) | 1517(4) | 54(2) |
| C(30) | 5535(6) | 1231(5) | 1643(4) | 48(2) |
| C(31) | 7871(6) | 3140(4) | −476(4) | 36(2) |
| C(32) | 7458(4) | 3920(4) | −176(4) | 31(2) |
| C(33) | 6447(6) | 4247(4) | 160(4) | 38(2) |
| C(34) | 6321(7) | 5022(5) | 365(4) | 48(2) |
| C(35) | 7203(7) | 5498(5) | 273(4) | 48(2) |
| C(36) | 8224(7) | 5176(5) | −44(4) | 48(2) |
| C(37) | 8369(7) | 4407(4) | −280(4) | 40(2) |
| C(38) | 9309(6) | 3965(5) | −666(4) | 46(2) |
| C(39) | 9024(6) | 3248(5) | −805(4) | 42(2) |
| C(40) | 13338(7) | 3414(4) | 2642(4) | 49(2) |
| C(41) | 12499(7) | 2715(5) | 2861(5) | 67(3) |
| C(42) | 14379(7) | 2937(6) | 2792(4) | 70(3) |
| C(43) | 13501(7) | 3857(6) | 1723(4) | 74(3) |
| C(44) | 13676(7) | 5192(5) | 2887(4) | 49(2) |
| C(45) | 14877(7) | 4923(6) | 2648(5) | 67(3) |
| C(46) | 13520(7) | 5675(5) | 3539(4) | 66(3) |
| C(47) | 13353(7) | 5831(5) | 2156(4) | 65(3) |
| C(48) | 11378(7) | 4511(5) | 3413(4) | 54(2) |
| C(49) | 11030(7) | 5308(6) | 3782(5) | 71(3) |
| C(50) | 10706(6) | 3742(6) | 4034(5) | 70(3) |
| C(51) | 11007(7) | 4730(6) | 2618(5) | 71(3) |
| C(52) | 15278(7) | 2925(6) | 4704(5) | 64(3) |
| C(53) | 15102(7) | 2291(6) | 5480(5) | 64(3) |
| C(54) | 15385(9) | 1379(7) | 5706(6) | 94(4) |
| C(55) | 15101(11) | 969(8) | 6520(7) | 128(5) |
| C(56) | 14628(9) | 1446(8) | 7082(6) | 101(4) |
| C(57) | 14624(6) | 2772(6) | 6049(5) | 55(2) |
| C(57) | 14362(7) | 2322(7) | 6882(5) | 67(3) |
| C(58) | 14524(6) | 3668(6) | 5653(5) | 55(2) |
| C(59) | 14979(7) | 3753(6) | 4839(5) | 61(2) |
| C(60) | 12777(8) | 1772(5) | 5465(5) | 60(2) |
| C(61) | 11694(11) | 1688(6) | 5434(5) | 77(3) |
| C(62) | 10681(10) | 1937(7) | 5870(5) | 89(3) |
| C(63) | 9729(10) | 1793(8) | 5703(6) | 117(5) |
| C(64) | 9760(13) | 1366(9) | 5113(7) | 127(5) |
| C(65) | 10813(12) | 1089(7) | 4653(6) | 109(5) |
| C(66) | 11720(11) | 1271(6) | 4845(5) | 80(3) |
| C(67) | 12847(13) | 1015(7) | 4534(6) | 102(4) |
| C(68) | 13440(10) | 1282(6) | 4912(6) | 87(3) |
| C(69) | 12070(6) | 3695(5) | 5926(4) | 48(2) |
| C(70) | 11994(6) | 3378(5) | 6798(4) | 43(2) |
| C(72) | 11791(6) | 2569(5) | 7340(4) | 58(2) |
| C(73) | 11803(6) | 2452(6) | 8138(4) | 60(2) |
| C(74) | 12023(6) | 3139(6) | 8384(4) | 57(2) |
| C(75) | 12220(7) | 3952(6) | 7858(5) | 60(2) |

TABLE 2-continued

Atomic Coordinates [× 10⁴] and Equivalent Isotropic Displacement Parameters [Å² × 10³]

|  | x | y | z | U(eq) |
|---|---|---|---|---|
| C(76) | 12193(6) | 4078(5) | 7061(4) | 51(2) |
| C(77) | 12309(7) | 4855(5) | 6400(5) | 62(2) |
| C(78) | 12188(7) | 4638(6) | 5753(5) | 61(2) |

TABLE 3

Selected Bond Lengths [Å] and Angles [°]

| Ti(1)—N(1) | 1.786(5) |
|---|---|
| Ti(1)—C(22) | 2.212(7) |
| Ti(1)—C(31) | 2.217(7) |
| Ti(1)—C(13) | 2.323(8) |
| Ti(1)—C(21) | 2.366(7) |
| Ti(1)—C(14) | 2.428(7) |
| Ti(1)—C(20) | 2.586(7) |
| Ti(1)—C(15) | 2.622(7) |
| Ti(2)—N(2) | 1.774(5) |
| Ti(2)—C(69) | 2.205(7) |
| Ti(2)—C(60) | 2.221(8) |
| Ti(2)—C(59) | 2.299(8) |
| Ti(2)—C(52) | 2.359(8) |
| Ti(2)—C(58) | 2.383(7) |
| Ti(2)—C(57) | 2.578(7) |
| Ti(2)—C(53) | 2.596(9) |
| P(1)—N(1) | 1.613(5) |
| P(1)—C(5) | 1.861(8) |
| P(1)—C(9) | 1.888(7) |
| P(1)—C(1) | 1.895(7) |
| P(2)—N(2) | 1.627(5) |
| P(2)—C(48) | 1.858(9) |
| P(2)—C(40) | 1.884(8) |
| P(2)—C(44) | 1.892(8) |
| C(1)—C(4) | 1.545(10) |
| C(1)—C(3) | 1.546(11) |
| C(1)—C(2) | 1.549(10) |
| C(5)—C(7) | 1.520(10) |
| C(5)—C(8) | 1.568(9) |
| C(5)—C(6) | 1.570(10) |
| C(9)—C(10) | 1.524(10) |
| C(9)—C(12) | 1.563(10) |
| C(9)—C(11) | 1.568(8) |
| C(13)—C(14) | 1.399(10) |
| C(13)—C(21) | 1.405(11) |
| C(14)—C(15) | 1.427(9) |
| C(15)—C(20) | 1.409(10) |
| C(15)—C(16) | 1.426(10) |
| C(16)—C(17) | 1.395(11) |
| C(17)—C(18) | 1.383(13) |
| C(18)—C(19) | 1.344(12) |
| C(19)—C(20) | 1.436(10) |
| C(20)—C(21) | 1.417(10) |
| C(22)—C(30) | 1.473(9) |
| C(22)—C(23) | 1.496(9) |
| C(23)—C(28) | 1.392(9) |
| C(23)—C(24) | 1.401(8) |
| C(24)—C(25) | 1.386(9) |
| C(25)—C(26) | 1.378(10) |
| C(26)—C(27) | 1.375(10) |
| C(27)—C(28) | 1.393(9) |
| C(28)—C(29) | 1.454(9) |
| C(29)—C(30) | 1.348(10) |
| C(31)—C(39) | 1.449(9) |
| C(31)—C(32) | 1.472(9) |
| C(32)—C(33) | 1.374(9) |
| C(32)—C(37) | 1.430(9) |
| C(33)—C(34) | 1.362(9) |
| C(34)—C(35) | 1.393(10) |
| C(35)—C(36) | 1.372(10) |
| C(36)—C(37) | 1.380(9) |
| C(37)—C(38) | 1.423(10) |
| C(38)—C(39) | 1.351(9) |

TABLE 3-continued

Selected Bond Lengths [A] and Angles [o]

| | |
|---|---|
| C(40)—C(42) | 1.504(10) |
| C(40)—C(41) | 1.546(10) |
| C(40)—C(43) | 1.568(9) |
| C(44)—C(45) | 1.520(11) |
| C(44)—C(46) | 1.533(10) |
| C(44)—C(47) | 1.540(9) |
| C(48)—C(49) | 1.555(11) |
| C(48)—C(51) | 1.566(9) |
| C(48)—C(50) | 1.567(10) |
| C(52)—C(59) | 1.393(11) |
| C(52)—C(53) | 1.450(10) |
| C(53)—C(57) | 1.409(10) |
| C(53)—C(54) | 1.421(12) |
| C(54)—C(55) | 1.386(13) |
| C(55)—C(56) | 1.394(14) |
| C(56)—C(57) | 1.360(13) |
| C(57)—C(58) | 1.409(11) |
| C(57)—C(57) | 1.430(10) |
| C(58)—C(59) | 1.391(10) |
| C(60)—C(61) | 1.434(13) |
| C(60)—C(68) | 1.454(12) |
| C(61)—C(62) | 1.391(13) |
| C(61)—C(66) | 1.394(12) |
| C(62)—C(63) | 1.400(13) |
| C(63)—C(64) | 1.406(14) |
| C(64)—C(65) | 1.46(2) |
| C(65)—C(66) | 1.392(14) |
| C(66)—C(67) | 1.448(14) |
| C(67)—C(68) | 1.330(13) |
| C(69)—C(78) | 1.463(10) |
| C(69)—C(70) | 1.485(8) |
| C(70)—C(72) | 1.383(10) |
| C(70)—C(76) | 1.405(10) |
| C(72)—C(73) | 1.399(9) |
| C(73)—C(74) | 1.380(11) |
| C(74)—C(75) | 1.377(11) |
| C(75)—C(76) | 1.401(9) |
| C(76)—C(77) | 1.443(10) |
| C(77)—C(78) | 1.360(10) |
| N(1)—Ti(1)—C(22) | 100.1(2) |
| N(1)—Ti(1)—C(31) | 108.1(3) |
| C(22)—Ti(1)—C(31) | 98.0(3) |
| N(1)—Ti(1)—C(13) | 96.7(3) |
| C(22)—Ti(1)—C(13) | 112.0(3) |
| C(31)—Ti(1)—C(13) | 136.9(3) |
| N(1)—Ti(1)—C(21) | 102.1(3) |
| C(22)—Ti(1)—C(21) | 141.9(3) |
| C(31)—Ti(1)—C(21) | 104.0(3) |
| C(13)—Ti(1)—C(21) | 34.9(3) |
| N(1)—Ti(1)—C(14) | 122.9(3) |
| C(22)—Ti(1)—C(14) | 84.8(3) |
| C(31)—Ti(1)—C(14) | 127.7(2) |
| C(13)—Ti(1)—C(14) | 34.2(3) |
| C(21)—Ti(1)—C(14) | 57.1(3) |
| N(1)—Ti(1)—C(20) | 133.5(3) |
| C(22)—Ti(1)—C(20) | 123.5(3) |
| C(31)—Ti(1)—C(20) | 83.2(2) |
| C(13)—Ti(1)—C(20) | 54.7(3) |
| C(21)—Ti(1)—C(20) | 32.9(2) |
| C(14)—Ti(1)—C(20) | 54.3(3) |
| N(1)—Ti(1)—C(15) | 150.9(2) |
| C(22)—Ti(1)—C(15) | 93.2(3) |
| C(31)—Ti(1)—C(15) | 95.4(2) |
| C(13)—Ti(1)—C(15) | 54.3(2) |
| C(21)—Ti(1)—C(15) | 54.4(2) |
| C(14)—Ti(1)—C(15) | 32.5(2) |
| C(20)—Ti(1)—C(15) | 31.4(2) |
| N(2)—Ti(2)—C(69) | 99.3(3) |
| N(2)—Ti(2)—C(60) | 108.1(3) |
| C(69)—Ti(2)—C(60) | 98.2(3) |
| N(2)—Ti(2)—C(59) | 97.2(3) |
| C(69)—Ti(2)—C(59) | 110.6(3) |
| C(60)—Ti(2)—C(59) | 137.8(3) |
| N(2)—Ti(2)—C(52) | 102.9(3) |
| C(69)—Ti(2)—C(52) | 140.6(3) |
| C(60)—Ti(2)—C(52) | 105.2(4) |
| C(59)—Ti(2)—C(52) | 34.8(3) |
| N(2)—Ti(2)—C(58) | 123.4(3) |
| C(69)—Ti(2)—C(58) | 83.2(3) |
| C(60)—Ti(2)—C(58) | 127.7(3) |
| C(59)—Ti(2)—C(58) | 34.5(3) |
| C(52)—Ti(2)—C(58) | 57.4(3) |
| N(2)—Ti(2)—C(57) | 152.0(3) |
| C(69)—Ti(2)—C(57) | 92.2(3) |
| C(60)—Ti(2)—C(57) | 95.3(3) |
| C(59)—Ti(2)—C(57) | 54.7(3) |
| C(52)—Ti(2)—C(57) | 54.9(3) |
| C(58)—Ti(2)—C(57) | 32.7(3) |
| N(2)—Ti(2)—C(53) | 134.8(3) |
| C(69)—Ti(2)—C(53) | 122.8(3) |
| C(60)—Ti(2)—C(53) | 83.3(3) |
| C(59)—Ti(2)—C(53) | 55.4(3) |
| C(52)—Ti(2)—C(53) | 33.6(3) |
| C(58)—Ti(2)—C(53) | 54.8(3) |
| C(57)—Ti(2)—C(53) | 31.6(2) |
| N(1)—P(1)—C(5) | 108.7(3) |
| N(1)—P(1)—C(9) | 107.4(3) |
| C(5)—P(1)—C(9) | 111.7(4) |
| N(1)—P(1)—C(1) | 109.2(3) |
| C(5)—P(1)—C(1) | 110.2(4) |
| C(9)—P(1)—C(1) | 109.5(3) |
| N(2)—P(2)—C(48) | 109.2(3) |
| N(2)—P(2)—C(40) | 107.3(3) |
| C(48)—P(2)—C(40) | 111.7(4) |
| N(2)—P(2)—C(44) | 108.2(3) |
| C(48)—P(2)—C(44) | 110.5(4) |
| C(40)—P(2)—C(44) | 109.8(4) |
| P(1)—N(1)—Ti(1) | 171.6(4) |
| P(2)—N(2)—Ti(2) | 175.2(4) |
| C(4)—C(1)—C(3) | 105.4(7) |
| C(4)—C(1)—C(2) | 109.9(6) |
| C(3)—C(1)—C(2) | 109.2(7) |
| C(4)—C(1)—P(1) | 109.5(5) |
| C(3)—C(1)—P(1) | 109.7(5) |
| C(2)—C(1)—P(1) | 112.7(6) |
| C(7)—C(5)—C(8) | 108.2(6) |
| C(7)—C(5)—C(6) | 106.0(7) |
| C(8)—C(5)—C(6) | 106.0(6) |
| C(7)—C(5)—P(1) | 111.8(6) |
| C(8)—C(5)—P(1) | 114.8(5) |
| C(6)—C(5)—P(1) | 109.5(5) |
| C(10)—C(9)—C(12) | 106.5(6) |
| C(10)—C(9)—C(11) | 111.5(6) |
| C(12)—C(9)—C(11) | 106.7(6) |
| C(10)—C(9)—P(1) | 109.2(5) |
| C(12)—C(9)—P(1) | 108.7(5) |
| C(11)—C(9)—P(1) | 114.0(5) |
| C(14)—C(13)—C(21) | 109.7(7) |
| C(14)—C(13)—Ti(1) | 77.0(4) |
| C(21)—C(13)—Ti(1) | 74.2(5) |
| C(13)—C(14)—C(15) | 106.9(7) |
| C(13)—C(14)—Ti(1) | 68.8(4) |
| C(15)—C(14)—Ti(1) | 81.2(4) |
| C(20)—C(15)—C(16) | 121.2(7) |
| C(20)—C(15)—C(14) | 107.8(7) |
| C(16)—C(15)—C(14) | 130.9(8) |
| C(20)—C(15)—Ti(1) | 72.9(4) |
| C(16)—C(15)—Ti(1) | 128.0(5) |
| C(14)—C(15)—Ti(1) | 66.2(4) |
| C(17)—C(16)—C(15) | 117.4(9) |
| C(18)—C(17)—C(16) | 120.7(9) |
| C(19)—C(18)—C(17) | 123.1(9) |
| C(18)—C(19)—C(20) | 119.1(9) |
| C(15)—C(20)—C(21) | 108.4(7) |
| C(15)—C(20)—C(19) | 118.3(7) |
| C(21)—C(20)—C(19) | 133.2(8) |
| C(15)—C(20)—Ti(1) | 75.7(4) |
| C(21)—C(20)—Ti(1) | 65.0(4) |
| C(19)—C(20)—Ti(1) | 128.9(5) |
| C(13)—C(21)—C(20) | 106.9(8) |
| C(13)—C(21)—Ti(1) | 70.9(5) |
| C(20)—C(21)—Ti(1) | 82.1(4) |
| C(30)—C(22)—C(23) | 102.1(6) |
| C(30)—C(22)—Ti(1) | 113.3(5) |

TABLE 3-continued

Selected Bond Lengths [A] and Angles [o]

| | |
|---|---|
| C(23)—C(22)—Ti(1) | 116.3(5) |
| C(28)—C(23)—C(24) | 119.1(6) |
| C(28)—C(23)—C(22) | 109.2(6) |
| C(24)—C(23)—C(22) | 131.7(7) |
| C(25)—C(24)—C(23) | 118.8(7) |
| C(26)—C(25)—C(24) | 121.5(7) |
| C(27)—C(26)—C(25) | 120.1(7) |
| C(26)—C(27)—C(28) | 119.2(8) |
| C(23)—C(28)—C(27) | 121.0(7) |
| C(23)—C(28)—C(29) | 108.2(6) |
| C(27)—C(28)—C(29) | 130.8(7) |
| C(30)—C(29)—C(28) | 108.2(7) |
| C(29)—C(30)—C(22) | 112.0(6) |
| C(39)—C(31)—C(32) | 104.5(6) |
| C(39)—C(31)—Ti(1) | 106.6(4) |
| C(32)—C(31)—Ti(1) | 117.7(4) |
| C(33)—C(32)—C(37) | 117.6(6) |
| C(33)—C(32)—C(31) | 134.7(7) |
| C(37)—C(32)—C(31) | 107.7(6) |
| C(34)—C(33)—C(32) | 120.8(7) |
| C(33)—C(34)—C(35) | 122.0(8) |
| C(36)—C(35)—C(34) | 118.3(7) |
| C(35)—C(36)—C(37) | 120.6(8) |
| C(36)—C(37)—C(38) | 132.1(8) |
| C(36)—C(37)—C(32) | 120.5(7) |
| C(38)—C(37)—C(32) | 107.3(6) |
| C(39)—C(38)—C(37) | 109.8(7) |
| C(38)—C(39)—C(31) | 110.5(6) |
| C(42)—C(40)—C(41) | 107.1(7) |
| C(42)—C(40)—C(43) | 109.6(7) |
| C(41)—C(40)—C(43) | 106.0(6) |
| C(42)—C(40)—P(2) | 109.5(5) |
| C(41)—C(40)—P(2) | 109.5(5) |
| C(43)—C(40)—P(2) | 114.8(6) |
| C(45)—C(44)—C(46) | 107.0(7) |
| C(45)—C(44)—C(47) | 109.0(6) |
| C(46)—C(44)—C(47) | 108.7(7) |
| C(45)—C(44)—P(2) | 110.3(5) |
| C(46)—C(44)—P(2) | 109.4(5) |
| C(47)—C(44)—P(2) | 112.3(5) |
| C(49)—C(48)—C(51) | 108.1(6) |
| C(49)—C(48)—C(50) | 104.9(7) |
| C(51)—C(48)—C(50) | 108.3(7) |
| C(49)—C(48)—P(2) | 111.8(6) |
| C(51)—C(48)—P(2) | 114.8(5) |
| C(50)—C(48)—P(2) | 108.5(5) |
| C(59)—C(52)—C(53) | 107.4(7) |
| C(59)—C(52)—Ti(2) | 70.3(5) |
| C(53)—C(52)—Ti(2) | 82.2(5) |
| C(57)—C(53)—C(54) | 122.1(8) |
| C(57)—C(53)—C(52) | 106.0(8) |
| C(54)—C(53)—C(52) | 131.7(9) |
| C(57)—C(53)—Ti(2) | 73.5(5) |
| C(54)—C(53)—Ti(2) | 130.5(7) |
| C(52)—C(53)—Ti(2) | 64.2(4) |
| C(55)—C(54)—C(53) | 116.5(10) |
| C(54)—C(55)—C(56) | 121.1(11) |
| C(57)—C(56)—C(55) | 123.5(10) |
| C(53)—C(57)—C(58) | 109.4(7) |
| C(53)—C(57)—C(57) | 119.2(8) |
| C(58)—C(57)—C(57) | 131.4(8) |
| C(53)—C(57)—Ti(2) | 74.9(5) |
| C(58)—C(57)—Ti(2) | 66.0(4) |
| C(57)—C(57)—Ti(2) | 127.2(6) |
| C(56)—C(57)—C(57) | 117.4(9) |
| C(59)—C(58)—C(57) | 107.3(8) |
| C(59)—C(58)—Ti(2) | 69.5(4) |
| C(57)—C(58)—Ti(2) | 81.3(5) |
| C(58)—C(59)—C(52) | 109.6(8) |
| C(58)—C(59)—Ti(2) | 76.0(5) |
| C(52)—C(59)—Ti(2) | 75.0(5) |
| C(61)—C(60)—C(68) | 103.2(9) |
| C(61)—C(60)—Ti(2) | 117.5(6) |
| C(68)—C(60)—Ti(2) | 108.5(6) |
| C(62)—C(61)—C(66) | 117.5(12) |
| C(62)—C(61)—C(60) | 132.5(10) |
| C(66)—C(61)—C(60) | 110.0(11) |
| C(61)—C(62)—C(63) | 120.9(11) |
| C(62)—C(63)—C(64) | 121.4(13) |
| C(63)—C(64)—C(65) | 118.8(12) |
| C(66)—C(65)—C(64) | 116.2(11) |
| C(65)—C(66)—C(61) | 125.2(13) |
| C(65)—C(66)—C(67) | 128.0(11) |
| C(61)—C(66)—C(67) | 106.7(11) |
| C(68)—C(67)—C(66) | 108.1(11) |
| C(67)—C(68)—C(60) | 111.6(11) |
| C(78)—C(69)—C(70) | 103.3(6) |
| C(78)—C(69)—Ti(2) | 110.4(5) |
| C(70)—C(69)—Ti(2) | 118.6(5) |
| C(72)—C(70)—C(76) | 119.3(6) |
| C(72)—C(70)—C(69) | 132.4(7) |
| C(76)—C(70)—C(69) | 108.3(7) |
| C(70)—C(72)—C(73) | 119.9(8) |
| C(74)—C(73)—C(72) | 120.2(8) |
| C(75)—C(74)—C(73) | 121.0(7) |
| C(74)—C(75)—C(76) | 119.0(8) |
| C(75)—C(76)—C(70) | 120.5(7) |
| C(75)—C(76)—C(77) | 131.0(8) |
| C(70)—C(76)—C(77) | 108.5(6) |
| C(78)—C(77)—C(76) | 108.1(8) |
| C(77)—C(78)—C(69) | 111.3(7) |

TABLE 4

Anisotropic Displacement Parameters [A$^2$ × 10$^3$]

| | U11 | U22 | U33 | U23 | U13 | U12 |
|---|---|---|---|---|---|---|
| Ti(1) | 48(1) | 27(1) | 29(1) | −3(1) | −13(1) | −7(1) |
| Ti(2) | 54(1) | 38(1) | 25(1) | 4(1) | −12(1) | −14(1) |
| P(1) | 49(1) | 31(1) | 30(1) | −3(1) | −15(1) | −8(1) |
| P(2) | 51(1) | 43(1) | 21(1) | 5(1) | −10(1) | −16(1) |
| N(1) | 38(4) | 28(3) | 34(3) | −5(2) | −16(3) | −2(3) |
| N(2) | 50(4) | 39(4) | 21(3) | 1(2) | −10(3) | −5(3) |
| C(1) | 99(8) | 38(5) | 29(4) | 20(3) | −27(5) | −29(5) |
| C(2) | 144(10) | 70(7) | 58(6) | 22(5) | −55(6) | −36(7) |
| C(3) | 109(9) | 86(7) | 38(5) | −5(5) | 4(5) | −58(5) |
| C(4) | 138(9) | 38(5) | 56(5) | 17(4) | −46(6) | −40(5) |
| C(5) | 53(6) | 51(5) | 48(5) | −16(4) | −24(4) | −1(4) |
| C(6) | 50(6) | 88(7) | 56(5) | −25(5) | −10(4) | 2(5) |
| C(7) | 90(8) | 54(6) | 120(8) | −50(6) | −60(6) | 31(6) |
| C(8) | 51(6) | 94(8) | 82(6) | −40(6) | −30(5) | 1(5) |
| C(9) | 55(6) | 33(4) | 29(4) | −2(3) | −13(3) | −12(4) |
| C(10) | 69(7) | 46(5) | 68(6) | −29(4) | −16(5) | 5(5) |
| C(11) | 83(7) | 61(6) | 45(5) | −24(4) | −22(4) | −13(5) |
| C(12) | 72(6) | 35(5) | 56(5) | −2(4) | −16(4) | −15(4) |
| C(13) | 88(8) | 40(5) | 48(5) | −10(4) | −27(5) | 2(5) |
| C(14) | 75(7) | 26(4) | 40(4) | −9(3) | −12(4) | −12(4) |
| C(15) | 46(6) | 38(5) | 53(5) | −24(4) | −17(4) | 6(4) |
| C(16) | 64(6) | 47(5) | 59(6) | −32(4) | −19(5) | 1(4) |
| C(17) | 108(10) | 75(7) | 57(6) | −33(6) | −39(6) | 14(7) |
| C(18) | 116(10) | 73(7) | 37(5) | −21(5) | −11(6) | −1(7) |
| C(19) | 68(7) | 53(6) | 66(6) | −36(5) | 1(5) | −9(5) |
| C(20) | 58(6) | 38(5) | 40(5) | −18(4) | −4(4) | −3(4) |
| C(21) | 53(6) | 53(5) | 63(6) | −35(5) | −22(5) | 13(5) |
| C(22) | 42(5) | 37(4) | 35(4) | −5(3) | −11(3) | −1(4) |
| C(23) | 33(5) | 34(4) | 37(4) | −2(3) | −11(3) | 0(4) |
| C(24) | 36(5) | 34(4) | 45(4) | −9(3) | −11(4) | −4(4) |
| C(25) | 56(6) | 40(5) | 54(5) | −8(4) | −25(4) | −4(4) |
| C(26) | 67(7) | 48(5) | 75(6) | −17(5) | −40(5) | 2(5) |
| C(27) | 43(5) | 45(5) | 70(6) | −13(4) | −17(4) | −17(4) |
| C(28) | 42(5) | 39(5) | 48(5) | 0(4) | −9(4) | −11(4) |
| C(29) | 60(6) | 47(5) | 43(5) | 14(4) | −11(4) | −21(4) |
| C(30) | 55(6) | 46(5) | 37(4) | 2(4) | −15(4) | −6(4) |
| C(31) | 38(5) | 38(4) | 28(4) | 0(3) | −13(3) | 1(4) |
| C(32) | 44(5) | 21(4) | 24(4) | 3(3) | −9(3) | −5(4) |
| C(33) | 44(5) | 32(4) | 38(4) | −8(3) | −12(4) | 0(4) |
| C(34) | 58(6) | 44(5) | 34(4) | 0(4) | −10(4) | 1(4) |
| C(35) | 70(7) | 27(4) | 48(5) | −9(4) | −17(4) | 1(5) |
| C(36) | 65(6) | 38(5) | 43(5) | −1(4) | −18(4) | −18(4) |
| C(37) | 66(6) | 23(4) | 27(4) | 3(3) | −9(4) | −15(4) |

TABLE 4-continued

Anisotropic Displacement Parameters [A² × 10³]

| | U11 | U22 | U33 | U23 | U13 | U12 |
|---|---|---|---|---|---|---|
| C(38) | 52(6) | 39(5) | 38(4) | 2(4) | −4(4) | −17(4) |
| C(39) | 45(5) | 42(5) | 30(4) | −7(3) | −3(4) | 9(4) |
| C(40) | 67(6) | 56(5) | 27(4) | −6(4) | −16(4) | −18(5) |
| C(41) | 91(7) | 59(6) | 57(5) | −13(4) | −19(5) | −27(5) |
| C(42) | 76(7) | 87(7) | 42(5) | −18(5) | −12(5) | 8(6) |
| C(43) | 103(8) | 86(7) | 22(4) | −4(4) | −4(4) | −16(6) |
| C(44) | 63(6) | 47(5) | 32(4) | 9(3) | −13(4) | −31(4) |
| C(45) | 56(7) | 81(7) | 56(5) | 6(5) | −13(5) | −36(5) |
| C(46) | 98(8) | 51(5) | 52(5) | 5(4) | −29(5) | −35(5) |
| C(47) | 92(7) | 55(6) | 40(5) | 21(4) | −28(5) | −31(5) |
| C(48) | 68(6) | 52(5) | 35(4) | 10(4) | −15(4) | −15(5) |
| C(49) | 69(7) | 83(7) | 63(6) | −18(5) | −24(5) | 1(6) |
| C(50) | 43(6) | 94(7) | 57(6) | 10(5) | −8(4) | −24(5) |
| C(51) | 67(7) | 83(7) | 55(5) | 10(5) | −32(5) | −5(5) |
| C(52) | 48(6) | 94(8) | 39(5) | −9(5) | −8(4) | 4(5) |
| C(53) | 78(7) | 66(6) | 40(5) | −2(4) | −15(5) | 6(5) |
| C(54) | 103(9) | 75(8) | 87(8) | −5(6) | −31(7) | 30(7) |
| C(55) | 173(14) | 93(10) | 86(9) | 14(8) | −41(9) | 35(9) |
| C(56) | 98(10) | 117(11) | 56(7) | 17(7) | −22(6) | 19(8) |
| C(57) | 41(6) | 77(7) | 41(5) | −3(5) | −17(4) | 4(5) |
| C(57) | 45(6) | 103(8) | 47(5) | −10(5) | −16(5) | 5(6) |
| C(58) | 44(6) | 76(7) | 52(5) | −11(5) | −22(4) | −16(5) |
| C(59) | 57(6) | 60(6) | 56(6) | 15(5) | −20(5) | −28(5) |
| C(60) | 88(8) | 48(5) | 40(5) | 10(4) | −20(5) | −28(5) |
| C(61) | 122(11) | 43(6) | 53(6) | 14(5) | −14(6) | −39(6) |
| C(62) | 127(11) | 85(8) | 55(6) | 9(5) | −30(7) | −54(8) |
| C(63) | 136(11) | 166(13) | 62(7) | −28(8) | −12(7) | −87(9) |
| C(64) | 168(15) | 150(13) | 79(9) | −18(8) | −34(9) | −83(11) |
| C(65) | 206(15) | 81(8) | 56(7) | 11(6) | −51(8) | −89(10) |
| C(66) | 145(11) | 48(6) | 48(6) | 2(5) | −28(7) | −38(7) |
| C(67) | 184(15) | 50(7) | 65(7) | −4(5) | −26(9) | −18(8) |
| C(68) | 140(11) | 52(6) | 60(7) | 5(5) | −24(7) | −20(7) |
| C(69) | 46(5) | 70(6) | 25(4) | −7(4) | −8(4) | −10(4) |
| C(70) | 49(5) | 53(5) | 24(4) | −6(4) | −8(3) | −3(4) |
| C(72) | 71(7) | 58(6) | 45(5) | −8(4) | −11(4) | −23(5) |
| C(73) | 61(6) | 78(7) | 30(5) | 7(4) | −4(4) | −25(5) |
| C(74) | 60(6) | 79(7) | 26(4) | −3(4) | −9(4) | −10(5) |
| C(75) | 68(7) | 73(6) | 45(5) | −22(5) | −16(4) | −5(5) |
| C(76) | 57(6) | 56(5) | 30(4) | −4(4) | −7(4) | 2(4) |
| C(77) | 87(7) | 47(5) | 50(5) | −12(5) | −16(5) | −5(5) |
| C(78) | 76(7) | 56(6) | 43(5) | −7(4) | −10(4) | 1(5) |

TABLE 5

Hydrogen Coordinates (× 10⁴) and Isotropic Displacement Parameters (A² × 10³)

| | x | y | z | U(eq) |
|---|---|---|---|---|
| H(2A) | 9034(8) | 1148(6) | 3592(5) | 134 |
| H(2B) | 9592(8) | 390(6) | 3197(5) | 134 |
| H(2C) | 8544(8) | 224(6) | 3907(5) | 134 |
| H(3A) | 7140(8) | 1780(6) | 3422(5) | 120 |
| H(3B) | 6741(8) | 824(6) | 3709(5) | 120 |
| H(3C) | 6616(8) | 1438(6) | 2883(5) | 120 |
| H(4A) | 8671(8) | −110(5) | 2320(5) | 114 |
| H(4B) | 7527(8) | 312(5) | 2227(5) | 114 |
| H(4C) | 7653(8) | −301(5) | 3053(5) | 114 |
| H(6A) | 10607(7) | 2690(6) | 626(4) | 97 |
| H(6B) | 10318(7) | 1951(6) | 311(4) | 97 |
| H(6C) | 11472(7) | 1933(6) | 451(4) | 97 |
| H(7A) | 10033(8) | 442(5) | 1209(6) | 118 |
| H(7B) | 10324(8) | 191(5) | 2038(6) | 118 |
| H(7C) | 11236(8) | 458(5) | 1241(6) | 118 |
| H(8A) | 10935(7) | 2297(6) | 2035(5) | 105 |
| H(8B) | 11792(7) | 1584(6) | 1747(5) | 105 |
| H(8C) | 10879(7) | 1317(6) | 2544(5) | 105 |
| H(10A) | 6945(7) | 2893(5) | 2542(5) | 89 |
| H(10B) | 7339(7) | 3318(5) | 1619(5) | 89 |
| H(10C) | 7349(7) | 3848(5) | 2228(5) | 89 |
| H(11A) | 9591(7) | 2656(5) | 2946(4) | 89 |
| H(11B) | 8365(7) | 2526(5) | 3394(5) | 89 |
| H(11C) | 8784(7) | 3474(5) | 3020(4) | 89 |
| H(12A) | 10122(7) | 3360(5) | 1456(4) | 83 |
| H(12B) | 9255(7) | 4133(5) | 1572(4) | 83 |
| H(12C) | 9245(7) | 3603(5) | 963(4) | 83 |
| H(13A) | 8474(8) | −45(5) | 865(5) | 69 |
| H(14A) | 6649(7) | 137(4) | 544(4) | 56 |
| H(16A) | 5985(7) | 1091(5) | −899(5) | 63 |
| H(17A) | 6675(10) | 1859(6) | −2233(6) | 90 |
| H(18A) | 8431(10) | 2261(6) | −2679(5) | 92 |
| H(19A) | 9579(7) | 1935(5) | −1877(5) | 73 |
| H(21A) | 9809(7) | 900(5) | −284(5) | 62 |
| H(22A) | 5791(6) | 2511(5) | 1146(4) | 46 |
| H(24A) | 5486(6) | 3118(4) | −494(4) | 46 |
| H(25A) | 4299(6) | 2849(5) | −1146(5) | 58 |
| H(26A) | 3298(7) | 1627(5) | −634(5) | 71 |
| H(27A) | 3453(6) | 643(5) | 557(5) | 61 |
| H(29A) | 4450(6) | 313(5) | 1859(4) | 65 |
| H(30A) | 5778(6) | 1065(5) | 2108(4) | 57 |
| H(31A) | 7540(6) | 3144(4) | −905(4) | 43 |
| H(33A) | 5841(6) | 3936(4) | 249(4) | 46 |
| H(35A) | 7102(7) | 6022(5) | 423(4) | 58 |
| H(36A) | 8825(7) | 5478(5) | −101(4) | 58 |
| H(38A) | 10013(6) | 4143(5) | −802(4) | 55 |
| H(39A) | 9502(6) | 2877(5) | −1075(4) | 50 |
| H(41A) | 11821(7) | 2997(5) | 2773(5) | 101 |
| H(41B) | 12397(7) | 2401(5) | 3415(5) | 101 |
| H(41C) | 12759(7) | 2313(5) | 2532(5) | 101 |
| H(42A) | 14922(7) | 3352(6) | 2662(4) | 106 |
| H(42B) | 14621(7) | 2533(6) | 2464(4) | 106 |
| H(42C) | 14259(7) | 2621(6) | 3347(4) | 106 |
| H(43A) | 12836(7) | 4162(6) | 1629(4) | 111 |
| H(43B) | 13706(7) | 3415(6) | 1433(4) | 111 |
| H(43C) | 14062(7) | 4266(6) | 1545(4) | 111 |
| H(45A) | 15007(7) | 4617(6) | 2239(5) | 100 |
| H(45B) | 15091(7) | 4546(6) | 3108(5) | 100 |
| H(45C) | 15290(7) | 5437(6) | 2447(5) | 100 |
| H(46A) | 12767(7) | 5856(5) | 3706(4) | 99 |
| H(46B) | 13946(7) | 6182(5) | 3329(4) | 99 |
| H(46C) | 13747(7) | 5291(5) | 3989(4) | 99 |
| H(47A) | 12595(7) | 6004(5) | 2303(4) | 97 |
| H(47B) | 13491(7) | 5548(5) | 1731(4) | 97 |
| H(47C) | 13771(7) | 6341(5) | 1979(4) | 97 |
| H(49A) | 11251(7) | 5187(6) | 4271(5) | 107 |
| H(49B) | 10256(7) | 5409(6) | 3893(5) | 107 |
| H(49C) | 11370(7) | 5820(6) | 3411(5) | 107 |
| H(50A) | 10882(6) | 3223(6) | 3842(5) | 105 |
| H(50B) | 9945(6) | 3900(6) | 4099(5) | 105 |
| H(50C) | 10879(6) | 3630(6) | 4540(5) | 105 |
| H(51A) | 11214(7) | 4246(6) | 2379(5) | 106 |
| H(51B) | 11346(7) | 5245(6) | 2253(5) | 106 |
| H(51C) | 10233(7) | 4835(6) | 2734(5) | 106 |
| H(52A) | 15703(7) | 2810(5) | 4195(5) | 76 |
| H(54A) | 15743(9) | 1073(7) | 5329(6) | 113 |
| H(55A) | 15227(11) | 365(8) | 6693(7) | 154 |
| H(56A) | 14486(9) | 1150(8) | 7622(6) | 121 |
| H(57A) | 14024(7) | 2616(6) | 7272(5) | 80 |
| H(58A) | 14330(6) | 4151(6) | 5912(5) | 66 |
| H(59A) | 15186(7) | 4308(6) | 4441(5) | 73 |
| H(60A) | 12855(8) | 1481(5) | 6006(5) | 72 |
| H(62A) | 10636(10) | 2201(7) | 6277(6) | 107 |
| H(63A) | 9063(10) | 1985(8) | 5988(6) | 141 |
| H(64A) | 9121(13) | 1262(9) | 5016(7) | 153 |
| H(65A) | 10874(12) | 806(7) | 4256(6) | 131 |
| H(67A) | 13109(13) | 716(7) | 4138(6) | 122 |
| H(68A) | 14186(10) | 1169(6) | 4834(6) | 105 |
| H(69A) | 11373(6) | 3615(5) | 5841(4) | 58 |
| H(72A) | 11646(6) | 2104(5) | 7175(4) | 70 |
| H(73A) | 11663(6) | 1908(6) | 8504(4) | 72 |
| H(74A) | 12039(6) | 3051(6) | 8914(4) | 68 |
| H(75A) | 12368(7) | 4412(6) | 8028(5) | 72 |
| H(77A) | 12444(7) | 5409(5) | 6414(5) | 74 |
| H(78B) | 12181(7) | 5036(6) | 5263(5) | 73 |

TABLE 1

Crystal Data and Structure Refinement

| | |
|---|---|
| Empirical formula | $C_{70}H_{92}N_2P_2Ti$ |
| Formula weight | 1119.20 |
| Temperature | 293(2) K |
| Wavelength | 0.71073 |
| Crystal system | monoclinic |
| Space group | Pn |
| Unit cell dimensions | |
| a = 12.658(3) | alpha = 90 |
| b = 19.658(4) | beta = 99.97(2) |
| c = 12.716(4) | gamma = 90 |
| Volume, Z | 3116.4(14), 2 |
| Density (calculated) | 1.193 $Mg/m^3$ |
| Absorption coefficient | 0.349 $mm^{-1}$ |
| Crystal size | 0.33 × 0.29 × 0.24 mm |
| range for data collection | 1.93 to 22.50 |
| Limiting indices | −16 < h < 16, −22 < k < 26, −9 < I < 16 |
| Reflections collected | 11368 |
| Independent reflections | 6009 (R&Vint&0 = 0.1288) |
| Refinement method | Full-matrix least-squares on $F^2$ |
| Data/restraints/parameters | 6000/2/359 |
| Goodness-of-fit | 0.991 |
| Final R indices [I > 2&Gs(I)] | R1 = 0.0938, wR2 = 0.1935 |
| R indices (all data) | R1 = 0.2019, wR2 = 0.2484 |
| Absolute structure parameter | 0.26(14) |
| Largest diff. peak and hole | 0.397 and −0.458 |

TABLE 2

Atomic Coordinates and Equivalent Isotropic Displacement Parameters

| | x | y | z | U(eq) |
|---|---|---|---|---|
| Ti(1) | 1643(2) | 4371(2) | 2619(3) | 52(1) |
| Ti(2) | 4061(3) | 9375(2) | −840(3) | 46(1) |
| P(1) | 2249(4) | 5913(3) | 1699(5) | 50(2) |
| P(2) | 3417(5) | 10926(3) | 82(5) | 43(2) |
| N(1) | 2024(13) | 5171(7) | 2156(15) | 41(5) |
| N(2) | 3664(13) | 10166(9) | −306(14) | 45(5) |
| C(1) | 405(16) | 3589(10) | 3368(19) | 70(7) |
| C(2) | 35(16) | 3675(11) | 2263(17) | 65(7) |
| C(3) | −223(18) | 4333(11) | 2077(22) | 75(7) |
| C(4) | −27(15) | 4698(11) | 2991(17) | 62(6) |
| C(5) | 327(14) | 4219(10) | 3729(17) | 60(6) |
| C(6) | 1540(20) | 6561(12) | 2465(21) | 66(7) |
| C(7) | 309(18) | 6569(12) | 1908(20) | 60(7) |
| C(8) | 1958(16) | 7307(10) | 2397(19) | 56(6) |
| C(9) | 1591(18) | 6376(10) | 3576(17) | 46(6) |
| C(10) | 1913(18) | 5963(11) | 230(18) | 51(6) |
| C(11) | 745(21) | 5531(13) | −86(23) | 70(8) |
| C(12) | 2517(18) | 5597(11) | −381(20) | 67(7) |
| C(13) | 1750(22) | 6701(13) | −221(24) | 87(10) |
| C(14) | 3770(21) | 6113(13) | 2037(22) | 67(8) |
| C(15) | 4123(21) | 6197(13) | 3313(21) | 72(8) |
| C(16) | 4113(23) | 6759(13) | 1494(24) | 87(9) |
| C(17) | 4379(19) | 5451(11) | 1725(20) | 72(8) |
| C(18) | 2297(18) | 3542(11) | 1666(18) | 49(6) |
| C(19) | 3361(13) | 3688(8) | 1449(14) | 27(5) |
| C(20) | 4343(24) | 3558(14) | 2162(26) | 81(9) |
| C(21) | 5268(22) | 3781(12) | 1708(23) | 75(8) |
| C(22) | 5206(25) | 3923(13) | 737(24) | 72(8) |
| C(23) | 4280(26) | 3997(15) | 20(29) | 94(10) |
| C(24) | 3369(18) | 3858(11) | 387(19) | 54(6) |
| C(25) | 2116(15) | 3773(9) | −41(17) | 45(5) |
| C(26) | 1589(24) | 3589(13) | 736(23) | 89(10) |
| C(27) | 2903(16) | 4235(9) | 4099(16) | 30(5) |
| C(28) | 2852(17) | 3581(8) | 4638(17) | 46(6) |
| C(29) | 3017(23) | 2901(9) | 4419(21) | 67(7) |
| C(30) | 2824(19) | 2396(14) | 5017(21) | 87(9) |
| C(31) | 2499(14) | 2525(9) | 5972(16) | 54(5) |
| C(32) | 2361(16) | 3164(11) | 6326(19) | 67(7) |
| C(33) | 2545(15) | 3687(10) | 5652(17) | 56(6) |
| C(34) | 2484(16) | 4406(11) | 5780(20) | 73(7) |

TABLE 2-continued

Atomic Coordinates and Equivalent Isotropic Displacement Parameters

| | x | y | z | U(eq) |
|---|---|---|---|---|
| C(35) | 2797(18) | 4756(13) | 4836(19) | 61(7) |
| C(36) | 5258(13) | 8765(9) | −1877(14) | 41(5) |
| C(37) | 5398(12) | 9500(8) | −1991(15) | 46(5) |
| C(38) | 5871(13) | 9703(9) | −862(14) | 40(5) |
| C(39) | 5902(15) | 9168(9) | −163(17) | 46(5) |
| C(40) | 5542(14) | 8564(9) | −790(16) | 46(5) |
| C(41) | 1938(17) | 11076(10) | −300(18) | 39(6) |
| C(42) | 1539(21) | 11676(12) | 326(21) | 71(8) |
| C(43) | 1320(18) | 10462(10) | −154(18) | 59(6) |
| C(44) | 1705(22) | 11255(13) | −1460(21) | 81(9) |
| C(45) | 4271(16) | 11564(10) | −505(16) | 42(6) |
| C(46) | 4235(23) | 11350(14) | −1725(23) | 90(10) |
| C(47) | 3917(19) | 12286(12) | −440(21) | 86(9) |
| C(48) | 5449(22) | 11498(15) | −1(25) | 101(11) |
| C(49) | 3924(19) | 10956(11) | 1582(19) | 53(7) |
| C(50) | 4069(22) | 11685(12) | 2027(23) | 81(9) |
| C(51) | 2929(18) | 10590(11) | 2110(20) | 75(7) |
| C(52) | 4595(21) | 10572(13) | 1893(23) | 70(8) |
| C(53) | 3530(18) | 8546(12) | 94(20) | 60(7) |
| C(54) | 2430(19) | 8601(10) | 205(18) | 60(7) |
| C(55) | 1387(19) | 8601(11) | −356(21) | 57(7) |
| C(56) | 420(21) | 8668(12) | −26(21) | 68(8) |
| C(57) | 485(26) | 8956(13) | 1106(24) | 84(9) |
| C(58) | 1505(20) | 8974(12) | 1759(23) | 57(7) |
| C(59) | 2457(17) | 8792(11) | 1330(19) | 50(6) |
| C(60) | 3383(17) | 8824(10) | 1989(20) | 69(7) |
| C(61) | 4099(17) | 8607(10) | 1247(17) | 47(6) |
| C(62) | 2850(20) | 9289(11) | −2276(19) | 56(7) |
| C(63) | 2891(17) | 8676(9) | −2944(17) | 49(6) |
| C(64) | 2729(20) | 7994(9) | −2733(21) | 68(7) |
| C(65) | 2887(17) | 7465(12) | −3497(20) | 68(7) |
| C(66) | 3203(16) | 7743(11) | −4464(19) | 74(7) |
| C(67) | 3314(18) | 8384(11) | −4649(21) | 83(8) |
| C(68) | 3145(14) | 8896(10) | −3951(15) | 45(5) |
| C(69) | 3179(14) | 9593(10) | −3951(17) | 53(6) |
| C(70) | 2998(18) | 9804(13) | −3048(21) | 68(8) |

TABLE 3

Selected Bond Lengths and Angles

| | |
|---|---|
| Ti(1)—N(1) | 1.77(2) |
| Ti(1)—C(27) | 2.26(2) |
| Ti(1)—C(18) | 2.27(2) |
| Ti(1)—C(4) | 2.34(2) |
| Ti(1)—C(3) | 2.35(2) |
| Ti(1)—C(5) | 2.38(2) |
| Ti(1)—C(2) | 2.43(2) |
| Ti(1)—C(1) | 2.50(2) |
| Ti(2)—N(2) | 1.80(2) |
| Ti(2)—C(62) | 2.18(2) |
| Ti(2)—C(53) | 2.19(2) |
| Ti(2)—C(39) | 2.37(2) |
| Ti(2)—C(38) | 2.38(2) |
| Ti(2)—C(37) | 2.43(2) |
| Ti(2)—C(40) | 2.45(2) |
| Ti(2)—C(36) | 2.48(2) |
| P(1)—N(1) | 1.61(2) |
| P(1)—C(10) | 1.84(2) |
| P(1)—C(6) | 1.92(3) |
| P(1)—C(14) | 1.94(3) |
| P(2)—N(2) | 1.62(2) |
| P(2)—C(41) | 1.87(2) |
| P(2)—C(45) | 1.89(2) |
| P(2)—C(49) | 1.90(2) |
| C(1)—C(5) | 1.33(3) |
| C(1)—C(2) | 1.41(3) |
| C(2)—C(3) | 1.35(3) |
| C(3)—C(4) | 1.35(3) |
| C(4)—C(5) | 1.35(3) |
| C(6)—C(9) | 1.45(3) |

TABLE 3-continued

Selected Bond Lengths and Angles

| | |
|---|---|
| C(6)—C(8) | 1.57(3) |
| C(6)—C(7) | 1.60(3) |
| C(10)—C(12) | 1.38(3) |
| C(10)—C(13) | 1.56(3) |
| C(10)—C(11) | 1.69(3) |
| C(14)—C(16) | 1.54(3) |
| C(14)—C(17) | 1.60(3) |
| C(14)—C(15) | 1.62(4) |
| C(18)—C(26) | 1.36(4) |
| C(18)—C(19) | 1.45(3) |
| C(19)—C(24) | 1.39(3) |
| C(19)—C(20) | 1.43(3) |
| C(20)—C(21) | 1.46(4) |
| C(21)—C(22) | 1.25(3) |
| C(22)—C(23) | 1.36(4) |
| C(23)—C(24) | 1.34(4) |
| C(24)—C(25) | 1.59(3) |
| C(25)—C(26) | 1.33(3) |
| C(27)—C(35) | 1.41(3) |
| C(27)—C(28) | 1.46(3) |
| C(28)—C(29) | 1.39 |
| C(28)—C(33) | 1.43(3) |
| C(29)—C(30) | 1.30(3) |
| C(30)—C(31) | 1.37(3) |
| C(31)—C(32) | 1.36(3) |
| C(32)—C(33) | 1.38(3) |
| C(33)—C(34) | 1.43(3) |
| C(34)—C(35) | 1.50(3) |
| C(36)—C(40) | 1.42(3) |
| C(36)—C(37) | 1.47(2) |
| C(37)—C(38) | 1.51(3) |
| C(38)—C(39) | 1.37(3) |
| C(39)—C(40) | 1.46(3) |
| C(41)—C(43) | 1.47(3) |
| C(41)—C(44) | 1.50(3) |
| C(41)—C(42) | 1.56(3) |
| C(45)—C(47) | 1.50(3) |
| C(45)—C(48) | 1.52(3) |
| C(45)—C(46) | 1.60(3) |
| C(49)—C(52) | 1.44(3) |
| C(49)—C(50) | 1.54(3) |
| C(49)—C(51) | 1.69(3) |
| C(53)—C(54) | 1.43(3) |
| C(53)—C(61) | 1.52(3) |
| C(54)—C(55) | 1.39(3) |
| C(54)—C(59) | 1.47(3) |
| C(55)—C(56) | 1.37(3) |
| C(56)—C(57) | 1.54(4) |
| C(57)—C(58) | 1.41(3) |
| C(58)—C(59) | 1.45(3) |
| C(59)—C(60) | 1.32(3) |
| C(60)—C(61) | 1.48(3) |
| C(62)—C(70) | 1.44(3) |
| C(62)—C(63) | 1.48(3) |
| C(63)—C(64) | 1.39 |
| C(63)—C(68) | 1.44(3) |
| C(64)—C(65) | 1.46(3) |
| C(65)—C(66) | 1.46(3) |
| C(66)—C(67) | 1.29(3) |
| C(67)—C(68) | 1.38(3) |
| C(68)—C(69) | 1.37(3) |
| C(69)—C(70) | 1.28(3) |
| N(1)—Ti(1)—C(27) | 100.9(7) |
| N(1)—Ti(1)—C(18) | 108.3(8) |
| C(27)—Ti(1)—C(18) | 95.1(8) |
| N(1)—Ti(1)—C(4) | 97.5(7) |
| C(27)—Ti(1)—C(4) | 113.4(8) |
| C(18)—Ti(1)—C(4) | 137.0(8) |
| N(1)—Ti(1)—C(3) | 104.4(7) |
| C(27)—Ti(1)—C(3) | 140.3(9) |
| C(18)—Ti(1)—C(3) | 105.2(8) |
| C(4)—Ti(1)—C(3) | 33.6(7) |
| N(1)—Ti(1)—C(5) | 124.5(7) |
| C(27)—Ti(1)—C(5) | 87.5(7) |
| C(18)—Ti(1)—C(5) | 125.6(8) |
| C(4)—Ti(1)—C(5) | 33.2(6) |
| C(3)—Ti(1)—C(5) | 52.9(8) |
| N(1)—Ti(1)—C(2) | 134.7(7) |
| C(27)—Ti(1)—C(2) | 122.4(7) |
| C(18)—Ti(1)—C(2) | 82.3(7) |
| C(4)—Ti(1)—C(2) | 55.5(7) |
| C(3)—Ti(1)—C(2) | 32.7(7) |
| C(5)—Ti(1)—C(2) | 52.4(7) |
| N(1)—Ti(1)—C(1) | 153.6(7) |
| C(27)—Ti(1)—C(1) | 90.5(7) |
| C(18)—Ti(1)—C(1) | 94.1(8) |
| C(4)—Ti(1)—C(1) | 56.1(7) |
| C(3)—Ti(1)—C(1) | 55.0(8) |
| C(5)—Ti(1)—C(1) | 31.5(6) |
| C(2)—Ti(1)—C(1) | 33.3(7) |
| N(2)—Ti(2)—C(62) | 100.4(8) |
| N(2)—Ti(2)—C(53) | 107.8(9) |
| C(62)—Ti(2)—C(53) | 99.2(9) |
| N(2)—Ti(2)—C(39) | 109.3(7) |
| C(62)—Ti(2)—C(39) | 142.6(8) |
| C(53)—Ti(2)—C(39) | 92.8(8) |
| N(2)—Ti(2)—C(38) | 95.9(7) |
| C(62)—Ti(2)—C(38) | 123.3(8) |
| C(53)—Ti(2)—C(38) | 126.4(8) |
| C(39)—Ti(2)—C(38) | 33.5(6) |
| N(2)—Ti(2)—C(37) | 114.1(7) |
| C(62)—Ti(2)—C(37) | 88.0(8) |
| C(53)—Ti(2)—C(37) | 135.4(8) |
| C(39)—Ti(2)—C(37) | 59.7(7) |
| C(38)—Ti(2)—C(37) | 36.5(6) |
| N(2)—Ti(2)—C(40) | 144.3(7) |
| C(62)—Ti(2)—C(40) | 113.3(8) |
| C(53)—Ti(2)—C(40) | 78.9(8) |
| C(39)—Ti(2)—C(40) | 35.1(6) |
| C(38)—Ti(2)—C(40) | 56.3(6) |
| C(37)—Ti(2)—C(40) | 58.2(6) |
| N(2)—Ti(2)—C(36) | 148.5(7) |
| C(62)—Ti(2)—C(36) | 85.6(8) |
| C(53)—Ti(2)—C(36) | 101.6(8) |
| C(39)—Ti(2)—C(36) | 57.3(6) |
| C(38)—Ti(2)—C(36) | 56.5(6) |
| C(37)—Ti(2)—C(36) | 34.7(5) |
| C(40)—Ti(2)—C(36) | 33.5(6) |
| N(1)—P(1)—C(10) | 112.9(9) |
| N(1)—P(1)—C(6) | 106.9(10) |
| C(10)—P(1)—C(6) | 115.6(10) |
| N(1)—P(1)—C(14) | 109.5(10) |
| C(10)—P(1)—C(14) | 105.1(11) |
| C(6)—P(1)—C(14) | 106.6(11) |
| N(2)—P(2)—C(41) | 107.6(9) |
| N(2)—P(2)—C(45) | 109.7(9) |
| C(41)—P(2)—C(45) | 114.0(9) |
| N(2)—P(2)—C(49) | 106.6(9) |
| C(41)—P(2)—C(49) | 113.8(10) |
| C(45)—P(2)—C(49) | 104.9(9) |
| P(1)—N(1)—Ti(1) | 174.5(11) |
| P(2)—N(2)—TI(2) | 172.3(12) |
| C(5)—C(1)—C(2) | 102(2) |
| C(5)—C(1)—Ti(1) | 69.4(12) |
| C(2)—C(1)—Ti(1) | 70.7(12) |
| C(3)—C(2)—C(1) | 108(2) |
| C(3)—C(2)—Ti(1) | 70.2(12) |
| C(1)—C(2)—Ti(1) | 76.0(12) |
| C(2)—C(3)—C(4) | 111(2) |
| C(2)—C(3)—Ti(1) | 77.2(13) |
| C(4)—C(3)—Ti(1) | 72.8(13) |
| C(3)—C(4)—C(5) | 103(2) |
| C(3)—C(4)—Ti(1) | 73.6(13) |
| C(5)—C(4)—Ti(1) | 75.3(12) |
| C(1)—C(5)—C(4) | 116(2) |
| C(1)—C(5)—Ti(1) | 79.1(13) |
| C(4)—C(5)—Ti(1) | 71.5(12) |
| C(9)—C(6)—C(8) | 109(2) |
| C(9)—C(6)—C(7) | 108(2) |
| C(8)—C(6)—C(7) | 106(2) |
| C(9)—C(6)—P(1) | 112(2) |
| C(8)—C(6)—P(1) | 114(2) |
| C(7)—C(6)—P(1) | 107(2) |
| C(12)—C(10)—C(13) | 109(2) |

TABLE 3-continued

Selected Bond Lengths and Angles

| | |
|---|---|
| C(12)—C(10)—C(11) | 99(2) |
| C(13)—C(10)—C(11) | 109(2) |
| C(12)—C(10)—P(1) | 119(2) |
| C(13)—C(10)—P(1) | 114(2) |
| C(11)—C(10)—P(1) | 105(2) |
| C(16)—C(14)—C(17) | 112(2) |
| C(16)—C(14)—C(15) | 108(2) |
| C(17)—C(14)—C(15) | 106(2) |
| C(16)—C(14)—P(1) | 114(2) |
| C(17)—C(14)—P(1) | 106(2) |
| C(15)—C(14)—P(1) | 110(2) |
| C(26)—C(18)—C(19) | 108(2) |
| C(26)—C(18)—Ti(1) | 100(2) |
| C(19)—C(18)—Ti(1) | 113.3(13) |
| C(24)—C(19)—C(20) | 120(2) |
| C(24)—C(19)—C(18) | 113(2) |
| C(20)—C(19)—C(18) | 125(2) |
| C(19)—C(20)—C(21) | 111(3) |
| C(22)—C(21)—C(20) | 123(3) |
| C(21)—C(22)—C(23) | 126(4) |
| C(22)—C(23)—C(24) | 116(3) |
| C(23)—C(24)—C(19) | 122(2) |
| C(23)—C(24)—C(25) | 140(2) |
| C(19)—C(24)—C(25) | 98(2) |
| C(26)—C(25)—C(24) | 112(2) |
| C(25)—C(26)—C(18) | 109(3) |
| C(35)—C(27)—C(28) | 108(2) |
| C(35)—C(27)—Ti(1) | 109.4(14) |
| C(28)—C(27)—Ti(1) | 114.3(13) |
| C(29)—C(28)—C(33) | 113(2) |
| C(29)—C(28)—C(27) | 137(2) |
| C(33)—C(28)—C(27) | 110(2) |
| C(30)—C(29)—C(28) | 125(2) |
| C(31)—C(30)—C(29) | 120(2) |
| C(30)—C(31)—C(32) | 123(2) |
| C(33)—C(32)—C(31) | 116(2) |
| C(34)—C(33)—C(32) | 130(2) |
| C(34)—C(33)—C(28) | 106(2) |
| C(32)—C(33)—C(28) | 124(2) |
| C(33)—C(34)—C(35) | 110(2) |
| C(27)—C(35)—C(34) | 106(2) |
| C(40)—C(36)—C(37) | 111(2) |
| C(40)—C(36)—Ti(2) | 72.1(10) |
| C(37)—C(36)—Ti(2) | 70.8(9) |
| C(36)—C(37)—C(38) | 101.6(14) |
| C(36)—C(37)—Ti(2) | 74.5(9) |
| C(38)—C(37)—Ti(2) | 70.0(9) |
| C(39)—C(38)—C(37) | 112(2) |
| C(39)—C(38)—Ti(2) | 72.8(10) |
| C(37)—C(38)—Ti(2) | 73.5(9) |
| C(38)—C(39)—C(40) | 107(2) |
| C(38)—C(39)—Ti(2) | 73.6(10) |
| C(40)—C(39)—Ti(2) | 75.4(10) |
| C(36)—C(40)—C(39) | 108(2) |
| C(36)—C(40)—Ti(2) | 74.4(9) |
| C(39)—C(40)—Ti(2) | 69.5(10) |
| C(43)—C(41)—C(44) | 107(2) |
| C(43)—C(41)—C(42) | 109(2) |
| C(44)—C(41)—C(42) | 107(2) |
| C(43)—C(41)—P(2) | 112(2) |
| C(44)—C(41)—P(2) | 108(2) |
| C(42)—C(41)—P(2) | 113(2) |
| C(47)—C(45)—C(48) | 110(2) |
| C(47)—C(45)—C(46) | 110(2) |
| C(48)—C(45)—C(46) | 104(2) |
| C(47)—C(45)—P(2) | 114(2) |
| C(48)—C(45)—P(2) | 111(2) |
| C(46)—C(45)—P(2) | 106.6(14) |
| C(52)—C(49)—C(50) | 110(2) |
| C(52)—C(49)—C(51) | 109(2) |
| C(50)—C(49)—C(51) | 107(2) |
| C(52)—C(49)—P(2) | 112(2) |
| C(50)—C(49)—P(2) | 113(2) |
| C(51)—C(49)—P(2) | 103.9(14) |
| C(54)—C(53)—C(61) | 102(2) |
| C(54)—C(53)—Ti(2) | 113(2) |
| C(61)—C(53)—Ti(2) | 109.0(14) |

TABLE 3-continued

Selected Bond Lengths and Angles

| | |
|---|---|
| C(55)—C(54)—C(53) | 144(2) |
| C(55)—C(54)—C(59) | 111(2) |
| C(53)—C(54)—C(59) | 105(2) |
| C(56)—C(55)—C(54) | 132(3) |
| C(55)—C(56)—C(57) | 115(3) |
| C(58)—C(57)—C(56) | 117(3) |
| C(57)—C(58)—C(59) | 120(3) |
| C(60)—C(59)—C(58) | 117(2) |
| C(60)—C(59)—C(54) | 120(2) |
| C(58)—C(59)—C(54) | 123(2) |
| C(59)—C(60)—C(61) | 99(2) |
| C(60)—C(61)—C(53) | 113(2) |
| C(70)—C(62)—C(63) | 99(2) |
| C(70)—C(62)—Ti(2) | 111(2) |
| C(63)—C(62)—Ti(2) | 117(2) |
| C(64)—C(63)—C(68) | 122(2) |
| C(64)—C(63)—C(62) | 131(2) |
| C(68)—C(63)—C(62) | 108(2) |
| C(65)—C(64)—C(63) | 121(2) |
| C(64)—C(65)—C(66) | 112(2) |
| C(65)—C(66)—C(67) | 125(2) |
| C(68)—C(67)—C(66) | 124(2) |
| C(67)—C(68)—C(63) | 116(2) |
| C(67)—C(68)—C(69) | 136(2) |
| C(63)—C(68)—C(69) | 108(2) |
| C(70)—C(69)—C(68) | 108(2) |
| C(69)—C(70)—C(62) | 117(2) |

TABLE 4

Anisotropic Displacement Parameters

| | U11 | U22 | U33 | U23 | U13 | U12 |
|---|---|---|---|---|---|---|
| Ti(1) | 2(2) | 69(3) | 83(3) | 1(3) | 2(2) | −5(2) |
| Ti(2) | 63(3) | 48(2) | 31(2) | −3(2) | 18(2) | −1(2) |
| P(1) | 24(3) | 63(4) | 62(5) | −4(4) | 3(3) | 0(3) |
| P(2) | 45(4) | 40(3) | 47(4) | −6(3) | 14(3) | 1(3) |
| N(1) | 30(10) | 13(8) | 70(14) | −27(8) | −17(9) | 12(8) |
| N(2) | 28(10) | 62(11) | 44(12) | −6(10) | 6(9) | −15(9) |

TABLE 5

Hydrogen Coordinates and Isotropic Displacement Parameters

| | x | y | z | U(eq) |
|---|---|---|---|---|
| H(1A) | 572(16) | 3168(10) | 3774(19) | 84 |
| H(2A) | −98(16) | 3307(11) | 1735(17) | 78 |
| H(3A) | −602(18) | 4510(11) | 3194(22) | 90 |
| H(4A) | −274(15) | 5159(11) | 3114(17) | 75 |
| H(5A) | 477(14) | 4324(10) | 4493(17) | 72 |
| H(7A) | 257(18) | 6695(12) | 1171(20) | 90 |
| H(7B) | −75(18) | 6892(12) | 2263(20) | 90 |
| H(7C) | 6(18) | 6124(12) | 1955(20) | 90 |
| H(8A) | 1926(16) | 7431(10) | 1662(19) | 84 |
| H(8B) | 2686(16) | 7336(10) | 2764(19) | 84 |
| H(8C) | 1518(16) | 7612(10) | 2723(19) | 84 |
| H(9A) | 3131(18) | 5920(10) | 3620(17) | 68 |
| H(9B) | 1155(18) | 6683(10) | 3904(17) | 68 |
| H(9C) | 2320(18) | 6403(10) | 3940(17) | 68 |
| H(11A) | 220(21) | 5727(13) | 286(23) | 105 |
| H(11B) | 858(21) | 5063(13) | 120(23) | 105 |
| H(11C) | 495(21) | 5558(13) | −841(23) | 105 |
| H(12A) | 2625(18) | 5144(11) | −103(20) | 100 |
| H(12B) | 3200(18) | 5815(11) | −358(20) | 100 |
| H(12C) | 2147(18) | 5579(11) | −1106(20) | 100 |
| H(13A) | 1335(22) | 6958(13) | 204(24) | 130 |
| H(13B) | 1379(22) | 6685(13) | −946(24) | 130 |
| H(13C) | 2436(22) | 6914(13) | −198(24) | 130 |
| H(15A) | 3921(21) | 5797(13) | 3663(21) | 108 |

TABLE 5-continued

Hydrogen Coordinates and Isotropic Displacement Parameters

| | x | y | z | U(eq) |
|---|---|---|---|---|
| H(15B) | 3772(21) | 6587(13) | 3550(21) | 108 |
| H(15C) | 4886(21) | 6256(13) | 3485(21) | 108 |
| H(16A) | 3734(23) | 7145(13) | 1703(24) | 130 |
| H(16B) | 3949(23) | 6706(13) | 733(24) | 130 |
| H(16C) | 4871(23) | 6828(13) | 1708(24) | 130 |
| H(17A) | 4152(19) | 5062(11) | 2084(20) | 107 |
| H(17B) | 5319(19) | 5511(11) | 1935(20) | 107 |
| H(17C) | 4212(19) | 5381(11) | 967(20) | 107 |
| H(18A) | 2266(18) | 3095(11) | 2000(18) | 59 |
| H(20A) | 4388(24) | 3356(14) | 2830(26) | 97 |
| H(21A) | 5929(22) | 3820(12) | 2155(23) | 90 |
| H(22A) | 5847(25) | 3982(13) | 485(24) | 86 |
| H(23A) | 4278(26) | 4134(15) | −680(29) | 113 |
| H(25A) | 1791(15) | 3842(9) | −747(17) | 54 |
| H(26A) | 855(24) | 3507(13) | 654(23) | 107 |
| H(27A) | 3611(16) | 4276(9) | 3893(16) | 36 |
| H(29A) | 3283(153) | 2799(20) | 3800(51) | 81 |
| H(30A) | 2907(19) | 1950(14) | 4800(21) | 104 |
| H(31A) | 2367(14) | 2158(9) | 6394(17) | 65 |
| H(32A) | 2156(16) | 3246(11) | 6982(19) | 80 |
| H(34A) | 2280(16) | 4624(11) | 6362(20) | 88 |
| H(35A) | 2901(18) | 5220(13) | 4753(19) | 73 |
| H(36A) | 5011(13) | 8453(9) | −2471(14) | 49 |
| H(37A) | 5353(12) | 9768(8) | −2648(15) | 56 |
| H(38A) | 6160(13) | 10156(9) | −659(14) | 48 |
| H(39A) | 6237(15) | 9173(9) | 592(17) | 55 |
| H(40A) | 5556(14) | 8096(9) | −520(16) | 55 |
| H(42A) | 1946(21) | 12078(12) | 234(21) | 106 |
| H(42B) | 1632(21) | 11563(12) | 1070(21) | 106 |
| H(42C) | 793(21) | 11759(12) | 58(21) | 106 |
| H(43A) | 1451(18) | 10334(10) | 586(18) | 88 |
| H(43B) | 1536(18) | 10098(10) | −574(18) | 88 |
| H(43C) | 569(18) | 10551(10) | −379(18) | 88 |
| H(44A) | 2102(22) | 11655(13) | −1583(21) | 121 |
| H(44B) | 952(22) | 13140(13) | −1672(21) | 121 |
| H(44C) | 1914(22) | 10884(13) | −1871(21) | 121 |
| H(46A) | 4457(23) | 10885(14) | −1758(23) | 135 |
| H(46B) | 4709(23) | 11637(14) | −2039(23) | 135 |
| H(46C) | 3516(23) | 11400(14) | −2110(23) | 135 |
| H(47A) | 3174(19) | 12325(12) | −756(21) | 129 |
| H(47B) | 4338(19) | 12573(12) | −817(21) | 129 |
| H(47C) | 4012(19) | 12424(12) | 295(21) | 129 |
| H(48A) | 5671(22) | 11033(15) | −42(25) | 152 |
| H(48B) | 5544(22) | 11636(15) | 733(25) | 152 |
| H(48C) | 5874(22) | 11782(15) | −378(25) | 152 |
| H(50A) | 3417(22) | 11936(12) | 1813(23) | 121 |
| H(50B) | 4643(22) | 11903(12) | 1752(23) | 121 |
| H(50C) | 4238(22) | 11668(12) | 2792(23) | 121 |
| H(51A) | 2280(18) | 10846(11) | 1908(20) | 112 |
| H(51B) | 3121(18) | 10583(11) | 2874(20) | 112 |
| H(51C) | 2821(18) | 10133(11) | 1849(20) | 112 |
| H(52A) | 4794(21) | 10118(13) | 1613(23) | 104 |
| H(52B) | 5069(21) | 10553(13) | 2658(23) | 104 |
| H(52C) | 5470(21) | 10787(13) | 1616(23) | 104 |
| H(53A) | 3674(18) | 8103(12) | −205(20) | 72 |
| H(55A) | 1336(19) | 8544(11) | −1089(21) | 69 |
| H(56A) | −226(21) | 8549(12) | −453(21) | 81 |
| H(57A) | −123(26) | 9112(13) | 1350(24) | 101 |
| H(58A) | 1569(20) | 9103(12) | 2471(23) | 68 |
| H(60A) | 3539(17) | 8947(10) | 2705(20) | 83 |
| H(61A) | 4826(17) | 8517(10) | 1464(17) | 56 |
| H(62A) | 2134(20) | 9333(11) | −2089(19) | 67 |
| H(64A) | 2517(159) | 7873(18) | −2094(68) | 82 |
| H(65A) | 2796(17) | 7003(12) | −3382(20) | 81 |
| H(66A) | 3333(16) | 7437(11) | −4983(19) | 89 |
| H(67A) | 3519(18) | 8508(11) | −5290(21) | 99 |
| H(69A) | 3310(14) | 9865(10) | −4512(17) | 63 |
| H(70A) | 2963(18) | 10265(13) | −2896(21) | 82 |

What is claimed is:

1. An organometallic complex defined by the formula:

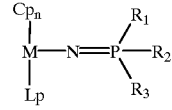

wherein M is a group 4 metal in oxidation state 4;

each Cp is selected from the group consisting of unsubstituted cyclopentadienyl, substituted cyclopentadienyl, unsubstituted indenyl, substituted indenyl, unsubstituted fluorenyl and substituted fluorenyl;

each of $R_1$, $R_2$ and $R_3$ is a hydrocarbyl group which is bonded to phosphorus by a carbon-phosphorus single bond;

n is 2 or 3 and n+p=3; and when p=1, L is a monoanionic ligand.

2. The organometallic complex of claim 1 wherein M is Ti.

3. The organometallic complex of claim 1 wherein n is 3 and each Cp is selected from the group consisting of unsubstituted cyclopentadienyl and unsubstituted indenyl.

4. The organometallic complex of claim 1 wherein each R is an alkyl group.

5. The organometallic complex of claim 4 wherein each R is tertiary butyl.

* * * * *